(12) United States Patent
Chau et al.

(10) Patent No.: US 7,442,716 B2
(45) Date of Patent: Oct. 28, 2008

(54) 2-(PHENYL OR HETEROCYCLIC)-1H-PHENANTRHO[9,10-D]IMIDAZOLES AS MPGES-1 INHIBITORS

(75) Inventors: Anh Chau, Saint-Laurent (CA); Bernard Cote, L'lle-Perrot (CA); Yves Ducharme, Montreal (CA); Richard Frenette, Laval (CA); Richard Friesen, Kirkland (CA); Marc Gagnon, Montreal (CA); Andre Giroux, Ste-Anne-De-Bellevue (CA); Evelyn Martins, Vaudreuil (CA); Hongping Yu, Kirkland (CA); Tom Wu, Pointe Claire (CA)

(73) Assignee: Merck Frosst Canada Ltd., Quebec (CA)

( * ) Notice: Subject to any disclaimer, the term of this patent is extended or adjusted under 35 U.S.C. 154(b) by 503 days.

(21) Appl. No.: 11/374,288

(22) Filed: Nov. 23, 2005

(65) Prior Publication Data
US 2007/0208017 A1  Sep. 6, 2007

Related U.S. Application Data

(60) Provisional application No. 60/637,180, filed on Dec. 17, 2004.

(51) Int. Cl.
A61K 31/4184 (2006.01)
A61K 31/5377 (2006.01)
C07D 235/02 (2006.01)
C07D 413/14 (2006.01)

(52) U.S. Cl. ............... 514/387; 548/300.1; 548/301.7; 546/268.1; 546/268.4; 546/272.7; 546/273.1; 544/106; 544/111; 544/132; 544/139; 514/385; 514/231.2; 514/231.5; 514/232.8

(58) Field of Classification Search ............ 548/300.1, 548/301.7; 546/268.1, 268.4, 272.7, 273.1; 544/106, 111, 132, 139; 514/385, 387, 231.2, 514/231.5, 232.8
See application file for complete search history.

(56) References Cited

U.S. PATENT DOCUMENTS

| 3,637,584 | A | 1/1972 | Hurlock et al. |
| 4,770,976 | A | 9/1988 | Loerzer et al. |
| 4,857,438 | A | 8/1989 | Loerzer et al. |
| 6,451,520 | B1 | 9/2002 | Odenwalder et al. |
| 2004/0209117 | A1 | 10/2004 | Aziz et al. |
| 2004/0265628 | A1 | 12/2004 | Wang et al. |

FOREIGN PATENT DOCUMENTS

| CA | 1 135 704 | 11/1982 |
| CA | 2223551 | 6/1998 |
| CA | 2261426 | 8/1999 |
| CA | 2426457 | 4/2002 |
| EP | 1 705 740 A1 | 9/2006 |
| JP | 63-287963 | 11/1988 |
| JP | 5-273618 | 10/1993 |
| JP | 2937281 | 6/1999 |
| JP | 2001-23777 | 1/2001 |
| WO | WO 92/04330 | 3/1992 |
| WO | WO 2004/016086 A2 | 2/2004 |
| WO | WO 2005/047266 A1 | 5/2005 |
| WO | WO 2006 063 466 | 6/2006 |

OTHER PUBLICATIONS

CAS Registry (Online) STN International, US Registry No. 41049-73-4, 1H-Phenanthro[9,10-d]imidazole, 2-(2,4,6-trimethylphenyl)-, radical ion(2-), dipotassium (1CI), Entered STN: Nov. 16, 1984.
CAS Registry (Online) STN International, US Registry No. 403665-58-7, 1H-Phenanthro[9,10-d]imidazole, 2-(2,4,6-trimethoxyphenyl)-9CI), Entered STN: Mar. 31, 2002.
CAS Registry (Online) STN International, US Registry No. 667408-12-0. 1H-Phenanthro[9,10-d]imidazole, 2-(2,6-dichlorophenyl)-(9CI), Entered STN: Mar. 25, 2004.
Isikdag, I, et al., "Synthesis and analgesic activities of 2-substituted-1H-phenantro[9,10-d] imidazoles" Bollettino Chimico Farmaceutico, vol. 138, No. 9, pp. 453-456, 1999.
Zeytinoglu, H, et al., "Mutagenicity Assay in *Salmonella* for Thirteen 2-Substituted-1H-phenanthro (9,10-d) Imidazoles" Drug and Chemical Toxicology, vol. 26, No. 4, pp. 245-257, 2003.
Allen, D.W. et al., "Synthesis, spectroscopic studies and structural characterisation of some new 2-(phosphonioaryl)imidazolide betaines" J. Chem. Soc., vol. 1, pp. 335-340, 1998.

(Continued)

Primary Examiner—Golam M Shameem
(74) Attorney, Agent, or Firm—Curtis C. Panzer; Valerie J. Camara

(57) ABSTRACT

The invention encompasses novel compounds of Formula I

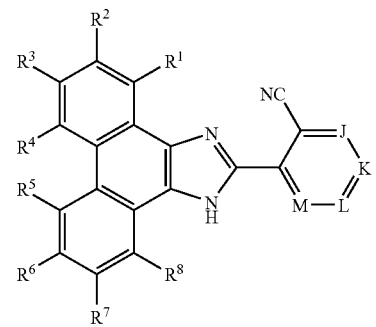

or pharmaceutically acceptable salts thereof. These compounds are inhibitors of the microsomal prostaglandin E synthase-1 (mPGES-1) enzyme and are therefore useful to treat pain and/or inflammation from a variety of diseases or conditions, such as osteoarthritis, rheumatoid arthritis and acute or chronic pain. Methods of treating diseases or conditions mediated by the mPGES-1 enzyme and pharmaceutical compositions are also encompassed.

27 Claims, No Drawings

OTHER PUBLICATIONS

Lantos, I., "Reaction of Phenanthrenequinone with Ammonium Acetate" J. Org. Chem., vol. 40, No. 11, pp. 1641-1642, 1975.

Neunhoeffer, O., et al., "Chemiluminescence of lophine and analogous compounds" Zeitschrift fuer Naturforschung, Teil B: Anorganische Chemie, Organische Chemie, Biochemie, Biophysik, Biologie, vol. 21, No. 6, pp. 536-539, 1966.

Ranganathan, S., et al., "Fascinating problems in Organic reaction Mechanisms VIII: Reactions and rearrangements of Phenanthraquinone Monoimine" Heterocycles, vol. 7, No. 1, pp. 529-545, 1977.

Pillai, V.N.R., et al., "Photochemical and Thermal Synthesis of Phenanthr[9,10-d] Imidazoles", Current Science, vol. 47, No. 17, pp. 627-629, 1978.

Yasuda, G., et al., "Crystal Structure of 1-Ethyl-2-(2-nitrophenyl)-phenanthro[9,10-d]imidazole" Analytical Sciences, vol. 13, pp. 1053-1054, 1997.

Morita, H., et al., "Photochemical Behavior of Hexaarylbiimidazole in solid polymer Matrices" Journal of Photopolymer Science and Technology, vol. 5, No. 3, pp. 551-556, 1992.

Kiesele, V.H. et al., "ESR Studies of radical dianions of substituted phenanthromidazoles" Berichte der Bunsen-Gesellschaft, vol. 77, No. 2, pp. 108-116, 1973.

Sakaino, Y., et al., "Structure of the Chromotropic Dimers produced from 2-Arylphenanthro-[9,10-d]imidazoles" Journal of the Chemical Society, Perkin Transactions 1: Organic and Bio-Organic Chemistry, vol. 22, pp. 2361-2364, 1975.

Dash, B. et al., "Structure of Phenanthraquinoneimide Anhydride- Some New Transformations" Journal of the Indian Chemical Society, vol. 56, No. 10, pp. 1017-1019, 1979.

Wang, K.Z. et al., "First proton-induced near-infrared fluorescent switch at room temperature of a novel Ru(II) complex" Inorganic Chemistry Communications, vol. 5, pp. 841-843, 2002.

US 7,442,716 B2

2-(PHENYL OR HETEROCYCLIC)-1H-PHENANTRHO[9,10-D]IMIDAZOLES AS MPGES-1 INHIBITORS

CROSS REFERENCE TO RELATED APPLICATIONS

This application claims the benefit of U.S. Provisional Application No. 60/637,180, filed Dec. 17, 2004.

BACKGROUND OF THE INVENTION

Modulation of prostaglandin metabolism is at the center of current anti-inflammatory therapies. NSAIDs and COX-2 inhibitors block the activity of cyclooxygenases and their ability to convert arachidonic acid (AA) into prostaglandin (PG)H2. PGH2 can be subsequently metabolized by terminal prostaglandin synthases to the corresponding biologically active PGs, namely, PGI2, thromboxane (Tx) A2, PGD2, PGF2α, and PGE2. A combination of pharmacological, genetic, and neutralizing antibody approaches demonstrates the importance of PGE2 in inflammation. In many respects, disruption of PGE2-dependent signalling in animal models of inflammation can be as effective as treatment with NSAIDs or COX-2 inhibitors. The conversion of PGH2 to PGE2 by prostaglandin E synthases (PGES) may therefore represent a pivotal step in the propagation of inflammatory stimuli.

Microsomal prostaglandin E synthase-1 (mPGES-1) is an inducible PGES after exposure to pro-inflammatory stimuli. mPGES-1 is induced in the periphery and in the CNS by inflammation and represents therefore a novel target for acute and chronic inflammatory disorders. The rationale for the development of specific mPGES-1 inhibitors revolves around the hypothesis that the therapeutic utility of NSAIDs and Cox-2 inhibitors would be largely due to inhibition of pro-inflammatory PGE2 while the side effect profile would be largely due to inhibition of other prostaglandins.

The present invention is directed to novel compounds that are selective inhibitors of the microsomal prostaglandin E synthase-1 enzyme and would therefore be useful for the treatment of pain and inflammation in a variety of diseases or conditions, such as osteoarthritis, rheumatoid arthritis and acute or chronic pain. Furthermore, by selectively inhibiting the pro-inflammatory PGE2, it is believed the compounds of the invention would have a reduced potential for side effects associated with the inhibition of other prostaglandins by conventional non-steoidal anti-inflammatory drugs, such as gastrointestinal and renal toxicity.

SUMMARY OF THE INVENTION

The invention encompasses novel compounds of Formula I

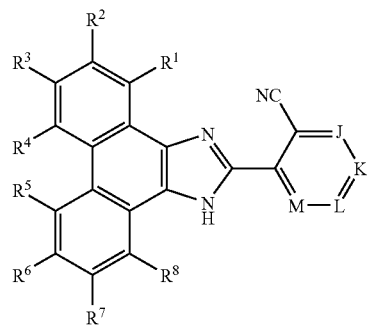

or pharmaceutically acceptable salts thereof. These compounds are inhibitors of the microsomal prostaglandin E synthase-1 (mPGES-1) enzyme and are therefore useful to treat pain and/or inflammation from a variety of diseases or conditions, such as osteoarthritis, rheumatoid arthritis and acute or chronic pain. Methods of treating diseases or conditions mediated by the mPGES-1 enzyme and pharmaceutical compositions are also encompassed.

DETAILED DESCRIPTION OF THE INVENTION

The invention encompasses a genus of compounds represented by Formula I

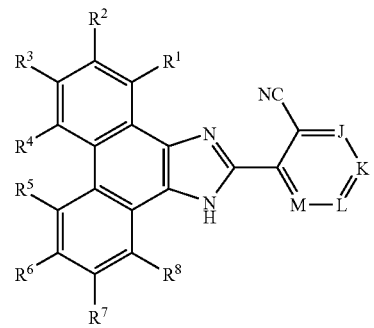

or a prodrug thereof, or a pharmaceutically acceptable salt of said compound or prodrug, wherein:

J is selected from the group consisting of —C($X^2$)— and —N—,

K is selected from the group consisting of —C($X^3$)— and —N—,

L is selected from the group consisting of —C($X^4$)— and —N—, and

M is selected from the group consisting of —C($X^5$)— and —N—, with the proviso that at least one of J, K, L or M is other than —N—;

$X^2$, $X^3$, $X^4$ and $X^5$ are independently selected from the group consisting of: (1) H; (2) —CN; (3) F; (4) Cl; (5) Br; (6) I; (7) —OH; (8) —$N_3$; (9) $C_{1-6}$alkyl, $C_{2-6}$alkenyl or $C_{2-6}$alkynyl, wherein one or more of the hydrogen atoms attached to said $C_{1-6}$alkyl, $C_{2-6}$alkenyl or $C_{2-6}$alkynyl may be replaced with a fluoro atom, and said $C_{1-6}$alkyl, $C_{2-6}$alkenyl or $C_{2-6}$alkynyl may be optionally substituted with a hydroxy group; (10) $C_{1-4}$alkoxy; (11) $NR^9R^{10}$—C(O)—$C_{1-4}$alkyl-O—; (12) $C_{1-4}$alkyl-S(O)$_k$—; (13) —$NO_2$; (14) $C_{3-6}$cycloalkyl, (15) $C_{3-6}$cycloalkoxy; (16) phenyl, (17) carboxy; and (18) $C_{1-4}$alkyl-O—C(O)—; $R^1$, $R^2$, $R^3$, $R^4$, $R^5$, $R^6$, $R^7$ and $R^8$ are independently selected from the group consisting of: (1) H; (2) F; (3) Cl; (4) Br; (5) I; (6) —CN; (7) $C_{1-6}$alkyl or $C_{2-6}$alkenyl, wherein one or more of the hydrogen atoms attached to said $C_{1-6}$alkyl or $C_{2-6}$alkenyl may be replaced with a fluoro atom, and wherein said $C_{1-6}$alkyl or $C_{2-6}$alkenyl may be optionally substituted with one to three substituents independently selected from the group consisting of: —OH, methoxy, $R^{11}$—O—C (O)—, cyclopropyl, pyridyl and phenyl; (8) $C_{3-6}$cycloalkyl; (9) $R^{12}$—O—; (10) $R^{13}$—S(O)$_k$—, (11) $R^{14}$—S(O)$_k$—N($R^{15}$)—; (12) $R^{16}$—C(O)—; (13) $R^{17}$—N($R^{18}$)—; (14) $R^{19}$—N($R^{20}$)—C(O)—; (15) $R^{21}$—N($R^{22}$)—S(O)$_k$—; (16) $R^{23}$—C(O)—N($R^{24}$)—; (17) Z-C≡C; (18) —($CH_3$)C═N—OH or —($CH_3$)C═N—

OCH₃; and (19) phenyl, naphthyl, pyridyl, pyradazinyl, pyrimidinyl, pyrazinyl, pyrrolyl, pyrazolyl, imidazolyl, triazolyl, tetrazolyl, oxazolyl, isoxazolyl, oxadiazolyl, thienyl or furyl, each optionally substituted with a substituent independently selected from the group consisting of: F, Cl, Br, I, $C_{1-4}$alkyl, phenyl, methylsulfonyl, methylsulfonylamino, $R^{25}$—O—C(O)— and $R^{26}$—N($R^{27}$)—, said $C_{1-4}$alkyl optionally substituted with 1 to 3 groups independently selected from halo and hydroxy;

each Z is independently selected from the group consisting of: (1) H; (2) $C_{1-6}$alkyl, wherein one or more of the hydrogen atoms attached to said $C_{1-6}$alkyl may be replaced with a fluoro atom, and wherein $C_{1-6}$alkyl is optionally substituted with one to three substituents independently selected from: hydroxy, methoxy, cyclopropyl, phenyl, pyridyl, pyrrolyl, $R^{28}$—N($R^{29}$)— and $R^{30}$—O—C(O)—; (3) —(CH₃)C═N—OH or —(CH₃)C═N—OCH₃; (4) $R^{31}$—C(O)—; (5) phenyl; (6) pyridyl or the N-oxide thereof; (7) $C_{3-6}$cycloalkyl, optionally substituted with hydroxy; (8) tetrahydropyranyl, optionally substituted with hydroxy; and (9) a five-membered aromatic heterocycle containing 1 to 3 atoms independently selected from O, N or S and optionally substituted with methyl;

each $R^9$, $R^{10}$, $R^{15}$, $R^{24}$ and $R^{32}$ is independently selected from the group consisting of: (1) H; and (2) $C_{1-4}$alkyl;

each $R^{11}$, $R^{12}$, $R^{13}$, $R^{14}$, $R^{16}$, $R^{23}$, $R^{25}$, $R^{30}$ and $R^{31}$ is independently selected from the group consisting of: (1) H; (2) $C_{1-4}$alkyl, (3) $C_{3-6}$cycloalkyl; (4) phenyl, (5) benzyl; and (6) pyridyl; said $C_{1-4}$alkyl, $C_{3-6}$cycloalkyl, phenyl, benzyl and pyridyl may each be optionally substituted with 1 to 3 substituents independently selected from the group consisting of: OH, F, Cl, Br and I;

each $R^{17}$, $R^{18}$, $R^{19}$, $R^{20}$, $R^{21}$, $R^{22}$, $R^{26}$, $R^{27}$, $R^{28}$ and $R^{29}$ is independently selected from the group consisting of: (1) H; (2) $C_{1-6}$alkyl; (3) $C_{1-6}$alkoxy; (4) OH and (5) benzyl or 1-phenylethyl; and $R^{17}$ and $R^{18}$, $R^{19}$ and $R^{20}$, $R^{21}$ and $R^{22}$, $R^{26}$ and $R^{27}$, and $R^{28}$ and $R^{29}$ may be joined together with the nitrogen atom to which they are attached to form a monocyclic ring of 5 or 6 carbon atoms, optionally containing one or two atoms independently selected from —O—, —S(O)$_k$— and —N($R^{32}$)—; and each k is independently 0, 1 or 2.

Within this genus, the invention encompasses a sub-genus of compounds represented by Formula A

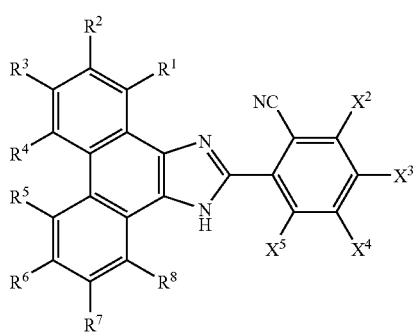

A or a prodrug thereof, or a pharmaceutically acceptable salt of said compound or prodrug.

Within this sub-genus, the invention encompasses a class of compounds of Formula A wherein:

$X^2$, $X^3$, $X^4$ and $X^5$ are independently selected from the group consisting of: (1) H; (2) —CN; (3) F; (4) Cl; (5) Br; and (6) I.

Also within this sub-genus, the invention encompasses a class of compounds of Formula A wherein $X^2$, $X^3$ and $X^4$ are H, and $X^5$ is other than H. Within this class, the invention encompasses a sub-class of compounds of Formula A wherein $X^5$ is —CN.

Also within this sub-genus, the invention encompasses a class of compounds of Formula A wherein at least one of $R^1$ or $R^8$ is other than H.

Also within this sub-genus, the invention encompasses a class of compounds of Formula A wherein at least one of $R^2$ or $R^7$ is other than H.

Also within this sub-genus, the invention encompasses a class of compounds of Formula A wherein at least one of $R^4$ or $R^5$ is other than H.

Also within this sub-genus, the invention encompasses a class of compounds of Formula A wherein: at least one of $R^3$ or $R^6$ is other than H; and $R^1$, $R^2$, $R^4$, $R^5$, $R^7$ and $R^8$ are H. Within this class, the invention encompasses a sub-class of compounds of Formula A wherein $R^3$ and $R^6$ are both other than H. Within this sub-class, the invention encompasses compounds of Formula A wherein: one of $R^3$ or $R^6$ is independently selected from the group consisting of: F, Cl, Br and I; and the other of $R^3$ or $R^6$ is Z-C≡C. Also within this class, the invention encompasses a sub-class of compounds of Formula A wherein: $R^3$ and $R^6$ are independently selected from the group consisting of: hydrogen, fluoro, chloro, bromo, iodo, cyano, methyl, ethyl, vinyl, cyclopropyl, —CO₂i-Pr, —CO₂CH₃, —SO₂CF₃, 3-pyridyl, acetyl,

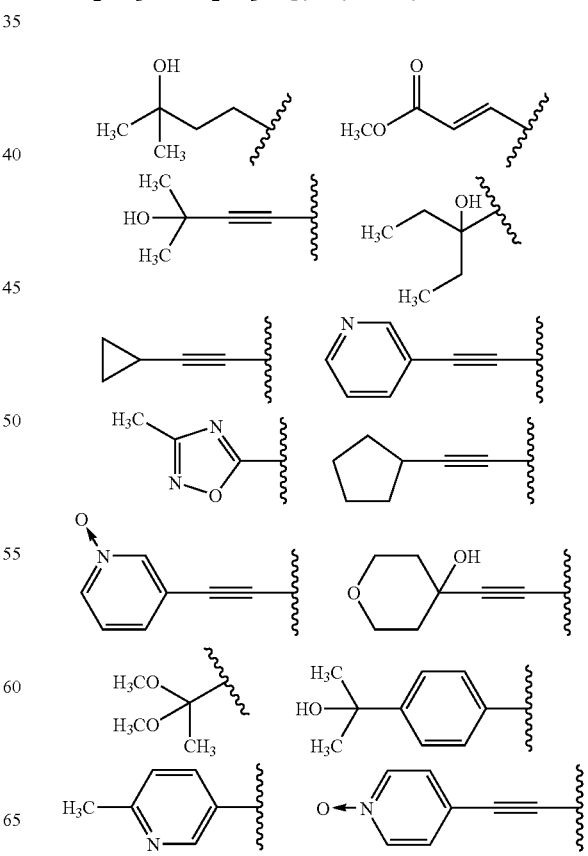

-continued

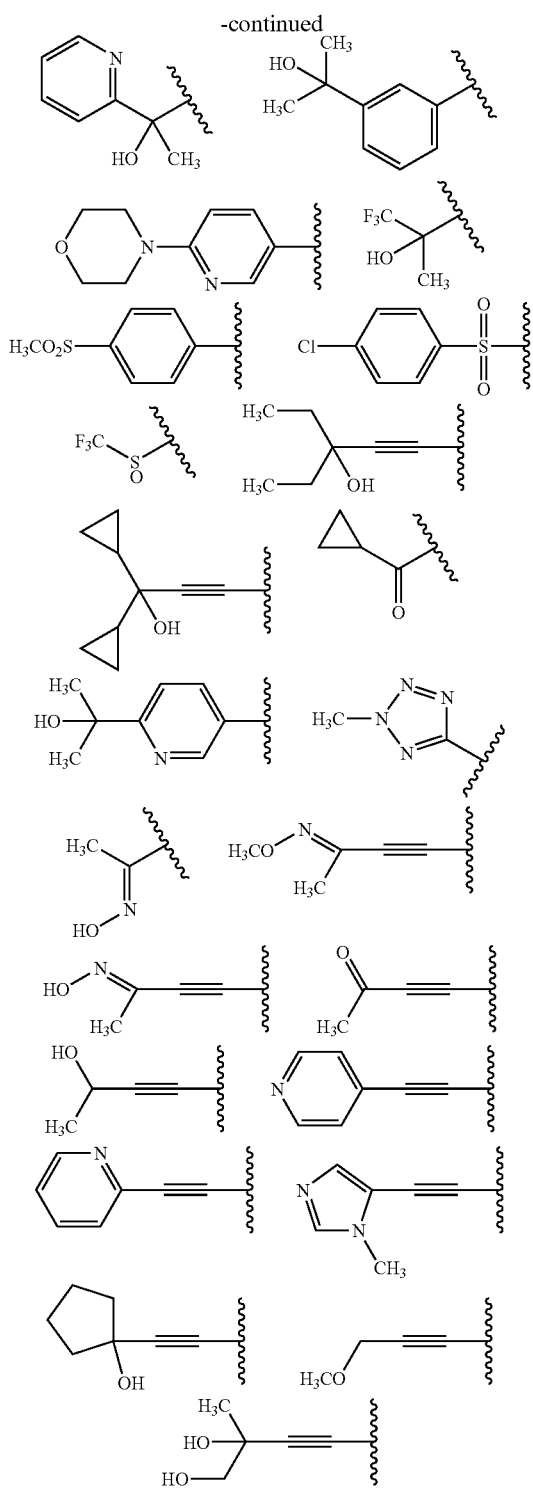
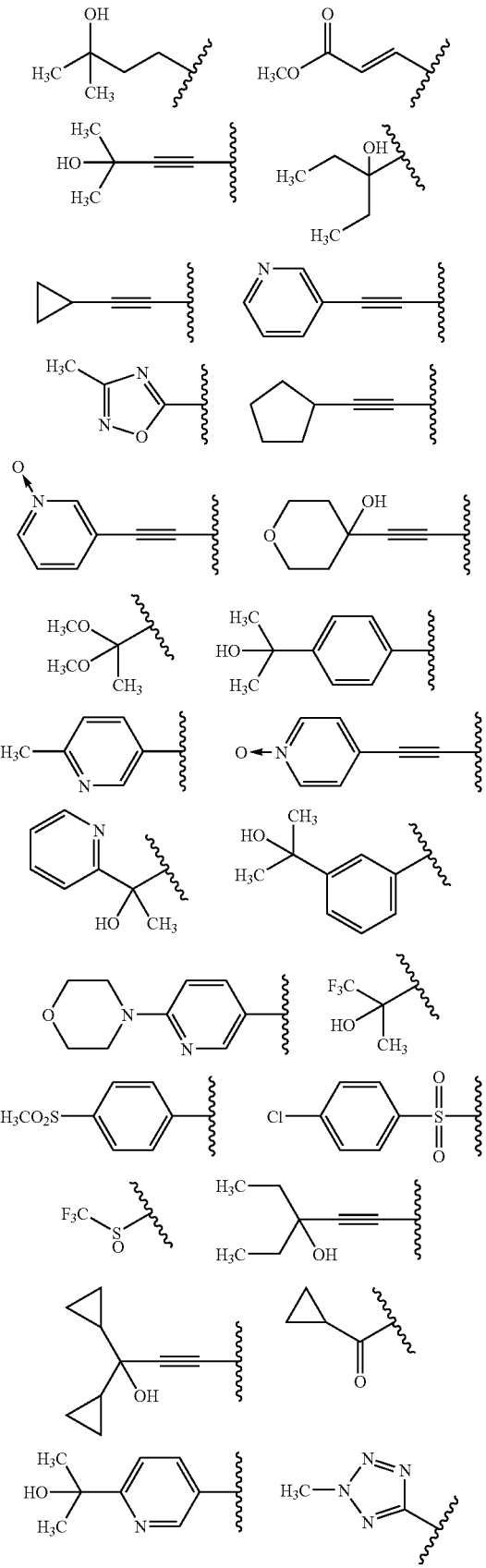

with the proviso that at least one of $R^3$ or $R^6$ is other than hydrogen.

Also within this class, the invention encompasses a subclass of compounds of Formula A wherein: $R^3$ and $R^6$ are independently selected from the group consisting of: hydrogen, fluoro, chloro, bromo, iodo, cyano, methyl, methoxy, ethyl, vinyl, cyclopropyl, propyl, butyl, —CO$_2$i-Pr, —CO$_2$CH$_3$, —SO$_2$CF$_3$, 3-pyridyl, acetyl, -continued
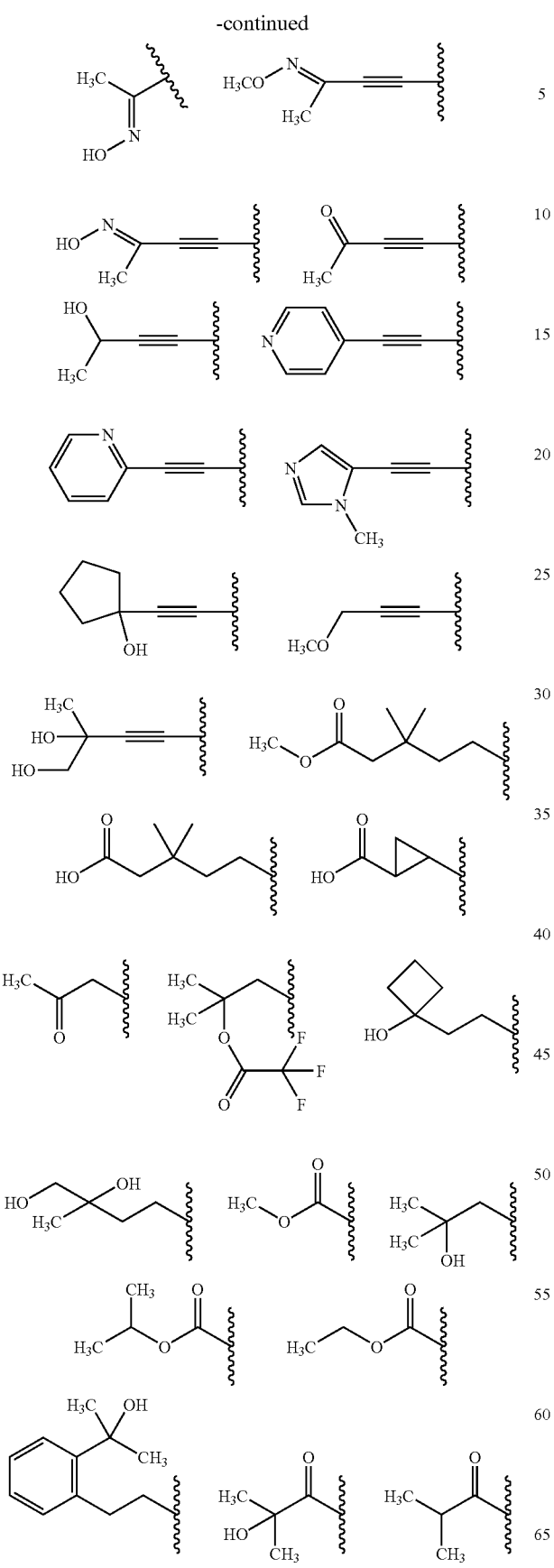
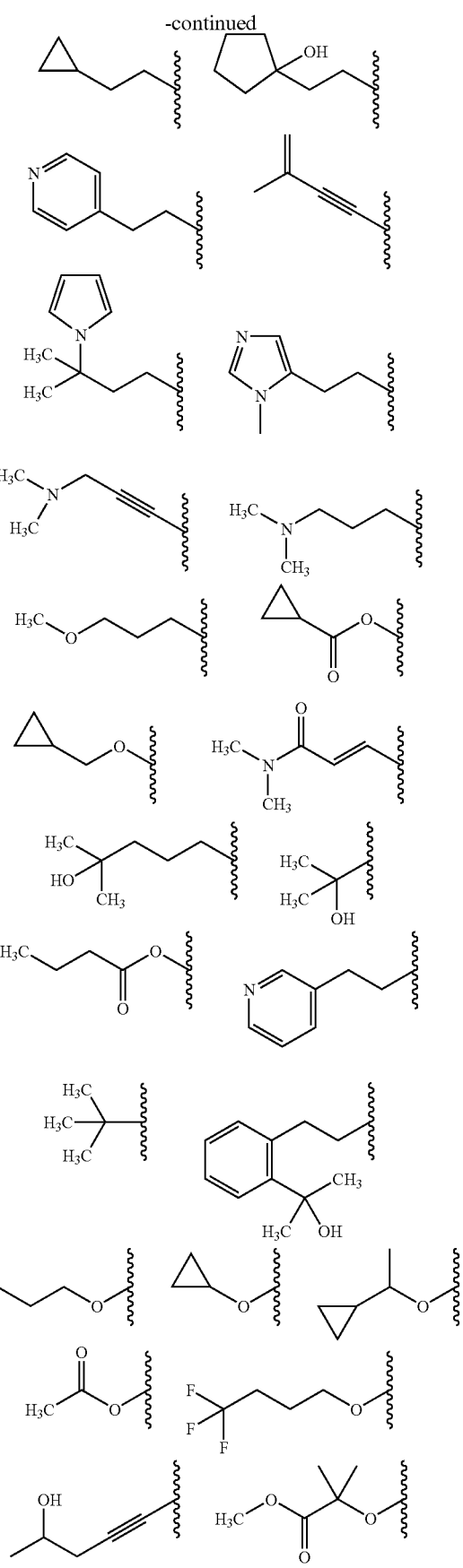

-continued

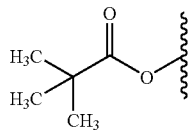

with the proviso that at least one of $R^3$ or $R^6$ is other than hydrogen.

Within the genus previously described, the invention encompasses a sub-genus of compounds of Formula B:

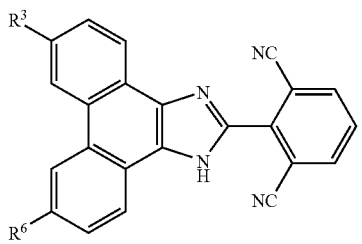

B or a prodrug thereof, or a pharmaceutically acceptable salt of said compound or prodrug. Within this sub-genus, the invention encompasses a class of compounds of Formula B wherein: one of $R^3$ or $R^6$ is independently selected from the group consisting of: F, Cl, Br and I; and the other of $R^3$ or $R^6$ is Z-C≡C.

Within the genus previously described, the invention encompasses a sub-genus of compounds of Formula I in accordance with Formula C

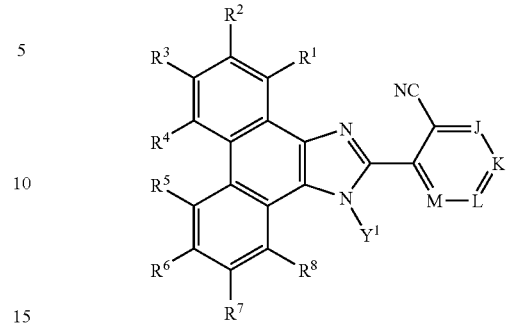

C or a pharmaceutically acceptable salt thereof, wherein:
$Y^1$ is selected from the group consisting of: (1) $C_{1-6}$alkyl; (2) $PO_4$—$C_{1-4}$alkyl-; (3) $C_{1-4}$alkyl-C(O)—O—$CH_2$—, wherein the $C_{1-4}$alkyl portion is optionally substituted with $R^{33}$—O—C(O)—; and (4) $C_{1-4}$alkyl-O—C(O)—; and
$R^{33}$ is selected from the group consisting of: (1) H; (2) $C_{1-4}$alkyl, (3) $C_{3-6}$cycloalkyl; (4) phenyl; (5) benzyl; and (6) pyridyl; said $C_{1-4}$alkyl, $C_{3-6}$cycloalkyl, phenyl, benzyl and pyridyl may each be optionally substituted with 1 to 3 substituents independently selected from the group consisting of: OH, F, Cl, Br and I.

The invention also encompasses a pharmaceutical composition comprising a compound of Formula I in combination with a pharmaceutically acceptable carrier.

The invention also encompasses a method for treating a microsomal prostaglandin B synthase-1 mediated disease or condition in a human patient in need of such treatment comprising administering to said patient a compound according to claim 1 in an amount effective to treat the microsomal prostaglandin E synthase-1 mediated disease or condition. Within this embodiment is encompassed the above method wherein the disease or condition is selected from the group consisting of: acute or chronic pain, osteoarthritis, rheumatoid arthritis, bursitis, ankylosing sponylitis and primary dysmenorrhea.

The following compounds exemplify the invention. These compounds were synthesized following the schemes and examples described below.

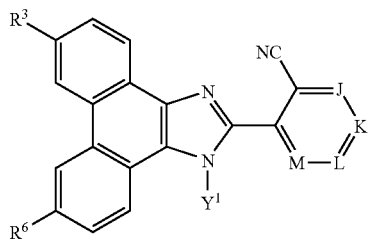

| Ex | $R^3/R^6$ | $R^6/R^3$ | J | K | L | M | $Y^1$ | (M + H)* |
|---|---|---|---|---|---|---|---|---|
| 1 | Cl | Br | CH | CH | CH | CF | H | 451 |
| 2 | H | H | CH | CH | CH | CH | H | 320 |
| 3 | CN | $F_3C$-C(OH)-$CF_3$ | CH | CH | CH | CF | H | 529 |

-continued

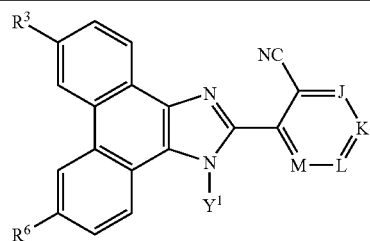

| Ex | R³/R⁶ | R⁶/R³ | J | K | L | M | Y¹ | (M + H)* |
|---|---|---|---|---|---|---|---|---|
| 4 | Cl | F₃C-C(OH)(CF₃)- | CH | CH | CH | CF | H | 538 |
| 5 | Cl | H | CH | CH | CH | CF | H | 372 |
| 6 | CN | H | CH | CH | CH | CF | H | 363 |
| 7 | CN | F₃C-C(OH)(CH₃)- | CH | CH | CH | CF | H | 475 |
| 8 | Cl | F₃C-C(OH)(CH₃)- | CH | CH | CH | CF | H | 484 |
| 9 | Br | Br | CH | CH | CH | CF | H | 495 |
| 10 | H | H | CH | CH | CH | CCl | H | 354 |
| 11 | H | H | CH | CH | CH | CCN | H | 345 |
| 12 | (CH₃)₂C(OH)-C≡C- | Br | CH | CH | CH | CF | H | 498 |
| 13 | (CH₃)₂C(OH)-C≡C- | (CH₃)₂C(OH)-C≡C- | CH | CH | CH | CF | H | 502 |
| 14 | (CH₃)₂C(OH)-C≡C- | Cl | CH | CH | CH | CF | H | 454 |
| 15 | (CH₃)₂C(OH)-C≡C- | I | CH | CH | CH | CF | H | 546 |
| 16 | H | H | CH | CH | CH | CBr | H | 399 |
| 17 | H | H | CH | CH | CH | CF | H | 338 |
| 18 | H | H | CH | N | CH | CCl | H | 354 |
| 19 | 3-pyridyl | 3-pyridyl | CH | CH | CH | CF | H | 492 |
| 20 | Cl | H₃C-C(=O)- | CH | CH | CH | CF | H | 414 |
| 21 | Cl | (CH₃)₂C(OH)- | CH | CH | CH | CF | H | 430 |

-continued

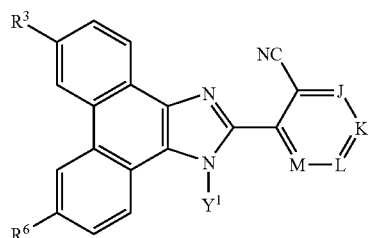

| Ex | R³/R⁶ | R⁶/R³ | J | K | L | M | Y¹ | (M + H)* |
|---|---|---|---|---|---|---|---|---|
| 22 | 3-pyridyl-C≡C- | Br | CH | CH | CH | CF | H | 517 |
| 23 | Cl | H | CH | N | CH | CCN | H | 380 |
| 24 | H | H | CH | N | CH | CCN | H | 346 |
| 25 | Cl | H | CH | CH | CH | CCN | H | 379 |
| 26 | H | H | CH | N | CH | CH | H | 321 |
| 27 | CH₃CH(OH)-C≡C-CH₃ | Br | CH | CH | CH | CF | H | 485 |
| 28 | CH₃C(O)-C≡C-CH₃ | Br | CH | CH | CH | CF | H | 483 |
| 29 | H₃C-C(O)- | H₃C-C(O)- | CH | CH | CH | CF | H | 422 |
| 30 | (CH₃)₂C(OH)-C≡C-CH₃ | H₃C-C(O)- | CH | CH | CH | CF | H | 462 |
| 31 | H | H | N | CH | CH | N | H | 322 |
| 32 | H | H | N | CH | CH | CH | H | 321 |
| 33 | Br | H₃C-C(O)- | CH | CH | CH | CF | H | 458 |
| 34 | I | I | CH | CH | CH | CF | H | 589 |
| 35 | Br | (CH₃)₂C(OH)- | CH | CH | CH | CF | H | 474 |
| 36 | Br | Cl | CH | CH | CH | CCN | H | 458 |
| 37 | Cl | H₃C-C(O)- | CH | CH | CH | CBr | H | 474 |
| 38 | Cl | H₃C-C(O)- | CH | CH | CH | CCN | H | 421 |
| 39 | I | I | CH | CH | CH | CCN | H | 597 |

-continued

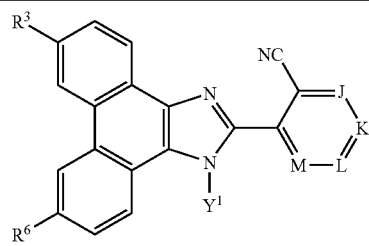

| Ex | R³/R⁶ | R⁶/R³ | J | K | L | M | Y¹ | (M + H)* |
|---|---|---|---|---|---|---|---|---|
| 40 | H₃C-C(OH)(CH₃)-C≡C-CH₃ | Cl | CH | CH | CH | CCN | H | 461 |
| 41 | Cl | H₃C-C(OH)(CH₃)-CH₃ | CH | CH | CH | CCN | H | 437 |
| 42 | H₃C-C(OH)(CH₃)-C≡C-CH₃ | I | CH | CH | CH | CCN | H | 553 |
| 43 | H₃C-C(OH)(CH₃)-C≡C-CH₃ | H₃C-C(OH)(CH₃)-C≡C-CH₃ | CH | CH | CH | CCN | H | 509 |
| 44 | H | H | CH | CH | CH | CCN | CO₂Et | 417 |
| 45 | H | H | CH | CH | CH | CCN | H₃C-CH₂-C(=O)-O-Et | 431 |
| 46 | H₃CO-CH₂-C≡C-CH₃ | Cl | CH | CH | CH | CCN | H | 447 |
| 47 | pyridin-3-yl-C≡C- | Cl | CH | CH | CH | CCN | H | 480 |
| 48 | 1-hydroxycyclopentyl-C≡C-CH₃ | Cl | CH | CH | CH | CCN | H | 487 |
| 49 | 1-methyl-imidazol-5-yl-C≡C-CH₃ | Cl | CH | CH | CH | CCN | H | 483 |
| 50 | 2-methyl-tetrazol-5-yl-CH₃ | Cl | CH | CH | CH | CCN | H | 461 |
| 51 | Cl | H₃C-CH(OH)-CH₃ | CH | CH | CH | CCN | H | 423 |
| 52 | cyclopropyl-C≡C-CH₃ | Cl | CH | CH | CH | CCN | H | 443 |

-continued

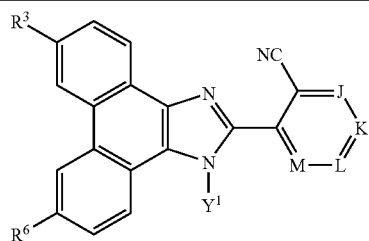

| Ex | R³/R⁶ | R⁶/R³ | J | K | L | M | Y¹ | (M + H)* |
|---|---|---|---|---|---|---|---|---|
| 53 | 2-pyridyl-C≡C- | Cl | CH | CH | CH | CCN | H | 480 |
| 54 | 4-pyridyl-C≡C- | Cl | CH | CH | CH | CCN | H | 480 |
| 55 | CH₃CH(OH)-C≡C-CH₃ | Cl | CH | CH | CH | CCN | H | 447 |
| 56 | CH₃C(O)-C≡C-CH₃ | Cl | CH | CH | CH | CCN | H | 445 |
| 57 | CH₃C(=NOH)-C≡C-CH₃ | Cl | CH | CH | CH | CCN | H | 460 |
| 58 | CH₃C(=NOCH₃)-C≡C-CH₃ | Cl | CH | CH | CH | CCN | H | 474 |
| 59 | H | H | CH | CH | CH | CCN | -CH₂C(O)CH₂CH₂C(O)OEt (HOOC-CH₂-CH₂-C(O)-O-Et) | 475 |
| 60 | H | H | CH | CH | CH | CCN | H₂PO₄CH₂ | — |
| 61 | 2-(5-methylpyridyl)-C(CH₃)₂OH | Cl | CH | CH | CH | CCN | H | 514 |
| 62 | Cl | SO₂CH₃ | CH | CH | CH | CCN | H | 457 |
| 63 | Cl | CH₃C(=NOH)CH₃ | CH | CH | CH | CCN | H | 436 |
| 64 | Br | H | CH | CH | CH | CCN | H | 425 |
| 65 | Cl | 4-CH₃-C₆H₄-S(O)₂-CH₃ | CH | CH | CH | CCN | H | 533 |

-continued

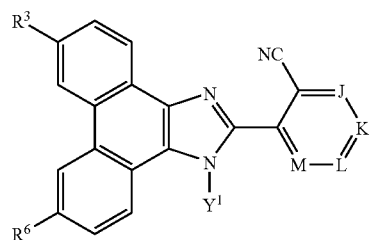

| Ex | R³/R⁶ | R⁶/R³ | J | K | L | M | Y¹ | (M + H)* |
|---|---|---|---|---|---|---|---|---|
| 66 | I | H | CH | CH | CH | CCN | H | 471 |
| 67 | CN | H | CH | CH | CH | CCN | H | 370 |
| 68 | cyclopropyl | Cl | CH | CH | CH | CCN | H | 418 |
| 69 | H₃C–C(OH)(CH₃)–C≡C–CH₃ | cyclopropyl–C≡C– | CH | CH | CH | CCN | H | 491 |
| 70 | Cl | F | CH | CH | CH | CCN | H | 397 |
| 71 | Cl | cyclopropyl–C(=O)– | CH | CH | CH | CCN | H | 447 |
| 72 | Cl | 4-Cl-C₆H₄-SO₂– | CH | CH | CH | CCN | H | 553 |
| 73 | vinyl | H | CH | CH | CH | CCN | H | 371 |
| 74 | ethyl | H | CH | CH | CH | CCN | H | 373 |
| 75 | cyclopropyl | H | CH | CH | CH | CCN | H | 385 |
| 76 | Cl | F₃C-S(O)- | CH | CH | CH | CBr | H | 549 |
| 77 | Cl | F₃C-S(O)- | CH | CH | CH | CCN | H | 495 |
| 78 | Cl | SO₂CF₃ | CH | CH | CH | CCN | H | 511 |
| 79 | cyclopropyl–C≡C– | H | CH | CH | CH | CCN | H | 409 |
| 80 | Cl | 4-(HO(CH₃)₂C)–C₆H₄– | CH | CH | CH | CCN | H | 513 |
| 81 | H₃C–C(OH)(CH₃)–C≡C–CH₃ | Br | CH | CH | CH | CCN | H | — |
| 82 | Cl | (F₃C)(HO)(H₃C)C– | CH | CH | CH | CCN | H | 491 |
| 83 | cyclopropyl–C≡C– | cyclopropyl–C≡C– | CH | CH | CH | CCN | H | 473 |

-continued

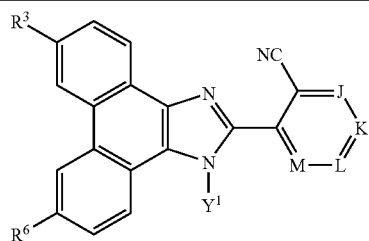

| Ex | R³/R⁶ | R⁶/R³ | J | K | L | M | Y¹ | (M + H)* |
|---|---|---|---|---|---|---|---|---|
| 84 | cyclopropyl-C≡C- | H₃C-S(O)₂-(4-tolyl) | CH | CH | CH | CCN | H | 563 |
| 85 | dicyclopropyl(OH)C-C≡C-CH₃ | Cl | CH | CH | CH | CCN | H | 513 |
| 86 | (H₃C-CH₂)₂C(OH)-C≡C-CH₃ | Cl | CH | CH | CH | CCN | H | 489 |
| 87 | Br | (H₃C)₂C(OH)- | CH | CH | CH | CCN | H | 481 |
| 88 | cyclopropyl-C≡C- | (H₃C)₂C(OH)- | CH | CH | CH | CCN | H | 467 |
| 89 | cyclopropyl-C≡C- | CN | CH | CH | CH | CCN | H | 434 |
| 90 | cyclopropyl-C≡C- | CO₂CH₃ | CH | CH | CH | CCN | H | 467 |
| 91 | 4-morpholinyl-(5-methylpyridin-2-yl) | Cl | CH | CH | CH | CCN | H | 541 |
| 92 | Cl | CN | CH | CH | CH | CCN | H | 404 |
| 93 | Cl | 3-(2-hydroxypropan-2-yl)tolyl | CH | CH | CH | CCN | H | 513 |
| 94 | Br | 2-(2-hydroxypropan-2-yl)pyridinyl | CH | CH | CH | CCN | H | 546 |
| 95 | (pyridine-N-oxide-4-yl)-C≡C-CH₃ | Cl | CH | CH | CH | CCN | H | 496 |

-continued

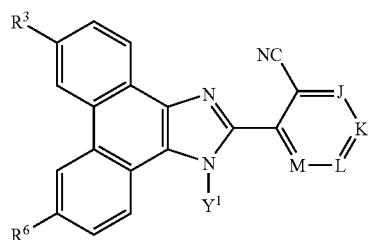

| Ex | R³/R⁶ | R⁶/R³ | J | K | L | M | Y¹ | (M + H)* |
|---|---|---|---|---|---|---|---|---|
| 96 | pyridin-3-yl-ethynyl | HO-C(CH₃)₂- | CH | CH | CH | CCN | H | 504 |
| 97 | 1-(pyrrol-1-yl)-1,1-dimethyl-propyn-2-yl | Cl | CH | CH | CH | CCN | H | 510 |
| 98 | HO-C(CH₃)₂-C≡C- | Br | CH | CH | CH | CCl | H | 514 |
| 99 | 4-hydroxy-4-(propyn-1-yl)-tetrahydropyran | Br | CH | CH | CH | CCl | H | 557 |
| 100 | Cl | CO₂i-Pr | CH | CH | CH | CCN | H | 465 |
| 101 | Cl | (H₃CO)₂C(CH₃)- | CH | CH | CH | CF | H | 460 |
| 102 | 4-hydroxy-4-(propyn-1-yl)-tetrahydropyran | Br | CH | CH | CH | CCN | H | 547 |
| 103 | 2-methyl-pyridin-5-yl | Cl | CH | CH | CH | CCN | H | 470 |
| 104 | Br | H₃C-C(O)- | CH | CH | CH | CCN | H | 465 |
| 105 | HO-C(CH₃)(p-tolyl)- | Cl | CH | CH | CH | CCl | H | 522 |
| 106 | Br | (H₃CO)₂C(CH₃)- | CH | CH | CH | CCN | H | 511 |
| 107 | 4-hydroxy-4-(propyn-1-yl)-tetrahydropyran | Cl | CH | CH | CH | CCl | H | 512 |

-continued

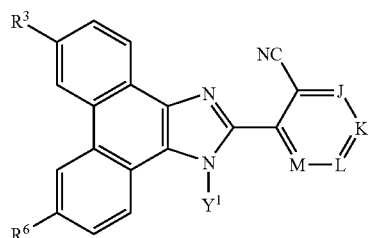

| Ex | R³/R⁶ | R⁶/R³ | J | K | L | M | Y¹ | (M + H)* |
|---|---|---|---|---|---|---|---|---|
| 108 | 3-(prop-1-ynyl)pyridine N-oxide | Cl | CH | CH | CH | CCN | H | 496 |
| 109 | 2-methylpentan-2-ol | Br | CH | CH | CH | CCN | H | 510 |
| 110 | 2-methylbut-3-yn-2-ol | Cl | CH | CH | CH | CCl | H | 470 |
| 111 | 2-methylbut-3-yn-2-ol | cyclopentylacetylene | CH | CH | CH | CCN | H | 519 |
| 112 | 3,5-dimethyl-1,2,4-oxadiazole | Br | CH | CH | CH | CCN | H | 504 |
| 113 | 3-(prop-1-ynyl)pyridine | 3-(prop-1-ynyl)pyridine | CH | CH | CH | CCN | H | 547 |
| 114 | Et | 2-methylbut-3-yn-2-ol | CH | CH | CH | CCN | H | 455 |
| 115 | 2-methylpentan-2-ol | cyclopropylacetylene | CH | CH | CH | CCN | H | 495 |
| 116 | Br | 3-methylpentan-3-ol | CH | CH | CH | CCN | H | 509 |
| 117 | 2-methylpentan-2-ol | Cl | CH | CH | CH | CCN | H | — |
| 118 | Br | CH₃ | CH | CH | CH | CCN | H | 438 |

-continued

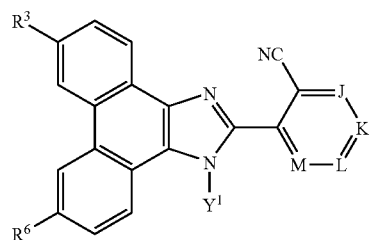

| Ex | R³/R⁶ | R⁶/R³ | J | K | L | M | Y¹ | (M + H)* |
|---|---|---|---|---|---|---|---|---|
| 119 | H₃C—C(OH)(CH₃)—C≡C—CH₃ | CH₃ | CH | CH | CH | CCN | H | 441 |
| 120 | H₃C—C(OH)(CH₃)—CH₂CH₂CH₃ | CH₃ | CH | CH | CH | CCN | H | 445 |
| 121 | H₃CO—C(O)—CH=CH—CH₃ | Cl | CH | CH | CH | CCN | H | 463 |
| 122 | H₃C—C(OH)(CH₃)—CH₂CH₂CH₃ | H | CH | CH | CH | CCN | H | 431 |
| 123 | H₃C—C(OH)(CH₂OH)—C≡C—CH₃ | Cl | CH | CH | CH | CCN | H | 477 |
| 124 | H₃CO—C(O)—CH₂—C(CH₃)₂—CH₂CH₂CH₃ | Cl | CH | CH | CH | CCN | H | 521 |
| 125 | HO—C(O)—CH₂—C(CH₃)₂—CH₂CH₂CH₃ | Cl | CH | CH | CH | CCN | H | 507 |
| 126 | HO—C(O)—cyclopropyl-CH₃ | Cl | CH | CH | CH | CCN | H | 463 |
| 127 | H₃C—C(O)—CH₂CH₃ | Cl | CH | CH | CH | CCN | H | 435 |
| 128 | H₃C—C(CH₃)(CH₂CH₃)—O—C(O)—CF₃ | Cl | CH | CH | CH | CCN | H | 547 |
| 129 | 1-propyl-cyclobutanol | Cl | CH | CH | CH | CCN | H | 477 |

-continued

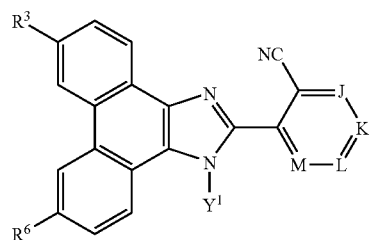

| Ex | R³/R⁶ | R⁶/R³ | J | K | L | M | Y¹ | (M + H)* |
|---|---|---|---|---|---|---|---|---|
| 130 | HO-C(CH₃)(OH)-propyl | Cl | CH | CH | CH | CCN | H | 481 |
| 131 | (CH₃)₂C(OH)-C≡C-CH₃ | Cl | CH | F | CH | CCN | H | 479 |
| 132 | H₃C-O-C(=O)- | H₃C-O-C(=O)- | CH | CH | CH | CCN | H | 461 |
| 133 | H₃C-O-C(=O)- | (CH₃)₂C(OH)- | CH | CH | CH | CCN | H | 461 |
| 134 | (CH₃)₂C(OH)- | (CH₃)₂C(OH)- | CH | CH | CH | CCN | H | 461 |
| 135 | (CH₃)(C₂H₅)C(OH)- | Cl | CH | CH | CH | CCN | H | 451 |
| 136 | Br | Cl | CH | OH | CH | CCN | H | 474 |
| 137 | (CH₃)₂C(OH)-C≡C-CH₃ | Cl | CH | OH | CH | CCN | H | 477 |
| 138 | CH₃CH(OAc)- | CH₃CH(OAc)- | CH | CH | CH | CCN | H | 517 |
| 139 | CH₃CH₂-O-C(=O)- | CH₃CH₂-O-C(=O)- | CH | CH | CH | CCN | H | 489 |
| 140 | 2-[C(CH₃)₂OH]-phenyl-propyl | 2-[C(CH₃)₂OH]-phenyl-propyl | CH | CH | CH | CCN | H | M − H: 667 |
| 141 | 2-[C(CH₃)₂OH]-phenyl-propyl | Br | CH | CH | CH | CCN | H | 585 |

-continued

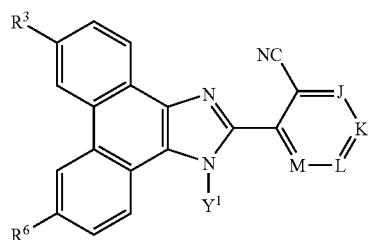

| Ex | R³/R⁶ | R⁶/R³ | J | K | L | M | Y¹ | (M + H)* |
|---|---|---|---|---|---|---|---|---|
| 142 | H₃C-C(CH₃)(OH)-C≡C-CH₃ | Cl | CH | Cl | CH | CCN | H | 495 |
| 143 | H₃C-CH₂-CH₂- | H₃C-CH₂- | CH | CH | CH | CCN | H | 401 |
| 144 | H₃C-C(OH)(CH₃)-C(=O)-CH₃ | Cl | CH | CH | CH | CCN | H | 465 |
| 145 | Br | (CH₃)₃C- | CH | CH | CH | CCN | H | 479 |
| 146 | H₃C-CH₂-CH₂- | (CH₃)₂C(OH)- | CH | CH | CH | CCN | H | 431 |
| 147 | H₃C-C(CH₃)(OH)-C≡C-CH₃ | (CH₃)₃C- | CH | CH | CH | CCN | H | 483 |
| 148 | H₃C-(CH₂)₃-CH₂- | (CH₃)₂C(OH)- | CH | CH | CH | CCN | H | 459 |
| 149 | H₃C-C(=O)-CH₂-CH₃ | H₃C-C(=O)-CH₂-CH₃ | CH | CH | CH | CCN | H | 457 |
| 150 | H₃C-CH(CH₃)-C(=O)-CH₃ | Cl | CH | F | CH | CCN | H | 467 |
| 151 | H₃C-C(OH)(CH₃)-C(=O)-CH₃ | Cl | CH | F | CH | CCN | H | 483 |
| 152 | HO-C(CH₃)(CH₃)-CH₂-CH₃ | Cl | CH | F | CH | CCN | H | 469 |

-continued

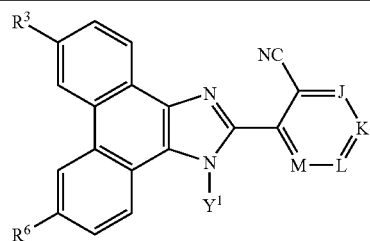

| Ex | R³/R⁶ | R⁶/R³ | J | K | L | M | Y¹ | (M + H)* |
|---|---|---|---|---|---|---|---|---|
| 153 | cyclopropylpropyl | 2-hydroxypropan-2-yl (H₃C, H₃C, OH) | CH | CH | CH | CCN | H | 471 |
| 154 | 1-hydroxycyclopentyl-propyl | Cl | CH | CH | CH | CCN | H | 491 |
| 155 | 4-(pyridin-4-yl)propyl | Cl | CH | CH | CH | CCN | H | 484 |
| 156 | Br | H₃CO— | CH | CH | CH | CCN | H | 454 |
| 157 | 2-methyl-2-hydroxy-pent-3-ynyl | H₃CO— | CH | CH | CH | CCN | H | 457 |
| 158 | 2-methylhex-1-en-3-ynyl | Cl | CH | CH | CH | CCN | H | — |
| 159 | 3-(pyridin-3-yl)propyl | 3-(pyridin-3-yl)propyl | CH | CH | CH | CCN | H | 555 |
| 160 | 2-methyl-2-hydroxy-pent-3-ynyl | cyclopropylmethoxy | CH | CH | CH | CCN | H | 497 |
| 161 | 3-(pyridin-3-yl)propyl | 2-hydroxypropan-2-yl | CH | CH | CH | CCN | H | 508 |
| 162 | 2-methyl-2-(pyrrol-1-yl)pentyl | Cl | CH | CH | CH | CCN | H | 514 |
| 163 | 2-hydroxy-2-methylbutyl | cyclopropyl | CH | CH | CH | CCN | H | 457 |
| 164 | 3-(1-methylimidazol-5-yl)propyl | Cl | CH | CH | CH | CCN | H | 487 |

-continued

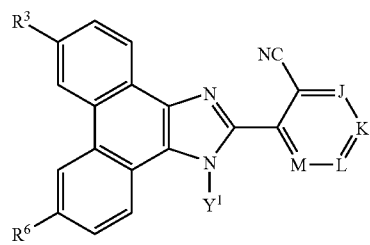

| Ex | R³/R⁶ | R⁶/R³ | J | K | L | M | Y¹ | (M + H)* |
|---|---|---|---|---|---|---|---|---|
| 165 | H₃C-N(CH₃)-CH₂-C≡C- | Cl | CH | CH | CH | CCN | H | 460 |
| 166 | H₃C-N(CH₃)-CH₂CH₂CH₂- | Cl | CH | CH | CH | CCN | H | 464 |
| 167 | H₃C-O-CH₂CH₂CH₂- | Cl | CH | CH | CH | CCN | H | 451 |
| 168 | HO-C(CH₃)(C₂H₅)- | cyclopropyl-CH₂-O- | CH | CH | CH | CCN | H | 487 |
| 169 | cyclopropyl-CH₂-O- | HO-C(CH₃)(C₂H₅)- | CH | F | CH | CCN | H | 505 |
| 170 | H₃C-N(CH₃)-C(O)-CH=CH- | Cl | CH | CH | CH | CCN | H | 476 |
| 171 | H₃C-C(OH)(CH₃)-CH₂CH₂CH₂- | Cl | CH | CH | CH | CCN | H | 479 |
| 172 | HO-C(CH₃)(C₂H₅)- | cyclopropyl-CH₂CH₂-O- | CH | F | CH | CCN | H | 519 |
| 173 | Br | HO-C(CH₃)₂-C₂H₅ | CH | CH | CH | CCN | H | 495 |
| 174 | HO-C(CH₃)(C₂H₅)- | cyclopropyl-O- | CH | CH | CH | CCN | H | 473 |
| 175 | HO-C(CH₃)(C₂H₅)- | cyclopropyl-O- | CH | F | CH | CCN | H | 491 |
| 176 | HO-C(CH₃)(C₂H₅)- | cyclopropyl-CH(CH₃)-O- | CH | CH | CH | CCN | H | 501 |

-continued

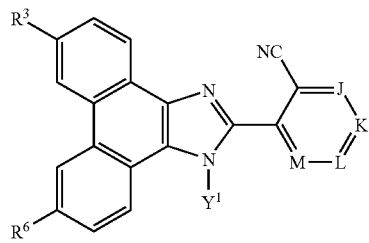

| Ex | R³/R⁶ | R⁶/R³ | J | K | L | M | Y¹ | (M + H)* |
|---|---|---|---|---|---|---|---|---|
| 177 | HO-C(CH₃)(C₂H₅)- | cyclopropyl-CH(OCH₃)- | CH | F | CH | CCN | H | 519 |
| 178 | OH | Cl | CH | CH | CH | CCN | H | 395 |
| 179 | Cl | CH₃C(O)OCH₂- (methyl acetate group) | CH | CH | CH | CCN | H | 437 |
| 180 | HO-C(CH₃)(C₂H₅)- | CF₃CH₂CH₂CH₂OCH₂- | CH | CH | CH | CCN | H | 543 |
| 181 | Cl | CH₃CH(OH)CH₂C≡CH | CH | CH | CH | CCN | H | 461 |
| 182 | HO-C(CH₃)(C₂H₅)- | cyclopropyl-CH₂CH₂OCH₃ | CH | CH | CH | CCN | H | 501 |
| 183 | CH₃CH₂CH₂C(O)OCH₃ | Cl | CH | CH | CH | CCN | H | 465 |
| 184 | Cl | CH₃OC(CH₃)₂C(O)OCH₃ | CH | CH | CH | CCN | H | 495 |
| 185 | Cl | (CH₃)₃CC(O)OCH₃ | CH | CH | CH | CCN | H | 479 |
| 186 | cyclopropyl-C(O)OCH₃ | Cl | CH | CH | CH | CCN | H | 463 |
| 187 | Br | Cl | CH | CH(OCH₃) | CH | CCN | H | 487 |
| 188 | cyclopropyl-CH₂CH₂OCH₃ | HOC(CH₃)(C≡CCH₃) | CH | CF | CH | CCN | H | 529 |
| 189 | Cl | Br | CH | N | CH | CCN | H | 459 |

-continued

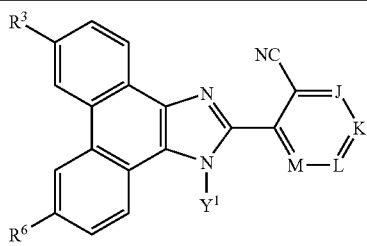

| Ex | R³/R⁶ | R⁶/R³ | J | K | L | M | Y¹ | (M + H)* |
|---|---|---|---|---|---|---|---|---|
| 190 | H₃C—C(OH)(CH₃)—C≡C— | Cl | CH | N | CH | CCN | H | 462 |

[Second structure: phenanthro-imidazole with R3, R6, R7 substituents and a 2,6-dicyanophenyl group]

| EX | R3 | R6 | R7 | (M + H)* |
|---|---|---|---|---|
| 191 | H₃C—C(OH)(CH₃)—C≡C— | Cl | H—C(H)(H)—H | 475 |
| 192 | Cl | H | Br | 459 |
| 193 | Cl | H | H₃C—C(OH)(CH₃)—C≡C— | 461 |
| 194 | Cl | H | H₃C—C(OH)(CH₃)—CH₂CH₃ | 465 |

The invention includes, as appropriate, pharmaceutically acceptable salts of any of the aforementioned compounds. For purposes of this specification, the heading "R³/R⁶" means that the substituent indicated in that column is substituted at the position represented by either R³ or R⁶. In the adjacent column, the heading "R⁶/R³" means the indicated substituent is substituted at the position R³ or R⁶ not substituted in the previous column. By way of example, Example 6 represents R³=CN and R⁶=H or R³=H and R⁶=CN, representing both tautomers.

The term "halogen" or "halo" includes F, Cl, Br, and I.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl and 1,1-dimethylethyl.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. $C_{3-6}$alkynyl, for example, includes, propenyl, 1-methylethenyl, butenyl and the like.

The term "alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

The term "cycloalkyl" means mono-, bi- or tri-cyclic structures, optionally combined with linear or branched structures, having the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, cyclobutylmethyl cyclopropylmethyl and the like.

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

Some of the compounds described herein contain olefinic double bonds, and unless specified otherwise, are meant to include both E and Z geometric isomers.

Some of the compounds described herein may exist with different points of attachment of hydrogen, referred to as tautomers. The compound of Formula I exists in the following tautomeric forms:

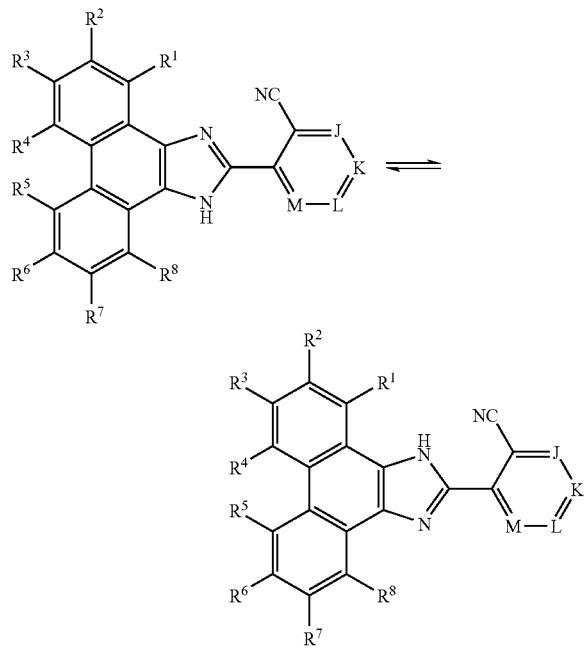

The individual tautomers as well as mixture thereof are encompassed within Formula I.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu. Exemplifying prodrugs of the invention are compounds of Formula C.

The term "treating a microsomal prostaglandin E synthase-1 mediated disease or condition" means treating or preventing any disease or condition that is advantageously treated or prevented by inhibiting the microsomal prostaglandin E synthase-1 (mPGES-1) enzyme. The term includes the relief of pain, fever and inflammation of a variety of conditions including rheumatic fever, symptoms associated with influenza or other viral infections, common cold, low back and neck pain, dysmenorrhea, headache, migraine (acute and prophylacetic treatment), toothache, sprains and strains, myositis, neuralgia, synovitis, arthritis, including rheumatoid arthritis, degenerative joint diseases (osteoarthritis), gout and ankylosing spondylitis, acute, subacute and chronic musculoskeletal pain syndromes such as bursitis, burns, injuries, and pain following surgical and dental procedures as well as the preemptive treatment of surgical pain. In addition, the term includes the inhibition cellular neoplastic transformations and metastic tumor growth and hence the treatment of cancer. The term also includes the treatment of endometriosis and Parkinson's disease as well as the treatment of mPGES-1 mediated proliferative disorders such as may occur in diabetic retinopathy and tumor angiogenesis. The term "treating" encompasses not only treating a patient to relieve the patient of the signs and symptoms of the disease or condition but also prophylactically treating an asymptomatic patient to prevent the onset or progression of the disease or condition.

The term "amounts that are effective to treat" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician. Suitable dosage levels of the compound of Formula I used in the present invention are described below. The compound may be administered on a regimen of once or twice per day.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" include salts prepared from bases that result in non-toxic pharmaceutically acceptable salts, including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from acids that result in pharmaceutically acceptable salts, including inorganic and organic acids. Such acids include acetic, adipic, aspartic, 1,5-naphthalenedisulfonic, benzenesulfonic, benzoic, camphorsulfonic, citric, 1,2-ethanedisulfonic, ethanesulfonic, ethylenediaminetetraacetic, fumaric, glucoheptonic, gluconic, glutamic, hydriodic, hydrobromic, hydrochloric, isethionic, lacetic, maleic, malic, mandelic, methanesulfonic, mucic, 2-naphthalenesulfonic, nitric, oxalic, pamoic, pantothenic, phosphoric, pivalic, propionic, salicylic, stearic, succinic, sulfuric, tartaric, p-toluenesulfonic acid, undecanoic, 10-undecenoic, and the like.

By virtue of the mPGES-1 inhibitory activity of compounds of the present invention, the compounds of Formula I are useful for the relief of pain, fever and inflammation of a variety of conditions including rheumatic fever, symptoms associated with influenza or other viral infections, common cold, low back and neck pain, dysmenorrhea, headache, migraine (acute and prophylacetic treatment), toothache, sprains and strains, myositis, neuralgia, synovitis, arthritis, including rheumatoid arthritis, juvenile rheumatoid arthritis, degenerative joint diseases (osteoarthritis), acute gout and ankylosing spondylitis, acute, subacute and chronic musculoskeletal pain syndromes such as bursitis, burns, injuries, and pain following surgical and dental procedures as well as the preemptive treatment of surgical pain. In addition, such a compound may inhibit cellular neoplastic transformations and metastic tumor growth and hence can be used in the treatment of cancer. Compounds of Formula I may also be useful for the treatment or prevention of endometriosis, hemophilic arthropathy and Parkinson's disease.

Compounds of Formula I will also inhibit prostanoid-induced smooth muscle contraction by preventing the synthesis of contractile prostanoids and hence may be of use in the treatment of dysmenorrhea, premature labor and asthma.

By virtue of their selective inhibition of the mPGES-1 enzyme, the compounds of Formula I will prove useful as an alternative to conventional non-steroidal antiinflammatory drugs (NSAID'S) particularly where such non-steroidal anti-inflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems (including those relating to reduced or impaired platelet function); kidney disease (e.g., impaired renal function); those prior to surgery or taking anticoagulants; and those susceptible to NSAID induced asthma.

Similarly, compounds of Formula I will be useful as a partial or complete substitute for conventional NSAIDs in preparations wherein they are presently co-administered with other agents or ingredients. Thus in further aspects, the invention encompasses pharmaceutical compositions for treating mPGES-1 mediated diseases as defined above comprising a non-toxic therapeutically effective amount of the compound of Formula I as defined above and one or more ingredients such as another pain reliever including acetaminophen or phenacetin; opioid analgesics, such as codeine, fentanyl, hydromorphone, levorphanol, meperidine, methadone, morphine, oxycodone, oxymorphone, propoxyphene, buprenorphine, butorphanol, dezocine, nalbuphine and pentazocine; a potentiator including caffeine; an H2-antagonist; aluminum or magnesium hydroxide; simethicone; a decongestant including phenylephrine, phenylpropanolamine, pseudophedrine, oxymetazoline, ephinephrine, naphazoline, xylometazoline, propylhexedrine, or levo-desoxyephedrine; an anti-tussive including codeine, hydrocodone, caramiphen, carbetapentane, or dextramethorphan; a diuretic; a sedating or non-sedating antihistamine; a proton pump inhibitor, such as omeprazole; a bradykinin-1 antagonist; a VR1 receptor antagonist; and a sodium channel blocker (NAV1). For the treatment or prevention of migraine, the invention also encompasses co-administration with a 5-HT agonist such as rizatriptan, sumatriptan, zolmitriptan and naratriptan, or a CGRP antagonist. In addition the invention encompasses a method of treating mPGES-1 mediated diseases comprising: administration to a patient in need of such treatment a non-toxic therapeutically effect amount of the compound of Formula I, optionally co-administered with one or more of such ingredients as listed immediately above.

As indicated above, pharmaceutical compositions for treating mPGES-1 mediated diseases as defined may optionally include one or more ingredients as listed above.

In another aspect, the invention encompasses co-administering a proton pump inhibitor with a compound of Formula I. The proton pump inhibitors that may be utilized in this aspect of the invention include omeprazole, lansoprazole, rabeprazole, pantoprazole, and esomeprazole, or a pharmaceutically acceptable salt of any of the aforementioned. These proton pump inhibitors are commercially available, e.g., omeprazole (PRILOSEC, AstraZeneca), lansoprazole (PREVACID, TAP Pharmaceuticals), rabeprazole (ACIPHEX, Janssen Pharmaceutica), pantoprazole (PROTONIX, Wyeth-Ayerst), and esomeprazole (NEXIUM, AstraZeneca). The said proton pump inhibitors may be administered at conventional doses. For example, omeprazole or omeprazole magnesium may be administered at a dose of 10 mg, 20 mg or 40 mg. Lansoprazole may be administered at a dose of 15 mg or 30 mg. Rabeprazole sodium may be administered at a dose of 20 mg. Pantoprazole may be administered at a dose of 20 mg or 40 mg. Esomeprazole may be administered at a dose of 20 mg or 40 mg. The compound of Formula I and the proton pump inhibitor may be administered concomitantly in a single pharmaceutical dosage form or as two separate dosage forms taken by a patient substantially at the same time. Alternatively, the compound of Formula I and the proton pump inhibitor may be taken sequentially at separately staggered times as long as the pharmaceutical effects of the two agents are being realized by the patient at the same time.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil. Exemplifying a formulation for the present invention is a dry filled capsule containing a 50/50 blend of microcrystalline cellulose and lactose and 1 mg, 10 mg or 100 mg of the compound of Formula I.

Aqueous suspensions contain the active material in admixture with excipients suitable for the manufacture of aqueous suspensions. Such excipients are suspending agents, for example sodium carboxymethyl-cellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Liquid formulations include the use of self-emulsyfying drug delivery systems and NanoCrystal® technology. Cyclodextrin inclusion complexes can also be utilized.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Pharmaceutical compositions of the invention may also utilize absorption enhancers such as tween 80, tween 20, Vitamin E TPGS (d-alpha-tocopheryl polyethylene glycol 1000 succinate) and Gelucire®.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day, preferably 2.5 mg to 1 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg. Dosage amounts of 4 mg, 8 mg, 18 mg, 20 mg, 36 mg, 40 mg, 80 mg, 160 mg, 320 mg and 640 mg may also be employed. Dosage unit forms containing 1, 10 or 100 mg are also encompassed.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Methods of Synthesis

The compounds of Formula I of the present invention can be prepared according to the synthetic routes outlined in Schemes 1 and 4 below and by following the methods described therein. The imidazole of Formula I may be prepared in a multi-step sequence from the requisite phenanthrenequinone i. The phenanthrene imidazole iii is obtained by treating the phenanthrenequinone i and an appropriately substituted aldehyde ii with a reagent such as $NH_4OAc$ or $NH_4HCO_3$ in a solvent such as acetic acid. Treatment of the imidazole iii with CuCN in a solvent such as DMF or DMSO produces the mono or bis-nitrile (M=CCN) Ia. Subsequent functional group interconversion can be done at any of the $R^1$ to $R^8$ positions. For example, if one or more of the $R^1$ to $R^8$ substituents equal Cl, Br or I and if M is different from CBr or CI, Ia could be converted to Ib by placing Ia in the presence of a monosubstituted alkynyl, a stannane, a boronic acid, a borane or a boronate under conditions that promote cross coupling reaction, such as heating in the presence of a catalyst, such as $Pd(PPh_3)_4$ and CuI, in the presence of a base, such as sodium carbonate or diisopropylamine, and in an suitable solvent, such as THF, DMF or DME. This last exemplified step, or any other appropriate functional group transformation, can be iteratively repeated on $R^1$ to $R^8$.

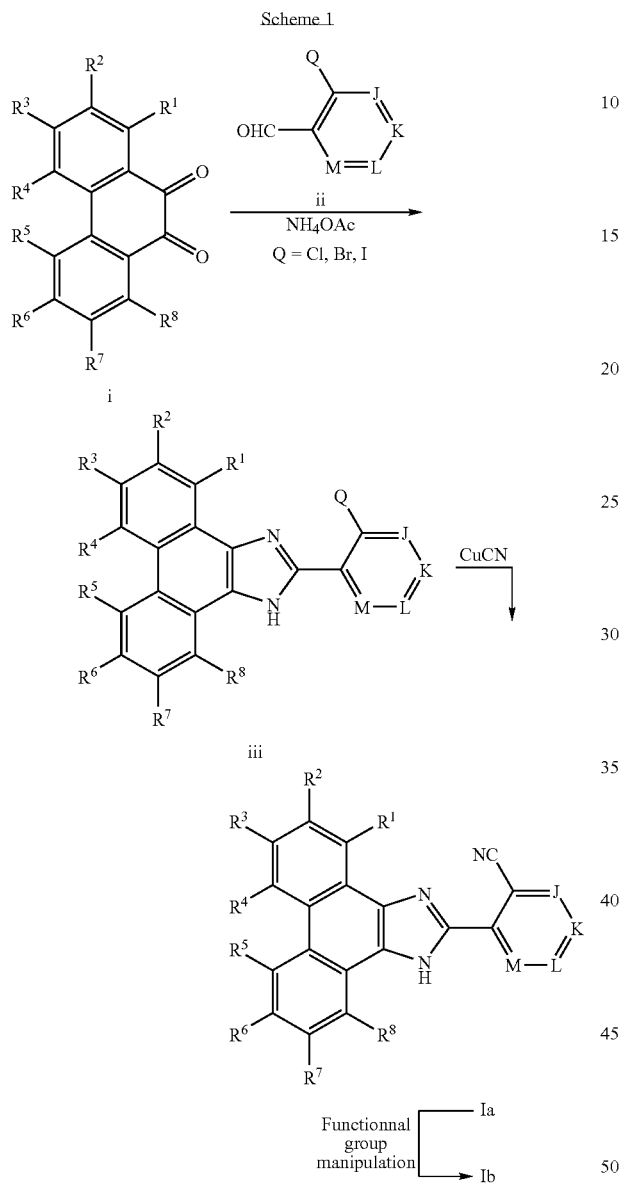

Phenanthrenequinone i can be prepared according to the sequences outlined in Scheme 2 and 3. Deprotonation of the phosphonium salt iv (Scheme 2) in the presence of a base, such as sodium hydride or sodium methoxide, in a solvent such as DMF followed by the addition of the aldehyde v produces the stylbene vi as a mixture of E and Z isomers. Intramolecular cyclisation of this mixture upon exposition to UV light in the presence of an oxidizing agent, such as iodine, and an acid scavenger, such as propylene oxide, in a suitable solvent such as cyclohexanne produces the phenanthrene vii. This phenanthrene viia can be directly oxidized with an oxidizing agent, such as $CrO_3$, in a suitable solvent, such as acetic acid, to provide the phenanthrenequinone i, or optionally, phenanthrene viia could be further elaborated to phenanthrene viib by the appropriate interconversion of any of the functional group $R^1$ to $R^8$, such as transmetallation with an organometallic reagent, such as butyl lithium, in a suitable solvent such as THF, followed by the addition of an electrophile, such as iodine or carbon dioxide. Alternatively (Scheme 3), phenylacetic acid viii can be condensed with the aldehyde ix in the presence of a base, such as potassium carbonate, and in the presence of acetic anhydride to afford the nitro stylbene x. This nitro aryl x is then reduced with an appropriate reducing agent, such as iron or iron sulfate, in the presence of ammonium hydroxide in a suitable solvent, such as acetic acid, to produce the amine xi. Diazotization of this amine xi with sodium nitrite in the presence of aqueous hydroxide, such as sodium hydroxide, followed by acidification with an acid, such as sulfuric acid and sulfamic acid, and cyclization in the presence of a catalyst, such as copper or a ferrocene, generates the phenanthrene carboxylic acid xii. This phenanthrene can be oxidized and simultaneously decarboxylated using an appropriate oxidizing agent, such as chromium trioxide in suitable solvent, such as acetic acid, to afford the phenanthrenequinone i.

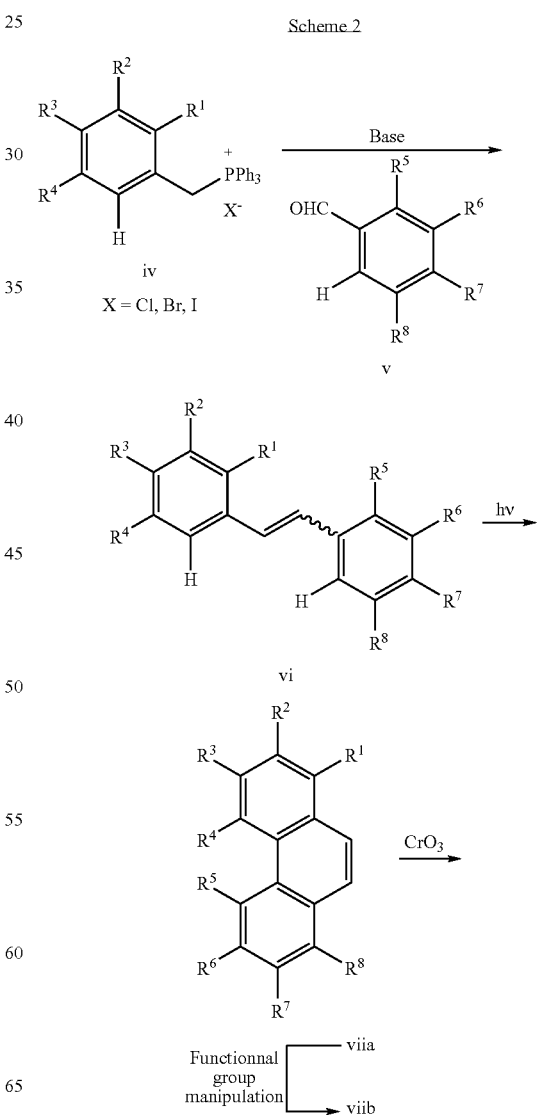

-continued

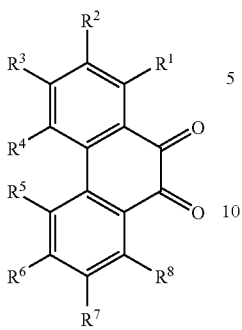

Scheme 3

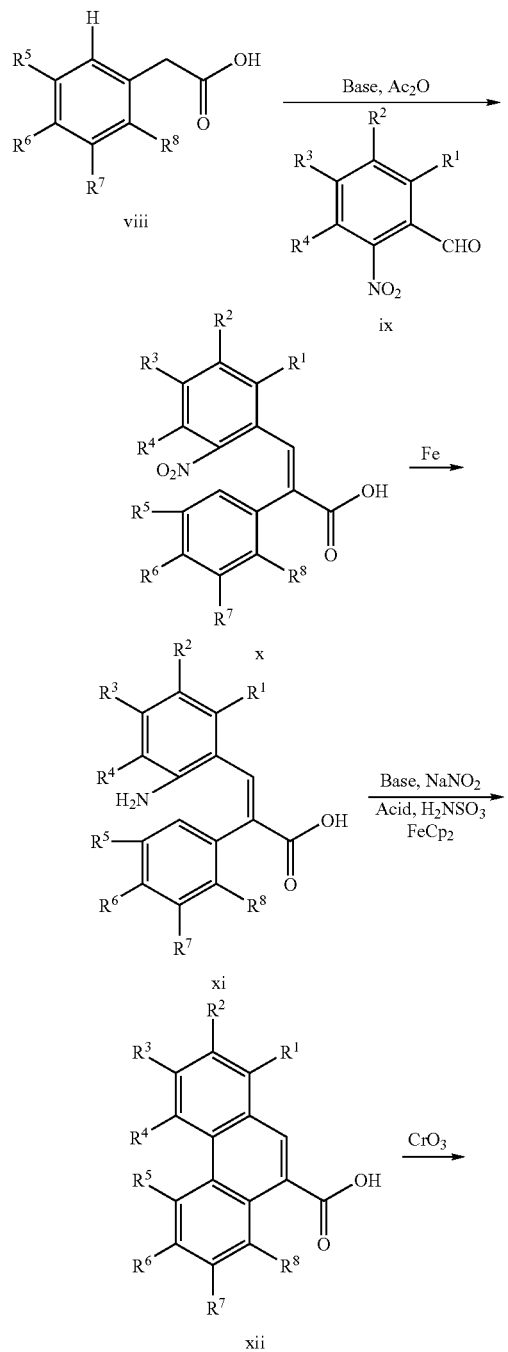

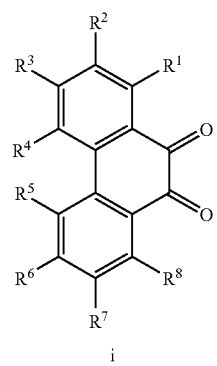

As shown in Scheme 4, protection of the halophenanthrene xiii with an appropriate protecting group such as 2-(trimethylsily)ethoxymethyl in the presence of a base, such as sodium hydride or diisopropylethylamine, in a suitable solvent, such as DMF or methylene chloride, affords the protected phenanthrene imidazole xiv. This phenanthrene imidazole xiv is then carbonylated with carbon monoxide in the presence of a catalyst, such as Pd(OAc)$_2$, and in the presence of a base, such as triethylamine, in a mixture of an alcoholic solvent, such as methanol and DMF, or any other suitable organic solvent. Treatment of the ester xv with a nucleophilic reagent such as an organolithium, organocerium or Grignard reagent in an organic solvent, such as ether, THF or methylene chloride (Grinard reagent), provides the tertiary alcohol xvi. Removal of the imidazole protecting group, for example by treating xvi with a mineral acid such as hydrochloric acid or in the presence of a fluoride source such as TBAF, in an organic solvent such as THF, affords the unprotected imidazole xvii. Treatment of this phenanthrene imidazole xvii with CuCN in a solvent, such as DMF or DMSO, produced the mono or bis-nitrile (M=CCN) Id. Subsequent functional group interconversion can be done at any of the $R^1$ to $R^8$ positions. For example, if one or more of the $R^1$ to $R^8$ substituents equal Cl, Br or I and if M is different from CBr or CI, Id could be converted to Ie by placing Id in the presence of a monosubstituted alkynyl, a stannane, a boronic acid, a borane or a boronate under conditions that promote cross coupling reaction, such as heating in the presence of a catalyst such as Pd(PPh$_3$)$_4$ and CuI, and in the presence of a base, such as sodium carbonate or diisopropylamine, in a suitable solvent, such as THF, DMF or DME. This last exemplified step, or any other appropriate functional group transformation, can be iteratively repeated on $R^1$ to $R^8$.

Scheme 4

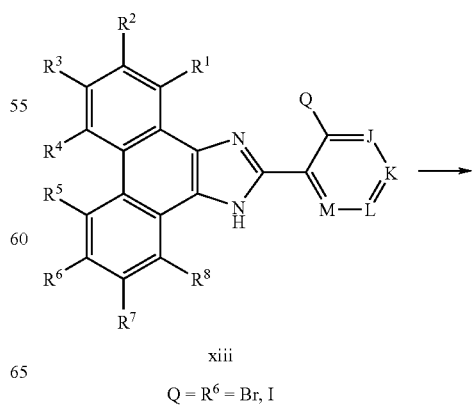

Q = $R^6$ = Br, I

-continued

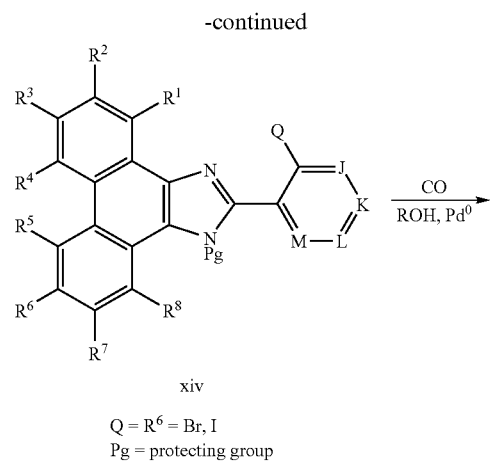

xiv

Q = R⁶ = Br, I
Pg = protecting group

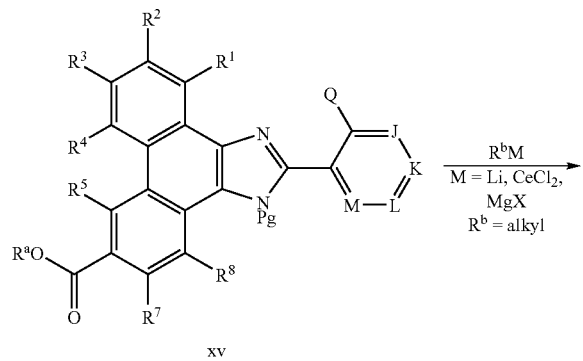

xv

Rᵃ = alkyl
Q = Br, I

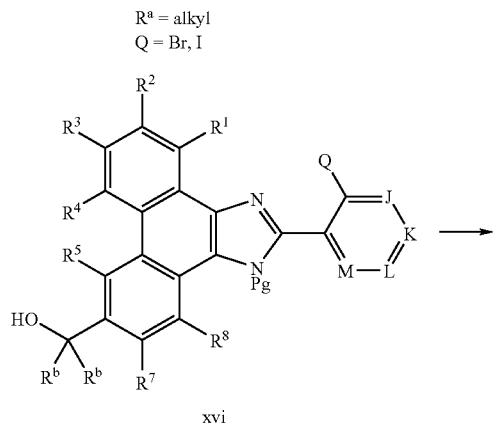

xvi

Q = Br, I

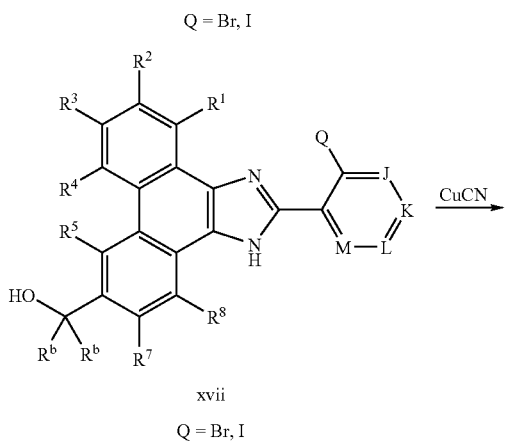

xvii

Q = Br, I

-continued

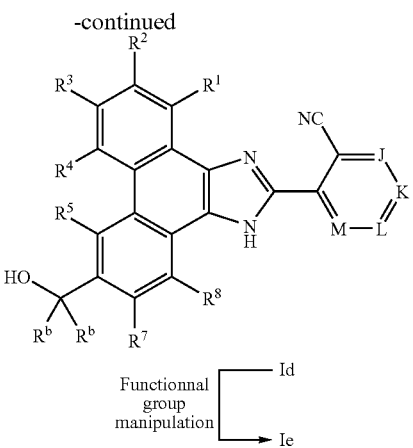

Functionnal group manipulation → Id
→ Ie

The imidazole secondary amine can be substituted as described in Scheme 5 by treating an appropriately functionalized phenanthrene imidazole I with a reagent such as an acylating agent or an alkylating agent such as methyl iodide in the presence of a base such as sodium hydride in a suitable solvent such as DMF.

Scheme 5

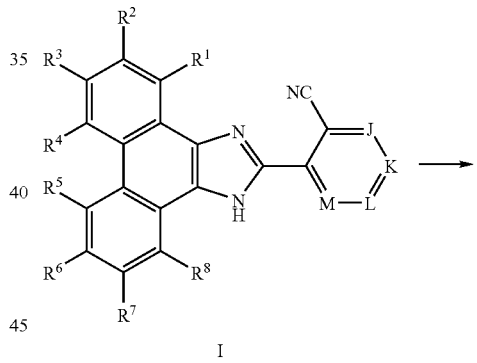

I

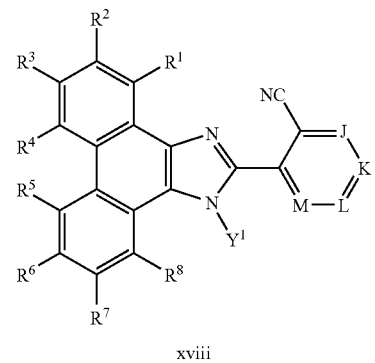

xviii

EXAMPLES

The invention is exemplified by the following non-limiting examples:

Example 14

2-[9-chloro-6-(3-hydroxy-3-methylbutyl-1-yn-1-yl)-1H-phenanthro[9,10-d]imidazol-2-yl]-3-fluorobenzonitrile

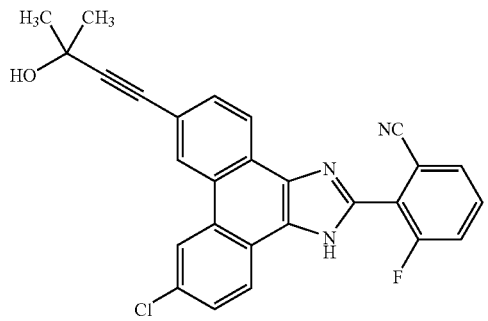

Step 1: 6,9-dibromo-2-(2-chloro-6-fluorophenyl)-1H-phenanthro[9,10-d]imidazole

To a solution of 30 g (82 mmol) of 3,6-dibromophenanthrene-9,10-dione (Bhatt, *Tetrahedron,* 1963, 20, 803) in 1.0 L of acetic acid was added 25.9 g (328 mmol) of $NH_4HCO_3$ followed by 26 g (164 mmol) of 2-fluoro-6-chlorobenzaldehyde. The solution was stirred overnight at 130° C., cooled down to room temperature and poured into 2.5 L of water. The mixture was filtered, washed with water followed by hexane and diethyl ether. The resulting solid was refluxed in 1.0 L of toluene with a Dean-stark apparatus and approx. 100 mL of water was removed over 3 hrs. Upon cooling down to room temperature, a beige solid crystallized out of solution. This solid was filtered, washed with toluene and pumped under reduced pressure to afford 32 g (80%) of 6,9-dibromo-2-(2-chloro-6-fluorophenyl)-1H-phenanthro[9,10-d]imidazole.

Step 2: 2-(6-bromo-9-chloro-1H-phenanthro[9,10-d]imidazol-2-yl)-3-fluorobenzonitrile To a DMF (10 mL) solution of 3.0 g 6,9-dibromo-2-(2-chloro-6-fluorophenyl)-1H-phenanthro[9,10-d]imidazole from Step 1, was added 587 mg of CuCN and the solution was stirred overnight at 130° C. The solution was cooled down to room temperature followed by the addition of aqueous ammonium hydroxide and ethyl acetate. Layers were separated and the organic layer was washed with brine, dried over sodium sulphate and volatiles were removed under reduced pressure. The residue was purified by flash chromatography on silica gel using a gradient of 30% to 50% ethyl acetate/hexane to afford 500 mg of 2-(6-bromo-9-chloro-1H-phenanthro[9,10-d]imidazol-2-yl)-3-fluorobenzonitrile.

Step 3: 2-[9-chloro-6-(3-hydroxy-3-methylbutyl-1-yn-1-yl)-1H-phenanthro[9,10-d]imidazol-2-yl]-3-fluorobenzonitrile To a DMF (2 mL) solution of 2-(6-bromo-9-chloro-1H-phenanthro[9,10-d]imidazol-2-yl)-3-fluorobenzonitrile (320 mg) from Step 2 was added 5 mL of triethylamine, 0.1 mL of 2-methyl-3-butyn-2-ol, 20 mg of CuI and 82 mg of Pd(PPh$_3$)$_4$. The resulting mixture was stirred overnight at 80° C., cooled down to room temperature and diluted with ethyl acetate/water. The organic layer washed with brine, dried over sodium sulphate and the volatiles were removed under reduced pressure. The residue was purified by flash chromatography on silica gel using a gradient of 30% to 50% ethyl acetate/hexane to afford 85 mg of 2-[9-chloro-6-(3-hydroxy-3-methylbutyl-1-yn-1-yl)-1H-phenanthro[9,10-d]imidazol-2-yl]-3-fluorobenzonitrile. $^1$H NMR (Acetone-d$_6$): δ 8.89 (s, 2H), 8.71 (bs, 1H), 8.51 (bs, 1H), 7.93 (d, 1H), 8.88-8.72 (m, 4H), 4.55 (s, 1H), 1.65 (s, 6H).

Example 25

2-(6-chloro-1H-phenanthro[9,10-d]imidazol-2-yl)isophthalonitrile

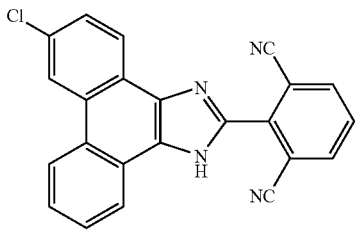

Step 1: 1-(3-phenanthryl)ethanone oxime

In 200 mL of absolute ethanol was combined a mixture of 50 g (0.23 mol) of 1-(3-phenanthryl)ethanone and 40 g of hydroxylamine hydrochloride. The solution was heated to reflux followed by the addition of 70 mL of pyridine. After 3 hrs, the reaction was cooled down to room temperature and the solution rotovaped down. A mixture of ice/water was added to the residue and the mixture was stirred for 1 hr. The resulting off-white solid was filtered, washed with water and air dried to afford, after recrystallization in diethyl ether, 32 g of 1-(3-phenanthryl)ethanone oxime.

Step 2: 3-phenanthrylamine

To 385 g of polyphosphoric acic at 100° C. was added 32 g (0.14 mol) of 1-(3-phenanthryl)ethanone oxime from Step 1 over 30 minutes. The mixture was stirred at 100° C. for 2 hrs, cooled down to room temperature followed by the addition of water/ice. Stirred 30 minutes, filtered and washed with water. This white solid was then placed in 500 mL of methanol and 40 mL of concentrated HCl. The reaction was refluxed overnight, cooled down to room temperature and concentrated down. A mixture of ethyl acetate/water was added to the residue and the resulting solution was made basic with 10 N KOH. The aqueous layer was extracted with ethyl acetate and combined organic layers were washed with water, brine, dried over sodium sulphate and volatiles were removed under reduced pressure to afford 25 g of 3-phenanthrylamine as a beige solid.

Step 3: 3-chlorophenanthrene

CuCl$_2$ (21 g) was dried under high vacuum at 115° C. for 90 minutes then cooled down to 65° C. followed by the addition of 250 mL of dry acetonitrile and 26 g of t-butyl nitrite. The 3-phenanthrylamine (25 g) from Step 2 was added over 30 minutes as a solution in 100 mL of acetonitrile. The reaction was stirred 45 minutes at 65° C., cooled down to room temperature followed by the addition of 1 L of 1 N HCl. The aqueous layer was extracted with methylene chloride and combined organic layers were washed with water, brine, dried over sodium sulphate and volatiles were removed under reduced pressure. The residue was purified by flash chromatography on silica gel using hexane as the eluent to afford a white solid which was recristallized from hexane to produce 14.4 g of 3-chlorophenanthrene as a white solid.

Step 4: 3-chlorophenanthrene-9,10-dione

To a solution of 12.5 g (58.7 mmol) of 3-chlorophenanthrene from Step 3 in 350 mL of acetic acid was added 23.5 g (0.23 mol) of CrO3. The reaction was stirred 2 hrs at 100° C., cooled down to room temperature and poured into 2 L of water. The suspension was stirred 1 hr, filtered and washed with water. The residue was dried under high vacuum to afford 12.5 g (88%) of 3-chlorophenanthrene-9,10-dione.

Step 5: 6-chloro-2-(2,6-dibromophenyl)-1H-phenanthro[9,10-d]imidazole

This imidazole was prepared by following the procedure describe in Example 14, Step 1, but substituting 3-chlorophenanthrene-9,10-dione for 3,6-dibromophenanthrene-9,10-dione and substituting 2,6-dibromobenzaldehyde for 2-fluoro-6-chlorobenzaldehyde to afford 27 g of 6-chloro-2-(2,6-dibromophenyl)-1H-phenanthro[9,10-d]imidazole as an off-white solid.

Step 6: 2-(6-chloro-1H-phenanthro[9,10-d]imidazol-2-yl)isophthalonitrile

To a DMF (300 mL) solution of 32 g (65.7 mmol) of 6-chloro-2-(2,6-dibromophenyl)-1H-phenanthro[9,10-d]imidazole from Step 5 was added 14.7 g of CuCN. The reaction was stirred overnight at 80° C., cooled down to room temperature, poured into a mixture of 1.5 L of water, 1.5 L of ethyl acetate and 200 mL of concentrated ammonium hydroxide and stirred 1 hr at room temperature. The aqueous layer was extracted with ethyl acetate and the combined organic layers were washed with 10% ammonium hydroxide, water, brine, dried over sodium sulphate and volatiles were removed under reduced pressure. The residue was swished in toluene (2×200 mL) and ethyl acetate (1 L). The obtained solid was purified by flash chromatography on silica gel in 5 portions using a gradient of 60% to 80% to 100% of ethyl acetate/hexane to afford 19.9 g of 2-(6-chloro-1H-phenanthro[9,10-d]imidazol-2-yl)isophthalonitrile as a pale yellow solid. $^1$H NMR (400 MHz, DMSO): δ 14.32 (s, 1H), 9.0-8.9 (m, 2H), 8.55-8.45 (m, 4H), 7.99 (t, 1H), 7.85-7.78 (m, 2H), 7.72 (t, 1H).

Example 36

2-(6-bromo-9-chloro-1H-phenanthro[9,10-d]imidazol-2-yl)isophthalonitrile

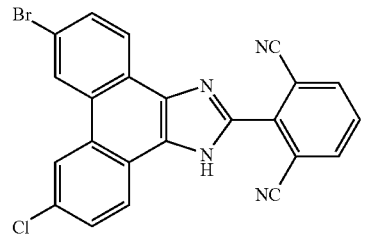

Step 1: 1-bromo-4-[2-(4-chlorophenyl)vinyl]benzene

To a solution of (4-bromobenzyl)triphenylphosphonium bromide (396 g; 0.77 mol) in 2.5 L of DMF at 0° C., was added 37 g (0.92 mol) of NaH (60% in oil) in four portions. The solution was stirred 1 hr at 0° C. followed by the addition of 109 g (0.77 mol) of 4-chlorobenzaldehyde in two portions. This mixture was warmed up to room temperature, stirred 1 hr and quench by pouring the reaction into a 5° C. mixture of 10 L of water and 2.5 L of Et$_2$O. Aqueous layer was extracted with Et$_2$O, combined organic layers were washed with brine and dried over Na$_2$SO$_4$. Volatiles were removed under reduced pressure and the residue was dissolved in 1.5 L of cyclohexane and filtered through a pad of silica gel (wash with cyclohexane). 16 g of one isomer cristallized out of the solution as a white solid and after evaporation of the volatiles, 166 g of the other isomer 1-bromo-4-[2-(4-chlorophenyl)vinyl]benzene was isolated.

Step 2: 3-bromo-6-chlorophenanthrene

A 2 L vessel equipped with a pyrex inner water-cooled jacket was charged with 5.16 g (17 mmol) of 1-bromo-4-[2-(4-chlorophenyl)vinyl]benzene from Step 1, 2 L of cyclohexane, 25 mL of THF, 25 mL of propylene oxide and 6.7 g (26 mmol) of iodine. The stirring solution was degassed by bubbling nitrogen and was exposed to UV light for 24 hrs by inserting a 450 W medium pressure mercury lamp in the inner. The reaction was quenched with 10% Na$_2$S$_2$O$_3$ and aqueous layer was extracted with ethyl acetate. Combined organic layers were washed with brine, dried over Na$_2$SO$_4$ and volatiles were removed under reduced pressure. The residue was swished in a minimal amount of ethyl acetate to afford approx. 5 g of 3-bromo-6-chlorophenanthrene as a solid.

Step 3: 3-Bromo-6-chlorophenanthrene-9,10-dione

To a solution of 3-bromo-6-chlorophenanthrene from Step 2 (1.71 g; 5.86 mmol) in 35 mL of acetic acid was added 2.3 g (23.5 mmol) of CrO$_3$. The mixture was stirred 2 hrs at 100° C., cooled down to room temperature, poured into 300 mL of water and stirred for 1 hr. The suspension was filtered, washed with water and Et$_2$O and pumped under reduced pressure to afford 1.67 g of 3-bromo-6-chlorophenanthrene-9,10-dione as a solid.

Step 4: 9-bromo-6-chloro-2-(2,6-dibromophenyl)-1H-phenanthro[9,10-d]imidazole

To a solution of 15.5 g of 3-bromo-6-chlorophenanthrene-9,10-dione from Step 3 in 400 mL of acetic acid, was added 74.2 g of ammonium acetate and 19.1 g of 2,6-dibromobenzaldehyde. The mixture was stirred overnight at 120° C., cooled down to room temperature diluted in 4 L of water and filtered. The resulting solid was refluxed 2 hrs in toluene with a Dean Stark apparatus. After cooling down to room temperature, the suspension was filtered, the solid washed with toluene and the resulting beige solid dried under high vacuum to produce 26 g of 9-bromo-6-chloro-2-(2,6-dibromophenyl)-1H-phenanthro[9,10-d]imidazole.

Step 5: 2-(9-bromo-6-chloro-1H-phenanthro[9,10-d]imidazol-2-yl)isophthalonitrile To a solution of 26 g of 9-bromo-6-chloro-2-(2,6-dibromophenyl)-1H-phenanthro[9,10-d]imidazole from Step 4 in 200 mL of dry DMF, was added 14.2 g of CuCN. The reaction was stirred overnight at 85° C., cooled down to room temperature, brine was added and the mixture stirred for 30 minutes. The solution was diluted in ethyl acetate, washed with 10% ammonium hydroxide, brine, dried over sodium sulphate and volatiles were removed under reduced pressure to afford 26 g of 2-(9-bromo-6-chloro-1H-phenanthro[9,10-d]imidazol-2-yl)isophthalonitrile as a solid. $^1$H NMR (Acetone-$d_6$): 9.19 (s, 1H), 9.02 (s, 1H), 9.71 (bs, 1H), 8.49 (bs, 1H), 8.39 (d, 2H), 8.07 (t, 1H), 7.97 (d, 1H), 8.81 (d, 1H).

Example 40

2-[9-chloro-6-(3-hydroxy-3-methylbut-1-yn-1-yl)-1H-phenanthro[9,10-d]imidazol-2-yl]isophthalonitrile

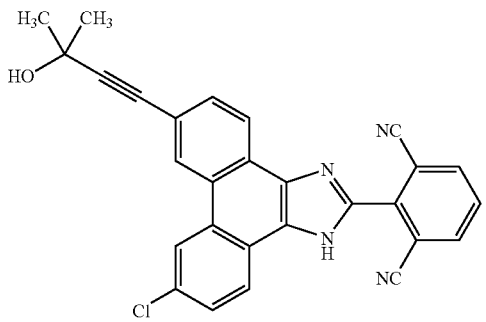

Step 1: (2E)-2-(4-bromophenyl)-3-(4-chloro-2-nitrophenyl)acrylic acid

A 2 L flask equipped with a mechanical stirrer was charged with 183 g of 2-nitro-4-chlorobenzaldehyde, 212 g of 4-broinophenylacetic acid and 233 mL of acetic anhydride. To this solution was added 82 g of potassium carbonate and the reaction was stirred overnight at 100° C. The resulting dark mixture was cooled down to room temperature and 1.6 L of water was added followed by 800 mL of 10% HCl. The solution was decanted and taken up in water/ethyl acetate. Layers were separated, organic phase washed with brine, dried over magnesium sulphate and volatiles were removed under reduced pressure. The residue was triturated in EtOH and the mother liquor was triturated 4 more times with EtOH to afford 219 g of the desired (2E)-2-(4-bromophenyl)-3-(4-chloro-2-nitrophenyl)acrylic acid.

Step 2: (2E)-3-(2-amino-4-chlorophenyl)-2-(4-bromophenyl)acrylic acid

To a 50° C. solution of 135 g of (2E)-2-(4-bromophenyl)-3-(4-chloro-2-nitrophenyl)acrylic acid from Step 1 in 1.2 L of acetic acid and 80 mL of water, was added 98 g of iron (powder) portion wise maintaining the temperature below 50° C. The mixture was stirred 2 hrs at 50° C., cooled down to room temperature, diluted with ethyl acetate (1 L) and filtered through a plug of celite. Water (1 L) was added, the layers were separated and the organic layer washed 2 times with water, brine, dried over magnesium sulphate and volatiles were removed under reduced pressure. Residual acetic acid was removed by the addition of 1 L of $H_2O$ to the crude mixture, the solution was filtered and washed with an additional 1 L of $H_2O$ and finally the solid was dried under high vacuum to afford 130 g of (2E)-3-(2-amino-4-chlorophenyl)-2-(4-bromophenyl)acrylic acid.

Step 3: 3-Bromo-6-chlorophenanthrene-9,10-dione

This quinone can be obtained by following the procedure describe in Example 36, Step 1 to 3, or by the using the following procedure: to a 0° C. solution of 118 mL of concentrated sulphuric acid in 1.0 L of water was added drop wise a solution prepared as follows: 65 g of (2E)-3-(2-amino-4-chlorophenyl)-2-(4-bromophenyl)acrylic acid from Step 2 in 1 L of water followed by the addition of 11 g of NaOH, stirring for 10 minutes at 0° C., addition of $NaNO_2$ (15 g) and stirring of the resulting solution at 0° C. for 20 minutes. After 30 minutes, sulfamic acid (12.5 g) was added to this mixture and after the gaz evolution seized, 1.3 L of acetone was added and the solution was stirred at 0° C. for 10 minutes. This mixture was then added to a solution of ferrocene (6.9 g) in 480 mL of acetone resulting in the formation of a green precipitate. After stirring for 20 minutes, water (2.0 L) was added, the solid was filtered and the 6-bromo-3-chlorophenanthrene-9-carboxylic acid was obtained and allowed to air dry. This crude phenanthrene was placed in 2.0 L of acetic acid followed by the addition of 54 g of $CrO_3$. The reaction was placed at 110° C. and after stirring for 1 hr, 18 g of $CrO_3$ were added. The reaction was monitored by TLC and 18 g of $CrO_3$ were added every hour for 3 hours where 100% conversion was observed by $^1$H NMR. The mixture was cooled to room temperature, diluted in water (2.0 L), filtered and washed with water (1.0 L) to afford, after drying, 37 g of 3-Bromo-6-chlorophenanthrene-9,10-dione as a yellow solid.

Step 4: 9-bromo-6-chloro-2-(2,6-dibromophenyl)-1H-phenanthro[9,10-d]imidazole

This imidazole was obtained following the procedure describe for Example 36, Step 4.

Step 5: 2-(9-bromo-6-chloro-1H-phenanthro[9,10-d]imidazol-2-yl)isophthalonitrile This imidazole was obtained following the procedure describe for Example 36, Step 5.

Step 6: 2-[9-chloro-6-(3-hydroxy-3-methylbut-1-yn-1-yl)-1H-phenanthro[9,10-d]imidazol-2-yl]isophthalonitrile To a solution of 13 g of 2-(9-bromo-6-chloro-1H-phenanthro[9,10-d]imidazol-2-yl)isophthalonitrile in 240 mL of DMF is added 5.5 mL of 2-methyl-3-butyn-2-ol, 2.0 g of tetrakis(triphenylphosphine)palladium, 1.1 g of copper iodide and 5.6 mL of diisopropylamine. The mixture is stirred at 55° C. for 1 hr then cooled to room temperature and diluted with ethyl acetate (250 mL). Water (250 mL) is added and the layers were separated, the organic phase is washed with brine, dried over magnesium sulphate and volatiles are removed under reduced pressure. The crude mixture is then purified on silica gel using 50% hexane/ethyl acetate. The product is then recrystallized in THF and triturated in hot ethyl acetate/ether mixture to afford 5.4 g of [9-chloro-6-(3-hydroxy-3-methylbut-1-yn-1-yl)-1H-phenanthro[9,10-d]imidazol-2-yl]isophthalonitrile as a light yellow solid. $^1$H NMR (Acetone-$d_6$): 8.93 (s, 2H), 8.53 (m, 2H), 8.36 (d, 2H), 8.01 (t, 1H), 7.78 (d, 2H), 4.53 (s, 1H), 1.61 (s, 6H).

Example 60

2-(1-{[dihydroxy(dioxido)phosphino]methyl}-1H-phenanthro[9,10-d]imidazol-2-yl)isophthalonitrile

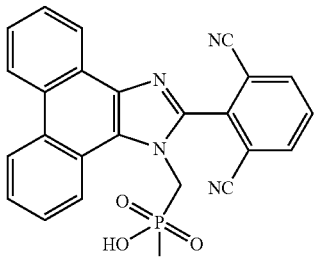

Step 1: 2-(2,6-dibromophenyl)-1H-phenanthro[9,10-d]imidazole

This imidazole was obtained following the procedure described in Example 36, Step 4, but substituting the phenanthrene-9,10-dione for the 3-bromo-6-chlorophenanthrene-9,10-dione to afford the 2-(2,6-dibromophenyl)-1H-phenanthro[9,10-d]imidazole

Step 2: 2-(1H-phenanthro[9,10-d]imidazol-2-yl)isophthalonitrile

This compound was obtained by using the procedure described in Example 36, Step 5, but substituting the 2-(2,6-dibromophenyl)-1H-phenanthro[9,10-d]imidazole for the 9-bromo-6-chloro-2-(2,6-dibromophenyl)-1H-phenanthro[9,10-d]imidazole to afford the desired 2-(1H-phenanthro[9,10-d]imidazol-2-yl)isophthalonitrile.

Step 3: 2-[1-(chloromethyl)-1H-phenanthro[9,10-d]imidazol-2-yl]isophthalonitrile 2-(1H-phenanthro[9,10-d]imidazol-2-yl)isophthalonitrile from Step 2 (1 g, 2.91 mmol) was mixed with cesium carbonate (1.14 g, 3.49 mmol) in chloroiodomethane (10 mL). The mixture was heated to 80° C. overnight. The reaction was cooled to room temperature and poured into 200 mL water and 500 mL ethyl acetate. The layers were separated, and the organic layer washed with 200 mL water, 200 mL saturated aqueous sodium bicarbonate solution, 100 mL brine, and dried over anhydrous magnesium sulfate. The solvent was removed under reduced pressure. The crude solid was purified by flash column chromatography using 40% ethyl acetate in hexane to give 357 mg of 2-[1-(chloromethyl)-1H-phenanthro[9,10-d]imidazol-2-yl]isophthalonitrile (31%) plus 650 mg of a mixture of product and starting material.

Step 4: 2-(1-{[dihydroxy(dioxido)phosphino]methyl)}-1H-phenanthro[9,10-d]imidazol-2-yl)isophthalonitrile The 2-[1-(chloromethyl)-1H-phenanthro[9,10-d]imidazol-2-yl]isophthalonitrile from Step 3 (200 mg, 0.509 mmol) was mixed with tetramethylammonium di(tert-butyl)phosphate (288 mg, 1.02 mmol) in DMF (5 mL) and heated at 50° C. for 8 hours. It was cooled to room temperature and poured into 15 mL water and 35 mL ethyl acetate. The layers were separated, and the organic layer was washed with 10 mL water (twice), 10 mL saturated aqueous sodium bicarbonate solution, brine, and dried over anhydrous magnesium sulfate. The solvent was removed under reduced pressure. The crude solid was purified by flash column chromatography using 50-70% ethyl acetate in hexane to give 221 mg of protected phosphate (77%). 155 mg of this solid was dissolved in 10% TFA/toluene (3 mL) and stirred at room temperature overnight. The solvent was removed under reduced pressure. The resulting crude product was purified by a semi-preparative RP-HPLC using a C18 column and eluting with a gradient of 44-49% acetonitrile+0.2% TFA over 8 min. The fractions containing product were combined and lyophilized to give 80 mg of the desired 2-(1-{[dihydroxy(dioxido)phosphino]methyl}-1H-phenanthro[9,10-d]imidazol-2-yl)isophthalonitrile.

$^1$H NMR (DMSO): 9.05 (d, 1H), 8.95 (d, 1H), 8.54-8.61 (m, 2H), 8.47 (d, 2H), 8.06 (t, 1H), 8.70-8.85 (m, 4H), 6.21 (d, 2H).

Example 87

2-[6-bromo-9-(1-hydroxy-1-methylethyl)-1H-phenanthro[9,10-d]imidazol-2-yl]isophthalonitrile

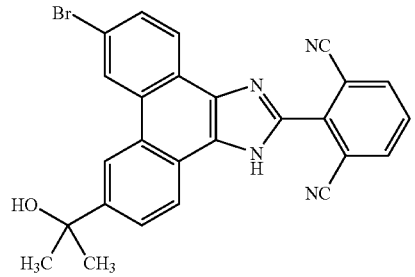

Step 1: 6,9-dibromo-2-(2,6-dibromophenyl)-1H-phenanthro[9,10-d]imidazole

A suspension of di-bromoquinone (38.6 g, 0.1 mol), ammonium acetate (165 g, 2.1 mol) and dibromobenzaldehyde (45 g, 0.1 mol) in acetic acid (1.5 L) was heated at reflux for 16 h. The reaction mixture was quenched by pouring it into water (2.2 L), followed by stirring for 2 h. The resulting solid was filtered and rinsed successively with water and hexanes. The solids were then heated at reflux in toluene (600 mL) with a Dean Stark for 4 h and then filtered to afford the desired 6,9-dibromo-2-(2,6-dibromophenyl)-1H-phenanthro[9,10-d]imidazole as a beige powder (62.3 g, 97%).

Step 2: 6,9-dibromo-2-(2,6-dibromophenyl)-1-{[2-(trimethylsilyl)ethoxy]methyl}-1H-phenanthro[9,10-d]imidazole To a suspension of 6,9-dibromo-2-(2,6-dibromophenyl)-1H-phenanthro[9,10-d]imidazole from Step 1 (61.8 g, 0.1 mol) in THF (980 mL) at 0° C., was added sodium hydride (60% dispersion in mineral oil, 10 g, 0.25 mol). The suspension was stirred at 0° C. for 15 minutes, followed by addition of SEMCI (45 mL, 0.25 mol). The mixture was warmed to room temperature and stirred for 3 h, after which it was poured into water. The aqueous phase was extracted with ethyl acetate, the organic layer washed once with brine, dried over Na$_2$SO$_4$, filtered and concentrated. The crude material was swished in hexanes/diethyl ether for 4 h, then filtered to obtain 6,9-dibromo-2-(2,6-dibromophenyl)-1-{[2-(trimethylsilyl)ethoxy]methyl}-1H-phenanthro[9,10-d]imidazole as a beige powder (71.5 g, 95%).

Step 3: methyl 6-bromo-2-(2,6-dibromophenyl)-1-{[2-(trimethylsilyl)ethoxy]methyl}-1H-phenanthro[9,10-d]imidazole-9-carboxylate To a solution of 6,9-dibromo-2-(2,6-dibromophenyl)-1-{[2-(trimethylsilyl)ethoxy]methyl}-1H-phenanthro[9,10-d]imidazole from Step 2 (22.8 g, 30.8 mmol) in DMF (150 mL) and MeOH (150 mL) in a 3-necked 1 L round-bottomed flask, was added Pd(OAc)$_2$ (350 mg, 1.5 mmol) and dppf (1.7 g, 3.0 mmol). The mixture was degassed three times and back-filled with carbon monoxide. Triethylamine (9.5 mL, 43 mmol) was then added and the reaction mixture was heated at 60° C., under an atmosphere of carbon monoxide, for 1 h. The reaction was quenched by pouring it into water and ethyl acetate. It was then filtered through Celite, the aqueous phase extracted with ethyl acetate, the organic layer washed once with brine, dried over Na$_2$SO$_4$, filtered and concentrated. The crude material was purified by flash chromatography on silica (0-5% ethyl acetate in toluene) to afford the isomers of the desired methyl 6-bromo-2-(2,6-dibromophenyl)-1-{[2-(trimethylsilyl)ethoxy]methyl}-1H-phenanthro[9,10-d]imidazole-9-carboxylate as beige solids (9.8 g, 44%).

Step 4: 2-[6-bromo-2-(2,6-dibromophenyl)-1H-phenanthro[9,10-d]imidazol-9-yl]propan-2-ol To a –78° C. solution of isomeric methyl 6-bromo-2-(2,6-dibromophenyl)-1-{[2-(trimethylsilyl)ethoxy]methyl}-1H-phenanthro[9,10-d]imidazole-9-carboxylate from Step 3 (9.9 g, 13.8 mmol) in CH$_2$Cl$_2$ (200 mL) was added methyl magnesium bromide (3.0 M in Et$_2$O, 33 mL) via addition funnel. The mixture was then warmed to –40° C., stirred at this temperature for 0.5 h, then warmed to between –30 and –35° C. and stirred at this temperature for 2 h. The reaction mixture was then warmed to –25° C., stirred for 3 h, and then stirred at 0° C. for 1.5 h. The reaction was quenched by pouring it into water and ethyl acetate. The aqueous phase was extracted with ethyl acetate, the organic layer washed once with brine, dried over Na$_2$SO$_4$, filtered and concentrated. The crude product was dissolved in THF (150 mL) and cooled to 0° C. TBAF (1.0 M in THF, 35 mL) was then added and the mixture heated at reflux for 17 h, then quenched with 25% NH$_4$OAc, the aqueous phase extracted with ethyl acetate, the organic layer washed once with brine, dried over Na$_2$SO$_4$, filtered and concentrated. The material obtained after purification by flash chromatography on silica (5-30% THF in toluene) was swished in toluene for 5 h and then filtered to afford 2-[6-bromo-2-(2,6-dibromophenyl)-1H-phenanthro[9,10-d]imidazol-9-yl]propan-2-ol as a white powder (4.53 g, 56%, 2 steps).

Step 5: 2-[6-bromo-9-(1-hydroxy-1-methylethyl)-1H-phenanthro[9,10-d]imidazol-2-yl]isophthalonitrile Copper cyanide (420 mg, 4.7 mmol) was added to a room temperature solution of 2-[6-bromo-2-(2,6-dibromophenyl)-1H-phenanthro[9,10-d]imidazol-9-yl]propan-2-ol from Step 4 (1.25 g, 2.1 mmol) in DMF (100 mL) and the mixture heated at 80° C. for 18 h, after which it was poured into a mixture of NH$_4$OH and ethyl acetate and stirred for 1 h. The aqueous phase was extracted with ethyl acetate, the organic layer washed once with water, once with brine, dried over Na$_2$SO$_4$, filtered and concentrated. The material obtained after purification by flash chromatography on silica (20-80% ethyl acetate in toluene) was swished in ethyl acetate and THF for 2 h and then filtered to afford 2-[6-bromo-9-(1-hydroxy-1-methylethyl)-1H-phenanthro[9,10-d]imidazol-2-yl]isophthalonitrile as a yellow solid (250 mg, 25%).

$^1$H NMR δ (ppm)(DMSO with added TFA): 9.08 (1H, s), 8.90 (1H, s), 8.45-8.39 (4H, m), 7.99-7.91 (3H, m), 1.61 (6H, s).

Example 88

2-[6-(cyclopropylethynyl)-9-(1-hydroxy-1-methylethyl)-1H-phenanthro[9,10-d]imidazol-2-yl]isophthalonitrile

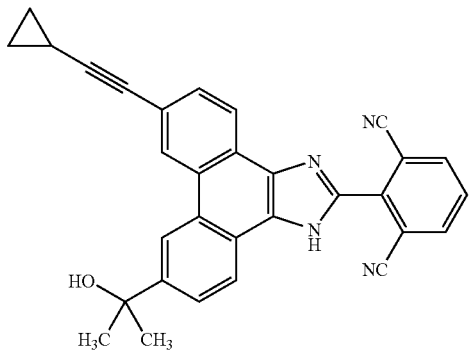

Step 1: 2-[6-(cyclopropylethynyl)-9-(1-hydroxy-1-methylethyl)-1H-phenanthro[9,10-d]imidazol-2-yl]isophthalonitrile A round bottomed flask containing 2-[6-bromo-9-(1-hydroxy-1-methylethyl)-1H-phenanthro[9,10-d]imidazol-2-yl]isophthalonitrile from Example 87 (1.26 g, 2.62 mmol), Pd(PPh$_3$)$_4$ (190 mg, 0.27 mmol) and copper iodide (100 mg, 0.52 mmol) was purged with nitrogen for 15 minutes, followed by addition of DMF (50 mL), cyclopropyl acetylene (1.4 mL, 21 mmol) and di-isopropylamine (560 µL, 4 mmol). The resulting mixture was heated at 60-65° C. for 3.5 h, cooled to room temperature and then poured into a mixture of NH$_4$OH and ethyl acetate and stirred for 1 h. The aqueous phase was extracted with ethyl acetate, the organic layer washed once with water, once with brine, dried over Na$_2$SO$_4$, filtered and concentrated. The material obtained after purification by flash chromatography on silica (30-100% ethyl acetate in toluene) was swished in toluene for 2 h and then filtered to afford 2-[6-(cyclopropylethynyl)-9-(1-hydroxy-1-methylethyl)-1H-phenanthro[9,10-d]imidazol-2-yl]isophthalonitrile as a yellow solid (350 mg). The mother liquor was combined with the mixed fractions and re-purified by flash chromatography on silica (3-40% acetonitrile in toluene) to afford 286 mg the bis-nitrile (total yield 52%).

$^1$H NMR δ (ppm)(DMSO with added TFA): 8.92 (1H, s), 8.87 (1H, s), 8.43-8.39 (4H, m), 7.96 (1H, t), 7.90 (1H, d), 7.71 (1H, d), 1.60 (7H, s), 0.90 (2H, t), 0.84 (2H, d).

Example 117

2-[9-chloro-6-(3-hydroxy-3-methylbutyl)-1H-phenanthro[9,10-d]imidazol-2-yl)isophthalonitrile

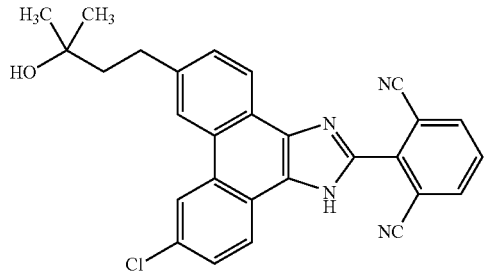

Step 1: 2-[9-chloro-6-(3-hydroxy-3-methylbutyl)-1H-phenanthro[9,10-d]imidazol-2-yl)isophthalonitrile To a solution of 9-BBN in THF (24 ml, 12 mmol, 0.5 M) was added 2-methyl-3-buten-2-ol (345 mg, 4.0 mmol) and the resulting solution was stirred under $N_2$ at rt for overnight. In a second flask charged with $PdCl_2$(dppf) (324 mg, 0.40 mmol), $Cs_2CO_3$ (2.4 g, 8.0 mmol) and $Ph_3As$ (124 mg, 0.4 mmol) was added 2-(6-bromo-9-chloro-1H-phenanthro[9,10-d]imidazol-2-yl)isophthalonitrile from Example 36, DMF (24 ml) and $H_2O$ (0.88 ml) and the mixture was stirred under $N_2$ for 5 minutes. The hydroboration mixture was then transferred to the second flask and the resulting reaction suspension was stirred at rt under $N_2$ for 5 days. After being treated with brine, the aqueous phase was extracted with EtOAc and the combined organic solution washed with water and brine, dried over $MgSO_4$. After removing the drying agent by filtration, the solution was concentrated under reduced pressure and the residue was purified by silica gel chromatography (50% EtOAc/Hexane) to yield 600 mg of 2-[9-chloro-6-(3-hydroxy-3-methylbutyl)-1H-phenanthro[9,10-d]imidazol-2-yl)isophthalonitrile as a yellow solid. $^1$H NMR (400 MHz, Acetone): δ 13.10 (s br, 1H); 8.94 (s, 1H); 8.77 (s, 1H); 8.70-8.60 (m br, 2H); 8.39 (d, 2H); 8.03 (t, 1H); 7.75 (dd, 1H); 7.69 (dd, 1H); 4.92 (s, 1H); 3.05 (m, 2H); 1.95 (m, 2H); 1.33 (s, 6H).

Example 123

(±)-2-[9-chloro-6-(3,4-dihydroxy-3-methylbut-1-yn-1-yl)-1H-phenanthro[9,10-d]imidazol-2-yl]isophthalonitrile

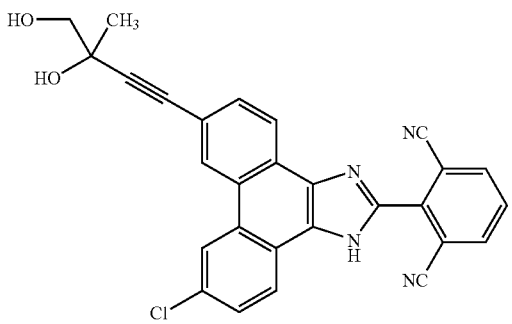

Step 1: 2-[6-chloro-9-(3-methylbut-3-en-1-yn-1-yl)-1H-phenanthro[9,10-d]imidazol-2-yl]isophthalonitrile To a stirred suspension of 2-[9-chloro-6-(3-hydroxy-3-methylbut-1-yn-1-yl)-1H-phenanthro[9,10-d]imidazol-2-yl] isophthalonitrile from Example 40 (120 mg, 0.26 mmol) in benzene (4 mL) was added Burgess Reagent (70 mg, 0.29 mmol) and refluxed for 2 hours under $N_2$. The resulting reaction mixture was diluted with EtOAc (20 mL). This EtOAc solution washed with water, brine and dried over $MgSO_4$. After removing the drying agent via filtration, the organic solution was concentrated under reduced pressure. The residue was purified by silica gel column chromatography (eluted with 50/50 EtOAc/hexane) to yield 90 mg of 2-[6-chloro-9-(3-methylbut-3-en-1-yn-1-yl)-1H-phenanthro[9,10-d]imidazol-2-yl]isophthalonitrile as a yellow solid.

Step 2: (±)-2-[9-chloro-6-(3,4-dihydroxy-3-methylbut-1-yn-1-yl)-1H-phenanthro[9,10-d]imidazol-2-yl] isophthalonitrile To a stirred suspension of 2-[6-chloro-9-(3-methylbut-3-en-1-yn-1-yl)-1H-phenanthro[9,10-d]imidazol-2-yl]isophthalonitrile from Step 1 (22 mg, 0.05 mmol) in 50/50 t-BuOH/$H_2O$ (0.5 mL) was added AD-mix-α (70 mg) at 0° C. The mixture was left stirring at 0° C. for 24 hours. The resulting reaction mixture was treated with saturated $Na_2S_2O_3$ aqueous solution and stirred for 10 minutes, diluted with water and extracted with EtOAc. This EtOAc solution washed with water, brine and dried over $MgSO_4$. After removing the drying agent via filtration, the organic solution was concentrated under reduced pressure. The residue was purified by silica gel column chromatography (eluted with 50/50 EtOAc/hexane to 95/5 EtOAc/MeOH) to yield 19 mg of yellow solid. This same procedure was repeated with AD-mix-β to yield another 19 mg of yellow solid. These two yellow solids were combined to give the racemic 2-[9-chloro-6-(3,4-dihydroxy-3-methylbut-1-yn-1-yl)-1H-phenanthro[9,10-d]imidazol-2-yl] isophthalonitrile.
$^1$H NMR (400 MHz, Acetone): δ 8.84 (d, 1H); 8.80 (s, 1H); 8.57 (d, 1H); 8.47 (d, 1H); 8.39 (d, 2H); 8.03 (t, 1H); 7.77 (dd, 8.6 Hz, 1H); 7.71 (dd, 1H); 4.56 (s, 1H); 4.30 (s, 1H); 3.67 (q, 2H); 1.56 (s, 3H).

Example 135

2-[9-chloro-6-(2-hydroxy-2-methylpropyl)-1H-phenanthro[9,10-d]imidazol-2-yl]isophthalonitrile

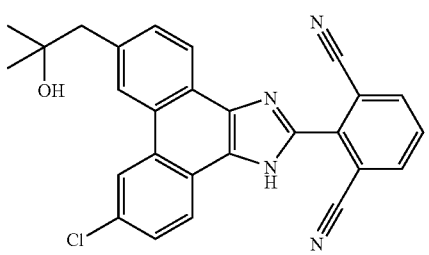

Step 1: 2-(6-bromo-9-chloro-1-{[2-(trimethylsilyl)ethoxy]methyl}-1H-phenanthro[9,10-d]imidazol-2-yl)isophthalonitrile To a solution of 2-(6-bromo-9-chloro-1H-phenanthro[9,10-d]imidazol-2-yl)isophthalonitrile (5 g, 10.9 mmol) from Example 36 in THF (30 mL) was added NaH (60% dispersion in oil, 1.31 g, 32.7 mmol). The mixture was stirred at room temperature for 10 minutes, after which 2-(trimethylsilyl)ethoxymethylchloride (5.8 mL, 32.7 mmol) was added. After 1 hour, the reaction was quenched by slow addition of water.

The aqueous layer was extracted with ethyl acetate, the organic layer washed once with water, once with brine, dried over anhydrous MgSO₄ and concentrated to afford crude 2-(6-bromo-9-chloro-1-{[2-(trimethylsilyl)ethoxy]methyl}-1H-phenanthro[9,10-d]imidazol-2-yl)isophthalonitrile (6.06 g).

Step 2: 2-(9-chloro-6-(2-oxopropyl)-1-{[2-(trimethylsilyl)ethoxy]methyl)-1H-phenanthro[9,10-d]imidazol-2-yl)isophthalonitrile A solution of tributyl(methoxy)stannane (4.5 mL, 15.5 mmol), isopropenylacetate (1.7 mL, 15.5 mmol), 2-(6-bromo-9-chloro-1-{[2-(trimethylsilyl)ethoxy]methyl}-1H-phenanthro[9,10-d]imidazol-2-yl)isophthalonitrile from Step 1 above (6.06 g, 10.3 mmol), palladium (II) acetate (0.232 g, 1.03 mmol) and tri-o-tolylphosphine (0.628 g, 2.07 mmol) in toluene (50 mL) was heated at 100° C. overnight. The reaction mixture was quenched with water and ethyl acetate. Following usual workup and chromatography on silica (50% ethyl acetate in hexanes), 2-(9-chloro-6-(2-oxopropyl)-1-{[2-(trimethylsilyl)ethoxy]methyl)-1H-phenanthro[9,10-d]imidazol-2-yl)isophthalonitrile (2.8 g) was isolated as a yellow-orange solid.

Step 3: 2-(9-chloro-6-(2-hydroxy-2-methylpropyl)-1-{[2-(trimethylsilyl)ethoxy]methyl}-1H-phenanthro[9,10-d]imidazol-2-yl)isophthalonitrile To a round bottomed flask at −78° C. charged with TiCl₄ (1 M in CH₂Cl₂, 20 mL), was added methyllithium (1.6 M in diethyl ether, 12.5 mL). The resulting deep red solution was stirred at −78° C. for 15 minutes and then added via cannula to a 0° C. solution of 2-(9-chloro-6-(2-oxopropyl)-1-{[2-(trimethylsilyl)ethoxy]methyl)-1H-phenanthro[9,10-d]imidazol-2-yl)isophthalonitrile (2.8 g, 5.0 mmol) from Step 2 above, in diethyl ether (10 mL). The resulting mixture was stirred at 0° C. for 3 h, then quenched with saturated ammonium chloride. The aqueous layer was extracted with ethyl acetate. The organic layer washed with brine, dried over MgSO₄, filtered and concentrated. The crude material was purified by flash chromatography on silica (50% ethyl acetate in hexanes) to provide 2-(9-chloro-6-(2-hydroxy-2-methylpropyl)-1-{[2-(trimethylsilyl)ethoxy]methyl}-1H-phenanthro[9,10-d]imidazol-2-yl)isophthalonitrile (1.94 g), Step 4: 2-[9-chloro-6-(2-hydroxy-2-methylpropyl)-1H-phenanthro[9,10-d]imidazol-2-yl]isophthalonitrile 2-(9-chloro-6-(2-hydroxy-2-methylpropyl)-1-{[2-(trimethylsilyl)ethoxy]methyl}-1H-phenanthro[9,10-d]imidazol-2-yl)isophthalonitrile (1.94 g) from Step 3 above was dissolved in TBAF (1 M in THF, 20 mL). The mixture was heated at reflux for 5 h and then quenched with water. The aqueous layer was extracted with ethyl acetate. The organic layer washed with brine, dried over MgSO₄, filtered and concentrated. The crude material was purified by flash chromatography on silica (50% ethyl acetate in hexanes) to provide 2-[9-chloro-6-(2-hydroxy-2-methylpropyl)-1H-phenanthro[9,10-d]imidazol-2-yl]isophthalonitrile (500 mg) as a yellow solid. ¹H NMR δ (ppm)(400 MHz, Acetone-d₆): 13.13 (1H, bs), 8.87 (1H, s), 8.77 (1H, s), 8.58 (1H, m), 8.43 (1H, m), 8.35 (2H, d, J=7.9Hz), 7.99 (1H, t, J=7.9 Hz), 7.73 (2H, dd, J=1.9, 8.6Hz), 3.51 (1H, bs), 3.08 (2H, s), 1.26 (6H, s).

Example 160

2-[9-(cyclopropylmethoxy)-6-(3-hydroxy-3-methyl-but-1-yn-1-yl)-1H-phenanthro[9,10-d]imidazol-2-yl] isophthalonitrile

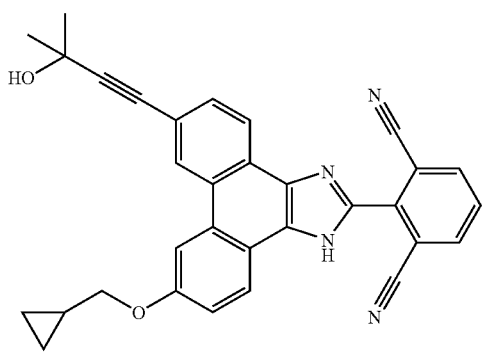

Step 1:
1-bromo-4-[2-(4-methoxyphenyl)vinyl]benzene

This stillbene was prepared as described in Step 1 of Example 36, substituting p-anisaldehyde for 4-chlorobenzaldehyde.

Step 2: 3-bromo-6-methoxyphenanthrene

This phenanthrene was prepared as described in Step 2 of Example 36, substituting 1-bromo-4-[2-(4-methoxyphenyl)vinyl]benzene from Step 1 above for 1-bromo-4-[2-(4-chlorophenyl)vinyl]benzene and performing the irradiation for 4 days.

Step 3: 3-bromo-6-methoxyphenanthrene-9,10-dione

This quinone was prepared as described in Step 3, Example 36, substituting 3-bromo-6-methoxyphenanthrene from Step 2 above for 3-bromo-6-chlorophenanthrene.

Step 4: 3-bromo-6-hydroxyphenanthrene-9,10-dione

A mixture of 3-bromo-6-methoxyphenanthrene-9,10-dione from Step 3 above and excess BBr₃ in CH₂Cl₂ was stirred at room temperature to afford 3-bromo-6-hydroxyphenanthrene-9,10-dione which was used directly in the next step (Step 5 below).

Step 5: 3-bromo-6-(cyclopropylmethoxy)phenanthrene-9,10-dione

A solution of 3-bromo-6-hydroxyphenanthrene-9,10-dione from Step 4 in acetone was treated with excess potassium carbonate, potassium iodide and (bromomethyl)cyclopropane. The mixture was heated at reflux overnight, followed by standard workup to yield 3-bromo-6-(cyclopropylmethoxy)phenanthrene-9,10-dione.

Step 6: 6-bromo-9-(cyclopropylmethoxy)-2-(2,6-dibromophenyl)-1H-phenanthro[9,10-d]imidazole This imidazole was prepared as described in Step 4 of Example 36, substituting 3-bromo-6-(cyclopropylmethoxy)phenanthrene-9,10-dione from Step 5 above for 3-bromo-6-chlorophenanthrene-9,10-dione

Step 7: 2-[6-bromo-9-(cyclopropylmethoxy)-1H-phenanthro[9,10-d]imidazol-2-yl]isophthalonitrile This imidazole was prepared as described in Step 5 of Example 36, substituting 6-bromo-9-(cyclopropylmethoxy)-2-(2,6-dibromophenyl)-1H-phenanthro[9,10-d]imidazole from Step 6 above for 9-bromo-6-chloro-2-(2,6-dibromophenyl)-1H-phenanthro[9,10-d]imidazole. The impurity present in the product was removed by Sharpless dihydroxylation.

Step 8: 2-[9-(cyclopropylmethoxy)-6-(3-hydroxy-3-methylbut-1-yn-1-yl)-1H-phenanthro[9,10-d]imidazol-2-yl]isophthalonitrile This imidazole was prepared as described in Step 6, Example 40, substituting 2-[6-bromo-9-(cyclopropylmethoxy)-1H-phenanthro[9,10-d]imidazol-2-yl]isophthalonitrile from Step 7 above for 2-(9-bromo-6-chloro-1H-phenanthro[9,10-d]imidazol-2-yl)isophthalonitrile. $^1$H NMR δ (ppm)(400 MHz, Acetone-$d_6$): 13.04 (1H, bs), 8.88 (1H, d, J=5.7 Hz), 8.49 (2H, m), 8.33 (3H, m), 7.99 (1H, t, J=8.0 Hz), 7.73 (1H, d, J=8.2 Hz), 7.43 (1H, d, J=8.8 Hz), 4.54 (1H, bs), 4.17 (2H, d, J=6.8 Hz), 1.63 (6H, s), 1.48-1.36 (1H, m), 0.68 (1H, m), 0.49-0.45 (1H, m).

Example 168

2-[9-(cyclopropylmethoxy)-6-(2-hydroxy-2-methylpropyl)-1H-phenanthro[9,10-d]imidazol-2-yl]isophthalonitrile

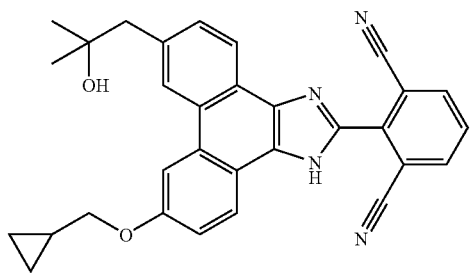

This compound was prepared by two routes as described below:

Route A:

Step 1: 6-bromophenanthren-3-ol

To a flask containing BBr$_3$ (1 M in CH$_2$Cl$_2$, 17 mL) at 0° C. was added a solution of 3-bromo-6-methoxyphenanthrene (1 g, 3.5 mmol) from Step 2, Example 160 in CH$_2$Cl$_2$ (10 mL). The reaction mixture was warmed to room temperature and stirred for 30 minutes, after which it was quenched with water. The aqueous layer was extracted with CH$_2$Cl$_2$. The organic layer was dried over MgSO$_4$, filtered and concentrated to yield crude 6-bromophenanthren-3-ol.

Step 2: 3-bromo-6-(cyclopropylmethoxy)phenanthrene

A mixture of 6-bromophenanthren-3-ol (0.823 g, 3.02 mmol) from Step 1 above, (bromomethyl)cyclopropane (0.5 mL, 5.4 mmol), potassium carbonate (2.5 g, 18 mmol) and potassium iodide (5 mg) in acetone (50 mL) was heated at reflux for 3 days. Water was then added and the reaction mixture extracted with ethyl acetate The organic layer washed with brine, dried over MgSO$_4$, filtered and concentrated. The crude material was purified by flash chromatography on silica (100% hexanes) to provide 3-bromo-6-(cyclopropylmethoxy)phenanthrene (0.859 g, 87%).

Step 3: 1-[6-(cyclopropylmethoxy)-3-phenanthryl]acetone

This phenanthrene was prepared as described in Step 2 of Example 135, substituting 3-bromo-6-(cyclopropylmethoxy)phenanthrene from Step 2 above for 2-(6-bromo-9-chloro-1-([2-{trimethylsilyl}ethoxy]methyl}-1H-phenanthro[9,10-d]imidazol-2-yl)isophthalonitrile.

Step 4: 1-[6-(cyclopropylmethoxy)-3-phenanthryl]-2-methylpropan-2-ol

This phenanthrene was prepared as described in Step 3 of Example 135, substituting 1-[6-(cyclopropylmethoxy)-3-phenanthryl]acetone from Step 3 above for 2-(9-chloro-6-(2-oxopropyl)-1-{[2-(trimethylsilyl)ethoxy]methyl)-1H-phenanthro[9,10-d]imidazol-2-yl)isophthalonitrile. The crude product was used directly in the next reaction.

Step 5: tert-butyl(2-[6-(cyclopropylmethoxy)-3-phenanthryl]-1,1-dimethylethoxy)dimethylsilane To a solution of crude 1-[6-(cyclopropylmethoxy)-3-phenanthryl]-2-methylpropan-2-ol from Step 4 above in THF (10 mL), was added sodium hydride (60% dispersion in oil, 0.27 g, 6.79 mmol). The mixture was heated at reflux for 2 minutes, then cooled to room temperature. Tert-butyldimethylsilylchloride (0.512 g, 3.39 mmol) was added and the reaction mixture heated at reflux for 2 h. After usual workup of the reaction, tert-butyl(2-[6-(cyclopropylmethoxy)-3-phenanthryl]-1,1-dimethylethoxy)dimethylsilane (0.5 g) was obtained, which was used as crude material for the next step.

Step 6: 3-(2-{[tert-butyl(dimethyl)silyl]oxy}-2-methylpropyl)-6-(cyclopropylmethoxy)phenanthrene-9,10-dione To a solution of tert-butyl(2-[6-(cyclopropylmethoxy)-3-phenanthryl]-1,1-dimethylethoxy)dimethylsilane (0.5 g, 1.15 mmol) from Step 5 above, in acetic acid (10 mL), was added CrO$_3$ (0.346 g, 3.46 mmol). The mixture was stirred at 50° C. for 30 min, cooled down to room temperature, poured into water and stirred for 15 minutes. The suspension was filtered, washed with water and pumped under reduced pressure to afford 3-(2-{[tert-butyl(dimethyl)silyl]oxy}-2-methylpropyl)-6-(cyclopropylmethoxy)phenanthrene-9,10-dione.

Step 7: 6-(2-{[tert-butyl(dimethyl)silyl]oxy}-2-methylpropyl)-9-(cyclopropylmethoxy)-2-(2,6-dibromophenyl)-1H-phenanthro[9,10-d]imidazole To a solution of 3-(2-{[tert-butyl(dimethyl)silyl]oxy}-2-methylpropyl)-6-(cyclopropylmethoxy)phenanthrene-9,10-dione (1.15 mmol) from Step 6 above in acetic acid (10 ml), was added ammonium acetate (1.78 g, 23 mmol) and dibromobenzaldehyde (0.42 g, 1.5 mmol). The mixture was stirred at 70° C. for 1 h, cooled down to room temperature, poured into water and stirred for 5 minutes. The resulting solid washed with water and diethyl ether. The crude material was purified by flash chromatography on silica (30% ethyl acetate in hexanes) to afford 6-(2-{[tert-butyl(dimethyl)silyl]oxy}-2-methylpropyl)-9-(cyclopropylmethoxy)-2-(2,6-dibromophenyl)-1H-phenanthro[9,10-d]imidazole (0.223 g) as a yellow solid.

Step 8: 1-[9-(cyclopropylmethoxy)-2-(2,6-dibromophenyl)-1H-phenanthro[9,10-d]imidazol-6-yl]-2-methylpropan-2-ol TBAF (1 M in THF, 10 mL) was added to a flask containing 6-(2-{[tert-butyl(dimethyl)silyl]oxy}-2-methylpropyl)-9-(cyclopropylmethoxy)-2-(2,6-dibromophenyl)-1H-phenanthro[9,10-d]imidazole (0.223 g, 0.31 mmol) from Step 7 above, at room temperature. The resulting solution was heated at reflux for 36 h, after which water was added to the reaction mixture. The aqueous layer was extracted with ethyl acetate, the organic layer dried over MgSO₄, filtered and concentrated. The crude product was used directly in the next reaction (Step 9 below).

Step 9: 2-[9-(cyclopropylmethoxy)-6-(2-hydroxy-2-methylpropyl)-1H-phenanthro[9,10-d]imidazol-2-yl]isophthalonitrile This imidazole was prepared as described in Step 5 of Example 36, substituting crude 1-[9-(cyclopropylmethoxy)-2-(2,6-dibromophenyl)-1H-phenanthro[9,10-d]imidazol-6-yl]-2-methylpropan-2-ol from Step 8 above for 9-bromo-6-chloro-2-(2,6-dibromophenyl)-1H-phenanthro[9,10-d]imidazole. $^1$H NMR δ (ppm)(400 MHz, Acetone-$d_6$): 12.96 (1H, bs), 8.70 (1H, m), 8.59 (1H, m), 8.32 (3H, d, J=8.0 Hz), 8.28 (1H, m), 7.95 (1H, t, J=7.9 Hz), 7.67 (1H, d, J=8.1 Hz), 7.38 (1H, d, J=8.7 Hz), 4.09 (2H, d, J=6.9 Hz), 3.46 (1H, bs), 3.05 (2H, s), 1.38-1.34 (1H, m), 1.25 (6H, s), 0.67-0.63 (2H, m), 0.45-0.41 (2H, m).

Route B:

Step 1: 3-bromo-6-(cyclopropylmethoxy)phenanthrene-9,10-dione

This quinone was prepared either as described in Step 5, Example 160, or by following the procedure described in Step 3, Example 36, substituting 3-bromo-6-(cyclopropylmethoxy)phenanthrene from Step 2 of Route A above for 3-bromo-6-chlorophenanthrene.

Step 2: 6-bromo-9-(cyclopropylmethoxy)-2-(2,6-dibromophenyl)-1H-phenanthro[9,10-d]imidazole This imidazole was prepared as described in Step 6 of Example 160.

Step 3: 2-[6-bromo-9-(cyclopropylmethoxy)-1H-phenanthro[9,10-d]imidazol-2-yl]isophthalonitrile This imidazole was prepared as described in Step 7 of Example 160.

Step 4: 2-(6-bromo-9-(cyclopropylmethoxy)-1-{[2-(trimethylsilyl)ethoxy]methyl}-1H-phenanthro[9,10-d]imidazol-2-yl)isophthalonitrile This SEM-protected imidazole was prepared as described in Step 2, Example 87, substituting 2-[6-bromo-9-(cyclopropylmethoxy)-1H-phenanthro[9,10-d]imidazol-2-yl]isophthalonitrile from Step 3 above for 6,9-dibromo-2-(2,6-dibromophenyl)-1H-phenanthro[9,10-d]imidazole.

Step 5: 2-(9-(cyclopropylmethoxy)-6-(2-oxopropyl)-1-{[2-(trimethylsilyl)ethoxy]methyl}-1H-phenanthro[9,10-d]imidazol-2-yl)isophthalonitrile This imidazole was prepared as described in Step 2, Example 135, substituting 2-(6-bromo-9-(cyclopropylmethoxy)-1-{[2-(trimethylsilyl)ethoxy]methyl}-1H-phenanthro[9,10-d]imidazol-2-yl)isophthalonitrile from Step 4 above for 2-(6-bromo-9-chloro-1-([2-(trimethylsilyl)ethoxy]methyl)-1H-phenanthro[9,10-d]imidazol-2-yl)isophthalonitrile.

Step 6: 2-(9-(cyclopropylmethoxy)-6-(2-hydroxy-2-methylpropyl)-1-{[2-(trimethylsilyl)ethoxy]methyl}-1H-phenanthro[9,10-d]imidazol-2-yl)isophthalonitrile This imidazole was prepared as described in Step 3, Example 135, substituting 2-(9-(cyclopropylmethoxy)-6-(2-oxopropyl)-1-{[2-(trimethylsilyl)ethoxy]methyl}-1H-phenanthro[9,10-d]imidazol-2-yl)isophthalonitrile from Step 5 above for of 2-(9-chloro-6-(2-oxopropyl)-1-{[2-(trimethylsilyl)ethoxy]methyl)-1H-phenanthro[9,10-d]imidazol-2-yl)isophthalonitrile.

Step 7: 2-[9-(cyclopropylmethoxy)-6-(2-hydroxy-2-methylpropyl)-1H-phenanthro[9,10-d]imidazol-2-yl]isophthalonitrile Crude 2-(9-(cyclopropylmethoxy)-6-(2-hydroxy-2-methylpropyl)-1-{[2-(trimethyl silyl)ethoxy]methyl}-1H-phenanthro[9,10-d]imidazol-2-yl)isophthalonitrile (1.37 mmol) from Step 6 above was dissolved in TBAF (1 M in THF, 10 mL) and the mixture heated at reflux for 1.5 h. Water was added, and the aqueous layer extracted with ethyl acetate. The organic layer was dried over MgSO₄, filtered and concentrated. The material was purified by flash chromatography on silica (70% ethyl acetate in hexanes) to afford 2-[9-(cyclopropylmethoxy)-6-(2-hydroxy-2-methylpropyl)-1H-phenanthro[9,10-d]imidazol-2-yl]isophthalonitrile (240 mg).

Example 172

2-[9-(2-cyclopropylethoxy)-6-(2-hydroxy-2-methylpropyl)-1H-phenanthro[9,10-d]imidazol-2-yl]-5-fluoroisophthalonitrile

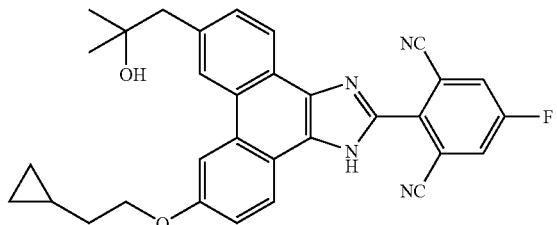

Step 1:
3-bromo-6-(2-cyclopropylethoxy)phenanthrene

To a mixture of 6-bromophenanthren-3-ol (3 g, 11 mmol) from Step 1 of Route A of Example 168, 2-cyclopropyletha nol (2.85 g, 33 mmol) and triphenylphosphine (5.78 g, 22 mmol) in THF (50 mL) was added di-tert-butylazodicarboxylate (5.08 g, 22 mmol). The reaction mixture was stirred at room temperature overnight, then quenched with water. The aqueous layer was extracted with ethyl acetate. The combined organic layer washed with brine, dried over $MgSO_4$, filtered and concentrated. The material was purified by flash chromatography on silica (100% hexanes) to afford 3-bromo-6-(2-cyclopropylethoxy)phenanthrene.

Step 2: 1-[6-(2-cyclopropylethoxy)-3-phenanthryl]-2-methylpropan-2-ol

This phenanthrene could either be prepared via the two-step process described in Steps 3 and 4 of Route A of Example 168, substituting 3-bromo-6-(2-cyclopropylethoxy)phenanthrene from Step 1 above for 3-bromo-6-(cyclopropylmethoxy)phenanthrene, or by following the procedure below:

To a solution of 3-bromo-6-(2-cyclopropylethoxy)phenanthrene (11 mmol) from Step 1 above in THF (75 mL) at −78° C. was successively added methyllithium (1.6 M in diethyl ether, 1 mL) and butyllithium (2.5 M in hexanes, 5.3 mL). The mixture was stirred at −78° C. for 30 minutes, after which isobutylene oxide (2.9 mL, 33 mmol) was added, followed by $BF_3 \cdot OEt_2$ (4.2 mL, 33 mmol). The reaction mixture was stirred at −78° C. for 1 h, then quenched with 1 M HCl. The aqueous layer was extracted with ethyl acetate. The combined organic layer washed with brine, dried over $MgSO_4$, filtered and concentrated. The material was purified by flash chromatography on silica (10% ethyl acetate in hexanes) to afford 1-[6-(2-cyclopropylethoxy)-3-phenanthryl]-2-methylpropan-2-ol (1.33 g) as a yellow oil.

Step 3: tert-butyl(2-[6-(2-cyclopropylethoxy)-3-phenanthryl]-1,1-dimethylethoxy)dimethylsilane This phenanthrene was prepared as described in Step 5 of Route A of Example 168, substituting 1-[6-(2-cyclopropylethoxy)-3-phenanthryl]-2-methylpropan-2-ol from Step 2 above for 1-[6-(cyclopropylmethoxy)-3-phenanthryl]-2-methylpropan-2-ol.

Step 4: 3-(2-{[tert-butyl(dimethyl)silyl]oxy}-2-methylpropyl)-6-(2-cyclopropylethoxy)phenanthrene-9,10-dione This quinone was prepared as described in Step 6 of Route A of Example 168, substituting tert-butyl(2-[6-(2-cyclopropylethoxy)-3-phenanthryl]-1,1-dimethylethoxy)dimethylsilane from Step 3 above for tert-butyl(2-[6-(cyclopropylmethoxy)-3-phenanthryl]-1,1-dimethylethoxy)dimethylsilane.

Step 5: 6-(2-{[tert-butyl(dimethyl)silyl]oxy}-2-methylpropyl)-9-(2-cyclopropylethoxy)-2-(2,6-dibromo-4-fluorophenyl)-1H-phenanthro[9,10-d]imidazole This imidazole was prepared as described in Step 7 of Route A of Example 168, substituting 3-(2-{[tert-butyl(dimethyl)silyl]oxy}-2-methylpropyl)-6-(2-cyclopropylethoxy)phenanthrene-9,10-dione from Step 4 above for 3-(2-{[tert-butyl(dimethyl)silyl]oxy}-2-methylpropyl)-6-(cyclopropylmethoxy)phenanthrene-9,10-dione and 2,6-dibromo-4-fluorobenzaldehyde for dibromobenzaldehyde.

Step 6: 1-[9-(2-cyclopropylethoxy)-2-(2,6-dibromo-4-fluorophenyl)-1H-phenanthro[9,10-d]imidazol-6-yl]-2-methylpropan-2-ol This imidazole was prepared as described in Step 8 of Route A of Example 168, substituting 6-(2-{[tert-butyl(dimethyl)silyl]oxy}-2-methylpropyl)-9-(2-cyclopropylethoxy)-2-(2,6-dibromo-4-fluorophenyl)-1H-phenanthro[9,10-d]imidazole from Step 5 above for 6-(2-{[tert-butyl(dimethyl)silyl]oxy}-2-methylpropyl)-9-(cyclopropylmethoxy)-2-(2,6-dibromophenyl)-1H-phenanthro[9,10-d]imidazole.

Step 7: 2-[9-(2-cyclopropylethoxy)-6-(2-hydroxy-2-methylpropyl)-1H-phenanthro[9,10-d]imidazol-2-yl]-5-fluoroisophthalonitrile This imidazole was prepared as described in Step 5 of Example 36, substituting 1-[9-(2-cyclopropylethoxy)-2-(2,6-dibromo-4-fluorophenyl)-1H-phenanthro[9,10-d]imidazol-6-yl]-2-methylpropan-2-ol from Step 6 above for 9-bromo-6-chloro-2-(2,6-dibromophenyl)-1H-phenanthro[9,10-d]imidazole. $^1$H NMR δ (ppm)(400 MHz, Acetone-$d_6$): 12.95 (1H, bs), 8.70 (1H, m), 8.58 (1H, m), 8.28 (4H, m), 7.67 (1H, d, J=8.1 Hz), 7.40 (1H, d, J=9.1 Hz), 4.31 (2H, t, J=6.5 Hz), 3.43 (1H, bs), 3.05 (2H, s), 1.78 (2H, q, J=6.7 Hz), 1.26 (6H, s), 0.98 (1H, m), 0.54-0.48 (2H, m), 0.20-0.18 (2H, m).

Example 180

2-[6-(2-hydroxy-2-methylpropyl)-9-(4,4,4-trifluorobutoxy)-1H-phenanthro[9,10-d]imidazol-2-yl]isophthalonitrile

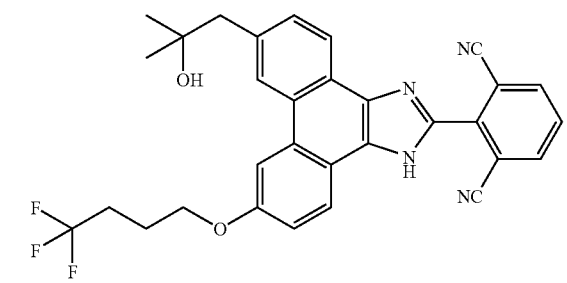

Step 1:
3-bromo-6-(4,4,4-trifluorobutoxy)phenanthrene

This phenanthrene was prepared as described in Step 2 of Route A of Example 168, substituting 4,4,4-trifluoro-1-iodobutane for (bromomethyl)cyclopropane.

Step 2: 2-methyl-1-[6-(4,4,4-trifluorobutoxy)-3-phenanthryl]propan-2-ol

This phenanthrene was prepared as described in Step 2, Example 172, substituting 3-bromo-6-(4,4,4-trifluorobutoxy)phenanthrene from Step 1 above for 3-bromo-6-(2-cyclopropylethoxy)phenanthrene.

Step 3: tert-butyl(1,1-dimethyl-2-[6-(4,4,4-trifluorobutoxy)-3-phenanthryl]ethoxy)dimethylsilane This phenanthrene was prepared as described in Step 5 of Route A of Example 168, substituting 2-methyl-1-[6-(4,4,4-trifluorobutoxy)-3-phenanthryl]propan-2-ol from Step 2 above for 1-[6-(cyclopropylmethoxy)-3-phenanthryl]-2-methylpropan-2-ol.

Step 4: 3-(2-{[tert-butyl(dimethyl)silyl]oxy}-2-methylpropyl)-6-(4,4,4-trifluorobutoxy)phenanthrene-9,10-dione This quinone was prepared as described in Step 6 of Route A of Example 168, substituting tert-butyl(1,1-dimethyl-2-[6-(4,4,4-trifluorobutoxy)-3-phenanthryl]ethoxy)dimethylsilane from Step 3 above for tert-butyl(2-[6-(cyclopropylmethoxy)-3-phenanthryl]-1,1-dimethylethoxy) dimethylsilane.

Step 5: 6-(2-([tert-butyl(dimethyl)silyl]oxy)-2-methylpropyl)-2-(2,6-dibromophenyl)-9-(4,4,4-trifluorobutoxy)-1H-phenanthro[9,10-d]imidazole This imidazole was prepared as described in Step 7 of Route A of Example 168, substituting 3-(2-{[tert-butyl(dimethyl)silyl]oxy}-2-methylpropyl)-6-(4,4,4-trifluorobutoxy) phenanthrene-9,10-dione from Step 4 above for 3-(2-{[tert-butyl(dimethyl)silyl]oxy}-2-methylpropyl)-6-(cyclopropylmethoxy)phenanthrene-9,10-dione.

Step 6: 1-[2-(2,6-dibromophenyl)-9-(4,4,4-trifluorobutoxy)-1H-phenanthro[9,10-d]imidazol-6-yl]-2-methylpropan-2-ol This imidazole was prepared as described in Step 8 of Route A of Example 168, substituting 6-(2-([tert-butyl(dimethyl)silyl]oxy)-2-methylpropyl)-2-(2,6-dibromophenyl)-9-(4,4,4-trifluorobutoxy)-1H-phenanthro[9,10-d]imidazole from Step 5 above for 6-(2-{[tert-butyl(dimethyl)silyl]oxy}-2-methylpropyl)-9-(cyclopropylmethoxy)-2-(2,6-dibromophenyl)-1H-phenanthro[9,10-d]imidazole.

Step 7: 2-[6-(2-hydroxy-2-methylpropyl)-9-(4,4,4-trifluorobutoxy)-1H-phenanthro[9,10-d]imidazol-2-yl]isophthalonitrile This imidazole was prepared as described in Step 5 of Example 36, substituting 1-[2-(2,6-dibromophenyl)-9-(4,4,4-trifluorobutoxy)-1H-phenanthro[9,10-d]imidazol-6-yl]-2-methylpropan-2-ol from Step 6 above for 9-bromo-6-chloro-2-(2,6-dibromophenyl)-1H-phenanthro[9,10-d]imidazole.
$^1$H NMR δ (ppm)(400 MHz, Acetone-$d_6$): 12.95 (1H, bs), 8.72 (2H, m), 8.33 (4H, m), 7.96 (1H, t, J=7.9 Hz), 7.68 (1H, d, J=8.1 Hz), 7.42 (1H, d, J=9.5 Hz), 4.36 (2H, t, J=6.0 Hz), 3.45 (1H, bs), 3.05 (2H, s), 2.57-2.51 (2H, m), 2.20-2.12 (2H, m), 1.25 (6H, s).

Assays for Determining Biological Activity

Inhibition of Prostaglandin E Synthase Activity

Compounds are tested as inhibitors of prostaglandin E synthase activity in microsomal prostaglandin e synthases, whole cell and in vivo assays. These assays measure prostaglandin E2 (PGE2) synthesis using either Enzymatic Immunoassay (EIA) or mass spectrometry. Cells used for microsomal preparation are CHO—K1 cells transiently transfected with plasmids encoding the human mPGES-1 cDNA. Cells used for cell-based experiments are human A549 (which express human mPGES-1). Guinea pigs are used to test the activity of selected compounds in vivo. In all these assays, 100% activity is defined as the $PGE_2$ production in vehicle-treated samples. $IC_{50}$ and ED50 represent the concentration or dose of inhibitor required to inhibit $PGE_2$ synthesis by 50% as compared to the uninhibited control.

Microsomal Prostaglandin E Synthase Assay

Prostaglandin E synthase microsomal fractions are prepared from CHO—K1 cells transiently transfected with plasmid encoding the human mPGES-1 cDNA. Microsomes are then prepared and the PGES assay begins with the incubation of 5 μg/ml microsomal PGES-1 with compound or DMSO (final 1%) for 20-30 minutes at room temperature. The enzyme reactions are performed in 200 mM KPi pH 7.0, 2 mM EDTA and 2.5 mM GSH-reduced form. The enzymatic reaction is then initiated by the addition of 1 μM final $PGH_2$ substrate prepared in isopropanol (3.5% final in assay well) and incubated at room temperature for 30 seconds. The reaction is terminated by the addition of $SnCl_2$ in 1N HCl (1 mg/ml final). Measurement of $PGE_2$ production in the enzyme reaction aliquots is done by EIA using a standard commercially available kit (Cat #: 901-001 from Assay Designs).

Data from this assay for representative compounds is shown in the table below. The potency is expressed as $IC_{50}$ and the value indicated is an average of at least n=3.

| Ex. | h-CHO (nM) |
|---|---|
| 1 | 1.9 |
| 5 | 2.1 |
| 8 | 2 |
| 9 | 1.9 |
| 14 | 1.8 |
| 20 | 13.1 |
| 21 | 12 |
| 25 | 1.3 |
| 23 | 2.1 |
| 36 | 1.2 |
| 37 | 9.9 |
| 40 | 0.9 |
| 45 | 2534 |
| 46 | 1.5 |
| 48 | 0.9 |
| 51 | 4.8 |
| 55 | 1.1 |
| 56 | 1.7 |
| 65 | 1.5 |
| 68 | 1.5 |
| 73 | 1.7 |
| 76 | 3.7 |
| 87 | 1.9 |
| 88 | 1.3 |
| 91 | 1 |
| 93 | 1.2 |
| 95 | 2.4 |
| 98 | 0.9 |
| 99 | 1.2 |
| 117 | 0.7 |

Human A549 Whole Cell Prostaglandin E Synthase Assay

Rationale

Whole cells provide an intact cellular environment for the study of cellular permeability and biochemical specificity of anti-inflammatory compounds such as prostaglandin E synthase inhibitors. To study the inhibitory activities of these compounds, human A549 cells are stimulated with 10 ng/ml recombinant human IL-1β for 24 hours. The production of $PGE_2$ and $PGF_{2\alpha}$ are measured by EIA at the end of the incubation as readouts for selectivity and effectiveness against mPGES-1-dependent $PGE_2$ production.

Methods

Human A549 cells specifically express human microsomal prostaglandin E synthase-1 and induce its expression following treatment with IL-1β for 24 hours. $2.5 \times 10^4$ cells seeded in 100 ul/well (96-well plate) and incubated overnight under standard conditions. 100 ul of cell culture media containing 10 ng/ml IL-1β is then added to the cells followed by the addition of either 2% FBS containing RPMI or 50% FBS containing RPMI. 2 μl of drugs or vehicle (DMSO) are then added and samples are mixed immediately. Cells are incubated for 24 hours and following the incubation 175 μl of medium is harvested and assayed for $PGE_2$ and $PGF_{2\alpha}$ contents by EIA.

Human Whole Blood Prostaglandin E Synthase Assay

Rationale

Whole blood provides a protein and cell-rich milieu for the study of biochemical efficacy of anti-inflammatory compounds such as prostaglandin E synthase inhibitors. To study the inhibitory activities of these compounds, human blood is stimulated with lipopolysaccharide (LPS) for 24 hours to induce mPGEBS-1 expression. The production of pro staglandin E2 ($PGE_2$) and thromboxane B2 ($TxB_2$) are measured by EIA at the end of the incubation as readouts for selectivity and effectiveness against mPGES-1-dependent $PGE_2$ production.

Methods

Human whole blood assays for mPGES-1 activity reported (Brideau, et al., *Inflamm. Res.*, vol. 45, p. 68, 1996) are performed as described below.

Freshly isolated venous blood from human volunteers is collected in heparinized tubes. These subjects have no apparent inflammatory conditions and have not taken any NSAIDs for at least 7 days prior to blood collection. 250 μl of blood is pre-incubated with 1 ul vehicle (DMSO) or 1 ul of test compound. Bacterial LPS at 100 μg/ml (*E. Coli* serotype 0111:B4 diluted in 0.1% w/v bovine serum albumin in phosphate buffered saline) is then added and samples are incubated for 24 hours at 37° C. Unstimulated control blood at time zero (no LPS) is used as blank. At the end of the 24 hr incubation, the blood is centrifuged at 3000 rpm for 10 min at 4° C. The plasma is assayed for $PGE_2$ and $TxB_2$ using an EIA kit as indicated above.

In vivo Determination of Anti-Inflammatory Activity

Rationale

The whole animal provides an integrated physiological system to confirm the anti-inflammatory activity of test compounds characterized in vitro. To determine the activity of prostaglandin E synthase inhibitors in vivo, animals are dosed with compounds either prior or after the inflammatory stimulus, LPS. LPS is injected into the hind paw of guinea pigs and hyperalgesia measurements are recorded 4.5 and/or 6 hrs after the injection.

Formulation of Test Compounds for Oral Dosage

Test compound was ground and made amorphous using a ball milling system. The compound was placed in an agate jar containing agate balls and spun at high speed for 10 minutes in an apparatus such as the Planetary Micro Mill Pulverisette 7 system. The jar was then opened and 0.5% methocel solution was added to the ground solid. This mixture was spun again at high speed for 10 minutes. The resulting suspension was transferred to a scintillation vial, diluted with the appropriate amount of 0.5% methocel solution, sonicated for 2 minutes and stirred until the suspension was homogeneous. Alternatively, the test compound can be formulated using amorphous material obtained by any suitable chemical or mechanical technique. This amorphous solid is then mixed and stirred for a certain period of time, such as 12 hours, with a suitable vehicle, such as 0.5% methocel with 0.02 to 0.2% of sodium dodecylsulfate, prior to dosage.

Methods

Male Hartley guinea pigs, weighing 200-250 grams were used. LPS (30 mg/kg) is injected sub-plantarly into the left hind paw of the guinea pig to produce hyperalgesia in the injected paw. Rectal temperature and paw withdrawal latency, a measure of hypersensitivity to pain (hyperalgesia), are taken prior to LPS injection and used as the baseline. Paw withdrawal latency is determined using the thermal hyperalgesia instrument (Ugo Basile Corp.). During this determination, animals are placed in an 8"×8" plexiglas holding box atop of a glass base. A mild (223 mW/cm²) infrared light is directed toward the underside of the hind paw. The time it takes for the animal to remove its paw (indication that it feels the pain caused by the heat) is recorded. The infrared light immediately shuts off when the animal withdraws its paw from the area. The light will also shut off automatically when the time reaches 20 seconds.

Predose Paradigm:

Test compounds are orally dosed at 5 ml/kg using an 18-gauge feeding needle. LPS (serotype 0111:B4, 10 μg) or 0.9% saline is injected into the plantar region of the left hind paw at a volume of 100 μl using a 26 gauge needle 1 hour following compound administration. Rectal temperature and thermal paw withdrawal latency are taken 4.5 hours after LPS administration. The animals are euthanized following the measurements using $CO_2$ and lumbar spinal cord, hind paw and blood samples collected.

Reversal Paradigm:

Thermal paw withdrawal of each animal is determined before and 3 hours following sub-plantar injection of LPS. Animals which have received LPS and do not show a decrease in withdrawal latency at the 3 hour time point will be removed from study and euthanized. Test compounds are dosed p.o. at 5 ml/kg immediately following the thermal paw withdrawal measurement. Thermal withdrawal latency is taken 1.5 and 3 hours following compound administration (4.5 and 6 hours post-LPS administration). After the final reading, the animals are euthanized using CO2 and lumbar spinal cord and blood samples collected for prostaglandin determination by mass spectrometry and drug level, respectively.

The invention also encompasses a genus of compounds represented by Formula I

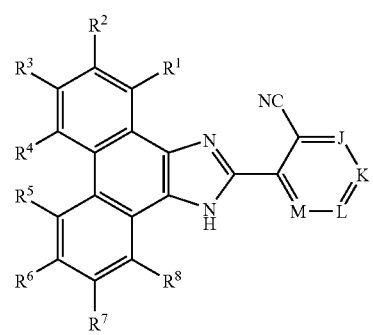

or a prodrug thereof, or a pharmaceutically acceptable salt of said compound or prodrug, wherein:

J is selected from the group consisting of —$C(X^2)$— and —N—,

K is selected from the group consisting of —C(X³)— and —N—,

L is selected from the group consisting of —C(X⁴)— and —N—, and

M is selected from the group consisting of —C(X⁵)— and —N—, with the proviso that at least one of J, K, L or M is other than —N—;

X², X³, X⁴ and X⁵ are independently selected from the group consisting of: (1) H; (2) —CN; (3) F; (4) Cl; (5) Br; (6) I; (7) —OH; (8) —N₃; (9) C₁₋₆alkyl, C₂₋₆alkenyl or C₂₋₆alkynyl, wherein one or more of the hydrogen atoms attached to said C₁₋₆alkyl, C₂₋₆alkenyl or C₂₋₆alkynyl may be replaced with a fluoro atom, and said C₁₋₆alkyl, C₂₋₆alkenyl or C₂₋₆alkynyl may be optionally substituted with a hydroxy group; (10) C₁₋₄alkoxy; (11) NR⁹R¹⁰—C(O)—C₁₋₄alkyl-O—; (12) C₁₋₄alkyl-S(O)ₖ—; (13) —NO₂; (14) C₃₋₆cycloalkyl, (15) C₃₋₆cycloalkoxy; (16) phenyl, (17) carboxy; and (18) C₁₋₄alkyl-O—C(O)—;

R¹, R², R³, R⁴, R⁵, R⁶, R⁷ and R⁸ are independently selected from the group consisting of: (1) H; (2) F; (3) Cl; (4) Br; (5) I; (6) —CN; (7) C₁₋₁₀alkyl or C₂₋₁₀alkenyl, wherein one or more of the hydrogen atoms attached to said C₁₋₁₀alkyl or C₂₋₁₀alkenyl may be replaced with a fluoro atom, or two hydrogen on adjacent carbon atoms may be joined together and replaced with —CH₂— to form a cyclopropyl group, or two hydrogen atoms on the same carbon atom may be replaced and joined together to form a spiro C₃₋₆cycloalkyl group, and wherein said C₁₋₁₀alkyl or C₂₋₁₀alkenyl may be optionally substituted with one to three substituents independently selected from the group consisting of: —OH, acetyl, methoxy, ethenyl, R¹¹—O—C(O)—, R³⁵—N(R³⁶)—, R³⁷—N(R³⁸)—C(O)—, cyclopropyl, pyrrolyl, imidiazolyl, pyridyl and phenyl, said pyrrolyl, imidiazolyl, pyridyl and phenyl optionally substituted with C₁₋₄alkyl or mono-hydroxy substituted C₁₋₄alkyl; (8) C₃₋₆cycloalkyl; (9) R¹²—O—; (10) R¹³—S(O)ₖ—, (11) R¹⁴—S(O)ₖ—N(R¹⁵)—; (12) R¹⁶—C(O)—; (13) R¹⁷—N(R¹⁸)—; (14) R¹⁹—N(R²⁰)—C(O)—; (15) R²¹—N(R²²)—S(O)ₖ—; (16) R²³—C(O)—N(R²⁴)—; (17) Z-C≡C; (18) —(CH₃)C=N—OH or —(CH₃)C=N—OCH₃; (19) R³⁴—O—C(O)—; (20) R³⁹—C(O)—O—; and (21) phenyl, naphthyl, pyridyl, pyradazinyl, pyrimidinyl, pyrazinyl, pyrrolyl, pyrazolyl, imidazolyl, triazolyl, tetrazolyl, oxazolyl, isoxazolyl, oxadiazolyl, thienyl or furyl, each optionally substituted with a substituent independently selected from the group consisting of: F, Cl, Br, I, C₁₋₄alkyl, phenyl, methylsulfonyl, methylsulfonylamino, R²⁵—O—C(O)— and R²⁶—N(R²⁷)—, said C₁₋₄alkyl optionally substituted with 1 to 3 groups independently selected from halo and hydroxy;

each Z is independently selected from the group consisting of: (1) H; (2) C₁₋₆alkyl, wherein one or more of the hydrogen atoms attached to said C₁₋₆alkyl may be replaced with a fluoro atom, and wherein C₁₋₆alkyl is optionally substituted with one to three substituents independently selected from: hydroxy, methoxy, cyclopropyl, phenyl, pyridyl, pyrrolyl, R²⁸—N(R²⁹)— and R³⁰—O—C(O)—; (3) —(CH₃)C=N—OH or —(CH₃)C=N—OCH₃; (4) R³¹—C(O)—; (5) phenyl; (6) pyridyl or the N-oxide thereof; (7) C₃₋₆cycloalkyl, optionally substituted with hydroxy; (8) tetrahydropyranyl, optionally substituted with hydroxy; and (9) a five-membered aromatic heterocycle containing 1 to 3 atoms independently selected from O, N or S and optionally substituted with methyl;

each R⁹, R¹⁰, R¹⁵, R²⁴ and R³² is independently selected from the group consisting of: (1) H; and (2) C₁₋₄alkyl;

each R¹¹, R¹², R¹³, R¹⁴, R¹⁶, R²³, R²⁵, R³⁰, R³¹, R³⁴ and R³⁹ is independently selected from the group consisting of: (1) H; (2) C₁₋₄alkyl, (3) C₃₋₆cycloalkyl; (4) C₃₋₆cycloalkyl-C₁₋₄ alkyl- (5) phenyl, (6) benzyl; and (7) pyridyl; said C₁₋₄alkyl, C₃₋₆cycloalkyl, C₃₋₆cycloalkyl-C₁₋₄alkyl-, phenyl, benzyl and pyridyl may each be optionally substituted with 1 to 3 substituents independently selected from the group consisting of: OH, F, Cl, Br and I, and wherein said C₁₋₄alkyl may be further substituted with oxo or methoxy or both;

each R¹⁷, R¹⁸, R¹⁹, R²⁰, R²¹, R²², R²⁶, R²⁷, R²⁸, R²⁹, R³⁵, R³⁶, R³⁷ and R³⁸ is independently selected from the group consisting of: (1) H; (2) C₁₋₆alkyl; (3) C₁₋₆alkoxy; (4) OH and (5) benzyl or 1-phenylethyl; and R¹⁷ and R¹⁸, R¹⁹ and R²⁰, R²¹ and R²², R²⁶ and R²⁷, and R²⁸ and R²⁹, R³⁵ and R³⁶, and R³⁷ and R³⁸ may be joined together with the nitrogen atom to which they are attached to form a monocyclic ring of 5 or 6 carbon atoms, optionally containing one or two atoms independently selected from —O—, —S(O)ₖ— and —N(R³²)—; and each k is independently 0, 1 or 2.

Within this genus, the invention encompasses a sub-genus of compounds of Formula B:

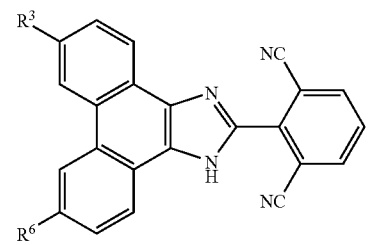

or a prodrug thereof, or a pharmaceutically acceptable salt of said compound or prodrug, wherein:

R³ is 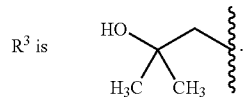

Within this sub-genus, the invention encompasses a class of compounds wherein R⁶ is R¹²—O. Within this class, the invention encompasses a sub-class of compounds wherein R¹² is selected from the group consisting of: (1) C₁₋₄alkyl and (2) C₃₋₆cycloalkyl-C₁₋₄alkyl-, said C₁₋₄alkyl and C₃₋₆cycloalkyl may each be optionally substituted with 1 to 3 substituents independently selected from the group consisting of: OH, F, Cl, Br and I.

The invention also encompasses a class of compound within the sub-genus wherein R⁶ is selected from F, Cl, Br and I.

An alternate method for making Example 40 is as follows:

Alternate Example 40

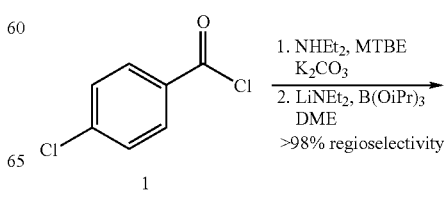

1

-continued

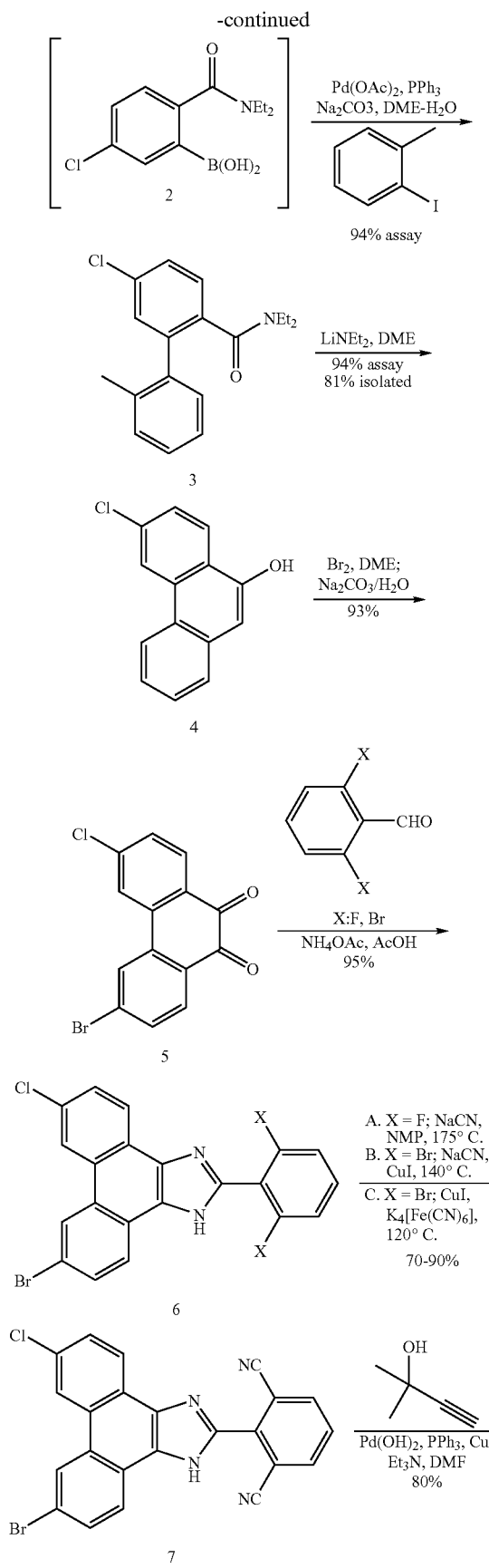

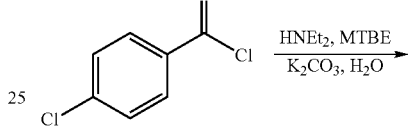

Example 40

Experimental Procedure

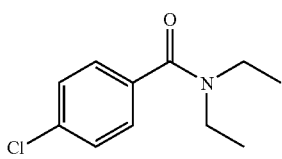

To a round bottom flask was charged potassium carbonate (65 g, 469.7 mmol), H$_2$O (400 mL), MTBE (800) and diethyl amine (81 mL, 861.1 mmol). p-Chlorobenzoyl chloride (100 mL, 782.8 mmol) was then added over 30 minutes, maintaining the temperature under 25° C. After addition, the phases were separated and the organics washed with brine (200 mL). The solution was then solvent switched to DME to give a crude solution of the amide, which was used directly in the next step.

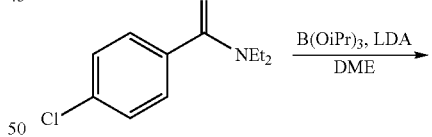

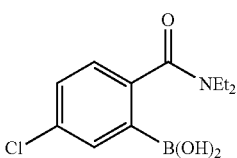

To the crude solution of the amide (10 g, 47.3 mmol) in 7.5 mL/g DME (75 mL) was added triisopropyl borate (19.5 mL, 85.1 mmol) and the resulting solution was cooled to −25° C. A freshly prepared 1.45 M solution of lithium diethylamide (45.6 mL, 66.2 mmol) was then added dropwise over 30 minutes. [NOTE: Lithium diethylamide was generated by treatment of diethylamine in THF with a 2.5M solution of n-butyllithium in hexanes, maintaining the temperature below 0° C. during the addition] At the end of addition, the mixture was aged for additional 15 minutes, at which all starting material has been consumed to give the corresponding boronic acid in >98% regioselectivity. The crude solution was then used directly in the next step.

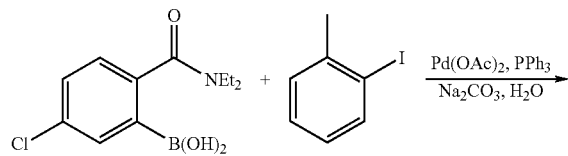

To the crude solution of boronic acid as obtained above was added degassed water (95 mL) at 0° C. and solid Na$_2$CO$_3$ (13.5 g, 127.7 mmol). To the resulting suspension was successively added PPh$_3$ (223 mg, 0.85 mmol), 2-iodotoluene (5.4 mL, 42.6 mmol) and Pd(OAc)$_2$ (95.5 mg, 0.43 mmol) and the mixture was degassed, heated to 70° C. and aged for 6 hours, at which complete consumption of 2-iodotoluene was typically observed. At the end of reaction, MTBE (75 mL) was added and the resulting slurry was filtered. Sodium chloride was added to the biphasic filtrate to ease the separation and the layers were cut. The organic phase washed one time with water (20 mL) and brine (2×30 mL). The crude solution was then concentrated, solvent switched to DME and used directly in the next step. Typical assay yield: 90-94%.

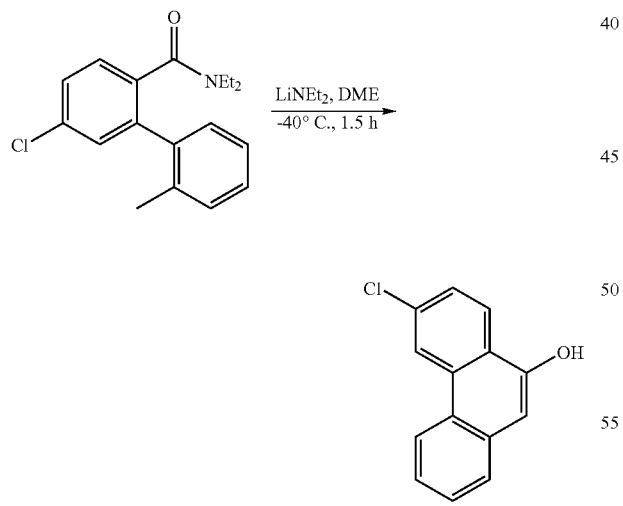

To the crude solution of the amide (13.9 g, 46.2 mmol) in 7.5 mL/g DME (104 mL), kept at −45° C., was added freshly prepared 1.44 M solution of LiNEt$_2$ in THF (41.7 mL, 60 mmol) over 15 min. The resulting brown solution was aged for 75 minutes, at which complete consumption of starting material was observed by HPLC. MTBE (120 mL) was added followed by slow addition of 6N HCl (30.8 mL, 184.7 mmol). The resulting mixture was allowed to warm to RT and the layers were separated (pH of the aqueous layer should be 2-3). The organic layer washed one time with H$_2$O (55 mL), brine (60 mL), concentrated and solvent switched to toluene for crystallization. When approximately 4 mL/g of product in a 3:1 mixture of toluene:DME was obtained, the slurry was refluxed to dissolve all the solid, cooled slowly to 60° C. and treated with 5 mL/g of methyl cyclohexane (crystals are typically formed at 75-80° C.) over 1 hour, while allowing the mixture to cool to RT. The slurry was then concentrated to give a volume of 3.5 mL/g of product and then re-treated with 2 mL/g of methyl cyclohexane over 0.5 hour. The slurry was aged at 0° C. for 0.5 hour, filtered and the wetcake washed with a cold 3:1 mixture of toluene:methyl cyclohexane, followed by drying under constant flow of N$_2$. The desired product was obtained as light tan solid in 81% yield.

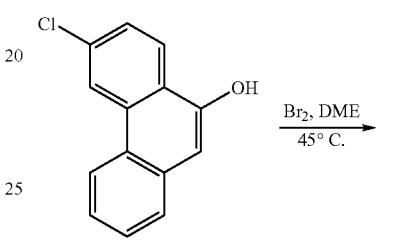

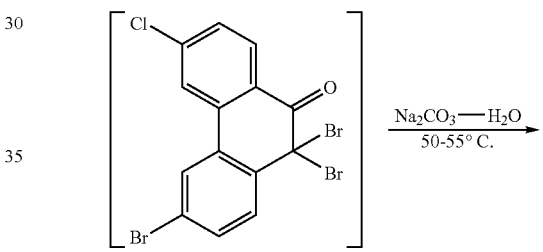

To a solution of chloro-phenanthrole (41 g, 179.8 mmol) in dry DME (600 mL, KF=25 ppm, solution KF=1000 ppm) at 15° C. was added Br$_2$ (32.3 mL, 629.4 mmol) over 20 minutes, at which a 15° C. exotherm was evident during the addition. The resulting suspension was then warmed to 40-45° C. and aged for 4 hours to give a clear, red solution. A solution of Na$_2$SO$_3$ (4.4 g, 36 mmol) in 30 mL of H$_2$O was added, followed by a solution of Na$_2$CO$_3$ (57 g, 539.4 mmol) in 250 mL H$_2$O. The resulting suspension was warmed to 55° C. and aged for 5 hour, at which a complete hydrolysis was obtained (additional of H$_2$O might be necessary to re-dissolve precipitated Na$_2$CO$_3$). The reaction mixture was then concentrated at 35-40° C. (35-40 torr) to about a third of its volume and the slurry was filtered, washed with H$_2$O (80-100 mL), followed by 1:1 DME:H$_2$O (100 mL) and dried under constant flow of N₂. The solid obtained was generally pure enough for the next step; typical yield: 93%.

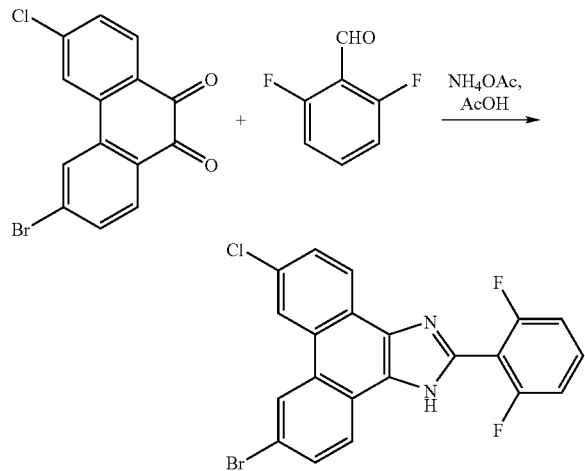

The chlorobromodiketone (4.54 g, 14.12 mmol), difluorobenzaldehyde (1.5 mL, 14.12 mmol), and ammonium acetate (21.77 g, 282.38 mmol) were charged to a 250 mL round bottom three neck flask under nitrogen. Acetic acid (90 mL) was added with stirring, and the slurry was heated to 120° C. for 1 hour. The slurry was then cooled to room temperature and water (90 mL) was added over 30 min. Upon completion of addition of water, the reaction mixture was filtered, washed with water (45 mL), and dried overnight under nitrogen and vacuum to give the acetic acid salt as a yellow solid.

In order to obtain the freebase, the crude product was dissolved in 1:1 THF/MTBE (90 mL) and charged to a 250 mL flask along with 1N NaOH (45 mL). The mixture was then heated to 40° C. for one hour. The phases were cut at 40° C., and the organic layer washed with 1N NaOH (45 mL). The organic layer was then concentrated, solvent switched to MTBE, and brought to a final volume of 45 mL. The reaction mixture was slurried at 35° C. for one hour, cooled to room temperature, filtered, washed with MTBE (23 mL), and dried under nitrogen. The difluoro imidazole freebase (5.97 g) was obtained as a light yellow solid in 95% isolated yield.

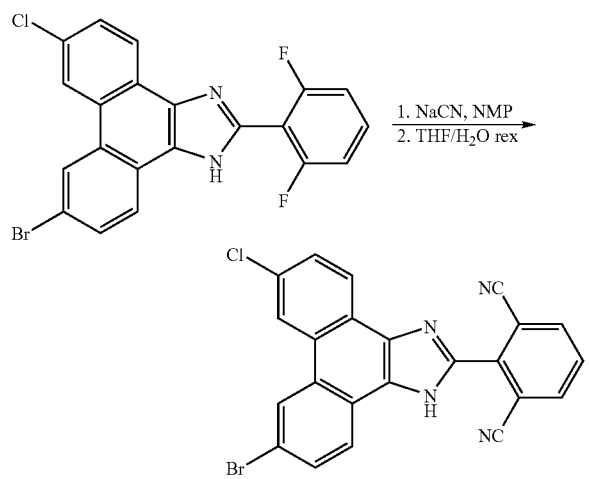

Method A: The difluoroimidazole (6.79 g, 13.39 mmol) and sodium cyanide (3.28 g, 66.95 mmol) were charged to a 500 mL round bottom flask under nitrogen. N-methylpyrrolidone (NMP, 60 mL) was added with stirring, and the slurry was heated to 175° C. for 28 hours. The reaction mixture was then cooled to room temperature. Water (240 mL) was added over 2 hours, and the slurry was allowed to stir for 48 hours. Sodium chloride (36 g) was added to the slurry and it was stirred for additional 2 hours. The slurry was then cooled to 0° C., stirred for 1 hour, filtered, and washed with water (30 mL). The wetcake was then dried under nitrogen to give the desired product as NMP solvate.

The solid was slurried in THF (42 mL, 7.5 mL/g) at 65° C. for 1 hour. The mixture was then cooled to room temperature, followed by addition of water (14 mL, 2.5 mL/g) over 1 hour. The slurry was then concentrated under vacuum, removing 14 mL of solvent and the resulting slurry was filtered. The wetcake washed with 1:1 THF/H2O (14 mL), and dried under nitrogen. The desired product (3.83 g) was obtained as THF solvate in 54% isolated yield.

Method B:

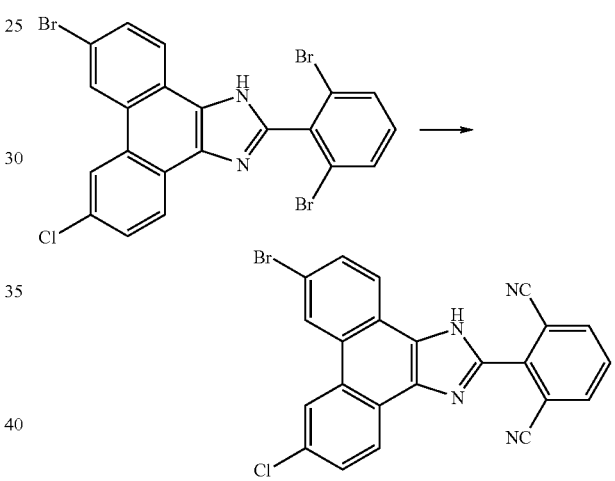

1.0 g of tribromoimidazole freebase (1.8 mmol), 260 mg NaCN (5.3 mmol), 135 mg CuI (0.71 mmol) and 7 mL DMF were combined and degassed, then heated to 120° C. for 45 h. 7 mL of 6:1 water:NH₄OH was added, and the crude product was isolated by filtration. After drying, the material was recrystallized from 1:1 THF:MTBE (16 mL) to afford 870 mg of the dicyano product as the THF solvate (97%).

Method C: tribromoimidazole AcOH salt (1.30 g, 87 wt % as free base, 2 mmol) was treated with K₄[Fe(CN)₆].3H₂O (845 mg, 2 mmol, finely-powdered), CuI (76.2 mg, 0.4 mmol), and 1,2-phenylenediamine (43.3 mg, 0.4 mmol) in DMF (5.7 mL). The reaction mixture was heated to 135° C. for 36 h, diluted with DMF (5.7 mL), and filtered when hot. The solid washed thoroughly with acetone, and the washes were combined with the filtrate. The organic solution was concentrated to remove acetone, and H₂O (2.8 mL) was added over 15 min at RT. The resulting solid was collected by filtration, washed with H₂O, and to afford brown solid (1.06 g). The crude solid was then stirred in THF (4 mL) at 60° C. for 1 h and allowed to cool to RT. The resulting solid was collected by filtration, washed with hexane, and dried to afford dicanide THF solvate as off white powder (864 mg, 89.5 wt %).

For Methods B and C above, the tribromoimidazole compound is made following the procedure described above for making the difluoroimidazole compound, but substituting dibromobenzaldehyde for difluorobenzaldehyde.

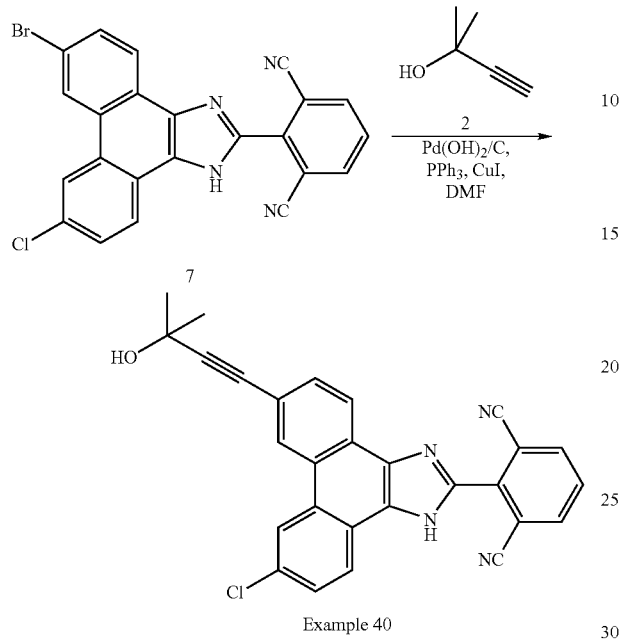

Example 40

A 7 ml vial, equipped with stir bar and septum screw cap was charged with 6.2 mg of 20 wt % Pd(OH)$_2$ on carbon containing about 16 wt % water (about 1.0 mg Pd(OH)$_2$ corrected for solid support and water), 69 mg compound 7, 8 mg triphenylphosphine, and 6 mg copper(I) iodide. The vial was brought into a nitrogen filled glovebox where the remaining nitrogen-purged reaction materials were added. N,N-Dimethylformamide (0.68 mL) was charged followed by 2-methyl-3-butyn-2-ol (0.022 mL) and triethylamine (0.031 mL). The vial was sealed, removed from the glovebox, placed in a heating block equipped with a nitrogen-purged cover attached, and warmed to an external temperature of 52° C. The reaction was agitated with heating for about 17 h. HPLC analysis of the reaction at this time showed about 95% LCAP conversion to Example 40 using an external reference with >99 LCAP conversion of bromide 7 @ 210 nm.

The following examples describe methods for making Example 40 as amorphous material.

Example A 2 grams of Example 40 solid and 10 ml of dimethyl solfoxide (DMSO) solvent were charged into a glass flask at room temperature. All solids were dissolved. The solution was mixed rapidly with 20 to 30 ml of water (as anti-solvent) using an impinging jet device, similar to the one disclosed in U.S. Pat. No. 5,314,506, granted May 24, 1994, to precipitate Example 40 as amorphous material. The ratio of DMSO to water ratio at the impingement ranges from 1/2 to 1/3. The resulting slurry was sent to a jacketed crystallizer which contained 30-20 ml of water under agitation. The final DMSO/water ratio is maintained at 1/5. The temperature of the batch was maintained at −5° C. to 5° C. to maintain the stability of amorphous solid of Example 40 in slurry. The slurry was filtered and washed with water at 0° C.-5° C. The wet cake was vacuum dried. The crystallinity of the cake was examined by X-ray diffraction analysis and light microscope. The residual solvent in the cake was analyzed by GC.

The amorphous solid of the light microscopic image are mainly non-birefringent with some birefringent crystals. GC analysis of the amorphous solid shows <0.5 wt % residual DMSO in the solid.

Example B

To a 125 mL jacketed crystallizer equipped with an IKA-Works rotor/stator homogenizer (model T25 with fine dispersion element) as the agitator, charge 50 mL DI water. Turn on the homogenizer at 9.1 m/s tip speed and adjust the jacket temperature until water temperature in vessel is 0° C. to 2° C. Dissolve 1 gram of Example 40 in 5 ml THF in a separate 50 ml glass flask, then add this solution to the above 125 ml crystallizer over 5 minutes. Following charge, adjust jacket temperature of the above crystallizer to achieve 0-2° C. batch temperature. Filter batch and wash with cold water. Dried sample was analyzed by XRD which confirmed that material was amorphous.

What is claimed is:

1. A compound represented by Formula I

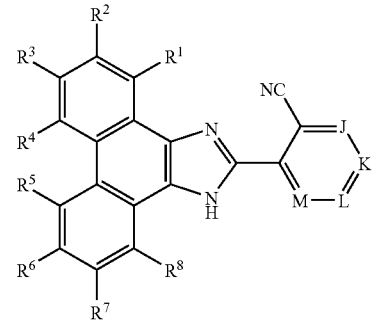

or a prodrug thereof, or a pharmaceutically acceptable salt of said compound or prodrug, wherein:

J is selected from the group consisting of —C($X^2$)— and —N—,

K is selected from the group consisting of —C($X^3$)— and —N—,

L is selected from the group consisting of —C($X^4$)— and —N—, and

M is selected from the group consisting of —C($X^5$)— and —N—, with the proviso that at least one of J, K, L or M is other than —N—;

$X^2$, $X^3$, $X^4$ and $X^5$ are independently selected from the group consisting of: (1) H; (2) —CN; (3) F; (4) Cl; (5) Br; (6) I; (7) —OH; (8) —$N_3$; (9) $C_{1-6}$alkyl, $C_{2-6}$alkenyl or $C_{2-6}$alkynyl, wherein one or more of the hydrogen atoms attached to said $C_{1-6}$alkyl, $C_{2-6}$alkenyl or $C_{2-6}$alkynyl may be replaced with a fluoro atom, and said $C_{1-6}$alkyl, $C_{2-6}$alkenyl or $C_{2-6}$alkynyl may be optionally substituted with a hydroxy group; (10) $C_{1-4}$alkoxy; (11) $NR^9R^{10}$—C(O)—$C_{1-4}$alkyl-O—; (12) $C_{1-4}$alkyl—S(O)$_k$—; (13) —$NO_2$; (14) $C_{3-6}$cycloalkyl, (15) $C_{3-6}$cycloalkoxy; (16) phenyl, (17) carboxy; and (18) $C_{1-4}$alkyl-O—C(O)—;

$R^1$, $R^2$, $R^3$, $R^4$, $R^5$, $R^6$, $R^7$ and $R^8$ are independently selected from the group consisting of: (1) H; (2) F; (3) Cl; (4) Br; (5) I; (6) —CN; (7) $C_{1-10}$alkyl or $C_{2-10}$alkenyl, wherein one or more of the hydrogen atoms attached to said $C_{1-10}$alkyl or $C_{2-10}$alkenyl may be replaced with a fluoro atom, or two hydrogen on adjacent carbon atoms may be joined together and replaced with —$CH_2$— to form a cyclopropyl group, or two hydrogen atoms on the same carbon atom may be replaced and joined together to form a spiro $C_{3-6}$cycloalkyl group, and wherein said $C_{1-10}$alkyl or $C_{2-10}$alkenyl may be optionally substituted with one to three substituents independently selected from the group consisting of: —OH, acetyl, methoxy, ethenyl, $R^{11}$—O—C(O)—, $R^{35}$—N($R^{36}$)—, $R^{37}$—N($R^{38}$)—C(O)—, cyclopropyl, pyrrolyl, imidiazolyl, pyridyl and phenyl, said pyrrolyl, imidiazolyl, pyridyl and phenyl optionally substituted with $C_{1-4}$alkyl or mono-hydroxy substituted $C_{1-4}$alkyl; (8) $C_{3-6}$cycloalkyl; (9) $R^{12}$—O—; (10) $R^{13}$—S(O)$_k$—, (11) $R^{14}$—S(O)$_k$—N($R^{15}$)—; (12) $R^{16}$—C(O)—; (13) $R^{17}$—N($R^{18}$)—; (14) $R^{19}$—N($R^{20}$)—C(O)—; (15) $R^{21}$—N($R^{22}$)—S(O)$_k$—; (16) $R^{23}$—C(O)—N($R^{24}$)—; (17) Z-C≡C; (18) —(CH$_3$)C=N—OH or —(CH$_3$)C=N—OCH$_3$; (19) $R^{34}$—O—C(O)—; (20) $R^{39}$—C(O)—O—; and (21) phenyl, naphthyl, pyridyl, pyradazinyl, pyrimidinyl, pyrazinyl, pyrrolyl, pyrazolyl, imidazolyl, triazolyl, tetrazolyl, oxazolyl, isoxazolyl, oxadiazolyl, thienyl or furyl, each optionally substituted with a substituent independently selected from the group consisting of: F, Cl, Br, I, $C_{1-4}$alkyl, phenyl, methylsulfonyl, methylsulfonylamino, $R^{25}$—O—C(O)— and $R^{26}$—N($R^{27}$)—, said $C_{1-4}$alkyl optionally substituted with 1 to 3 groups independently selected from halo and hydroxy;

each Z is independently selected from the group consisting of: (1) H; (2) $C_{1-6}$alkyl, wherein one or more of the hydrogen atoms attached to said $C_{1-6}$alkyl may be replaced with a fluoro atom, and wherein $C_{1-6}$alkyl is optionally substituted with one to three substituents independently selected from: hydroxy, methoxy, cyclopropyl, phenyl, pyridyl, pyrrolyl, $R^{28}$—N($R^{29}$)— and $R^{30}$—O—C(O)—; (3) —(CH$_3$)C=N—OH or —(CH$_3$)C=N—OCH$_3$; (4) $R^{31}$—C(O)—; (5) phenyl; (6) pyridyl or the N-oxide thereof; (7) $C_{3-6}$cycloalkyl, optionally substituted with hydroxy; (8) tetrahydropyranyl, optionally substituted with hydroxy; and (9) a five-membered aromatic heterocycle containing 1 to 3 atoms independently selected from O, N or S and optionally substituted with methyl;

each $R^9$, $R^{10}$, $R^{15}$, $R^{24}$ and $R^{32}$ is independently selected from the group consisting of: (1) H; and (2) $C_{1-4}$alkyl;

each $R^{11}$, $R^{12}$, $R^{13}$, $R^{14}$, $R^{16}$, $R^{23}$, $R^{25}$, $R^{30}$, $R^{31}$, $R^{34}$ and $R^{39}$ is independently selected from the group consisting of: (1) H; (2) $C_{1-4}$alkyl, (3) $C_{3-6}$cycloalkyl; (4) $C_{3-6}$cycloalkyl-$C_{1-4}$alkyl- (5) phenyl, (6) benzyl; and (7) pyridyl; said $C_{1-4}$alkyl, $C_{3-6}$cycloalkyl, $C_{3-6}$cycloalkyl-$C_{1-4}$alkyl-, phenyl, benzyl and pyridyl may each be optionally substituted with 1 to 3 substituents independently selected from the group consisting of: OH, F, Cl, Br and I, and wherein said $C_{1-4}$alkyl may be further substituted with oxo or methoxy or both;

each $R^{17}$, $R^{18}$, $R^{19}$, $R^{20}$, $R^{21}$, $R^{22}$, $R^{26}$, $R^{27}$, $R^{28}$, $R^{29}$, $R^{35}$, $R^{36}$, $R^{37}$ and $R^{38}$ is independently selected from the group consisting of: (1) H; (2) $C_{1-6}$alkyl; (3) $C_{1-6}$alkoxy; (4) OH and (5) benzyl or 1-phenylethyl; and $R^{17}$ and $R^{18}$, $R^{19}$ and $R^{20}$, $R^{21}$ and $R^{22}$, $R^{26}$ and $R^{27}$, and $R^{28}$ and $R^{29}$, $R^{35}$ and $R^{36}$, and $R^{37}$ and $R^{38}$ may be joined together with the nitrogen atom to which they are attached to form a monocyclic ring of 5 or 6 carbon atoms, optionally containing one or two atoms independently selected from —O—, —S(O)$_k$— and —N($R^{32}$)—; and each k is independently 0, 1 or 2.

2. A compound according to claim 1 represented by Formula I

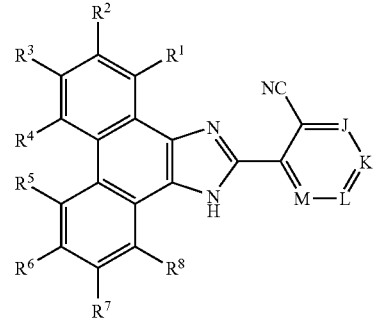

or a prodrug thereof, or a pharmaceutically acceptable salt of said compound or prodrug, wherein:

J is selected from the group consisting of —C($X^2$)— and —N—,

K is selected from the group consisting of —C($X^3$)— and —N—,

L is selected from the group consisting of —C($X^4$)— and —N—, and

M is selected from the group consisting of —C($X^5$)— and —N—, with the proviso that at least one of J, K, L or M is other than —N—;

$X^2$, $X^3$, $X^4$ and $X^5$ are independently selected from the group consisting of: (1) H; (2) —CN; (3) F; (4) Cl; (5) Br; (6) I; (7) —H; (8) —N$_3$; (9) $C_{1-6}$alkyl, $C_{2-6}$alkenyl or $C_{2-6}$alkynyl, wherein one or more of the hydrogen atoms attached to said $C_{1-6}$alkyl, $C_{2-6}$alkenyl or $C_{2-6}$alkynyl may be replaced with a fluoro atom, and said $C_{1-6}$alkyl, $C_{2-6}$alkenyl or $C_{2-6}$alkynyl may be optionally substituted with a hydroxy group; (10) $C_{1-4}$alkoxy; (11) NR$^9$R$^{10}$—C(O)—$C_{1-4}$alkyl-O—; (12) $C_{1-4}$alkyl-S(O)$_k$—; (13) —NO$_2$; (14) $C_{3-6}$cycloalkyl, (15) $C_{3-6}$cycloalkoxy; (16) phenyl, (17) carboxy; and (18) $C_{1-4}$alkyl-O—C(O)—;

$R^1$, $R^2$, $R^3$, $R^4$, $R^5$, $R^6$, $R^7$ and $R^8$ are independently selected from the group consisting of: (1) H; (2) F; (3) Cl; (4) Br; (5) I; (6) —CN; (7) $C_{1-6}$alkyl or $C_{2-6}$alkenyl, wherein one or more of the hydrogen atoms attached to said $C_{1-6}$alkyl or $C_{2-6}$alkenyl may be replaced with a fluoro atom, and wherein said $C_{1-6}$alkyl or $C_{2-6}$alkenyl may be optionally substituted with one to three substituents independently selected from the group consisting of: —OH, methoxy, $R^{11}$—O—C(O)—, cyclopropyl, pyridyl and phenyl; (8) $C_{3-6}$cycloalkyl; (9) $R^{12}$—O—; (10) $R^{13}$—S(O)$_k$—, (11) $R^{14}$—S(O)$_k$—N($R^{15}$)—; (12) $R^{16}$—C(O)—; (13) $R^{17}$—N($R^{18}$)—; (14) $R^{19}$—N($R^{20}$)—C(O)—; (15) $R^{21}$—N($R^{22}$)—S(O)$_k$—; (16) $R^{23}$—C(O)—N($R^{24}$)—; (17) Z-C≡C;

(18) —(CH$_3$)C=N—OH or —(CH$_3$)C=N—OCH$_3$; and (19) phenyl, naphthyl, pyridyl, pyradazinyl, pyrimidinyl, pyrazinyl, pyrrolyl, pyrazolyl, imidazolyl, triazolyl, tetrazolyl, oxazolyl, isoxazolyl, oxadiazolyl, thienyl or furyl, each optionally substituted with a substituent independently selected from the group consisting of: F, Cl, Br, I, $C_{1-14}$alkyl, phenyl, methylsulfonyl, methylsulfonylamino, $R^{25}$—O—C(O)— and $R^{26}$—N($R^{27}$)—, said $C_{1-4}$alkyl optionally substituted with 1 to 3 groups independently selected from halo and hydroxy;

each Z is independently selected from the group consisting of: (1) H; (2) $C_{1-6}$alkyl, wherein one or more of the hydrogen atoms attached to said $C_{1-6}$alkyl may be replaced with a fluoro atom, and wherein $C_{1-6}$alkyl is optionally substituted with one to three substituents independently selected from: hydroxy, methoxy, cyclopropyl, phenyl, pyridyl, pyrrolyl, $R^{28}$—N($R^{29}$)— and $R^{30}$—O—C(O)—; (3) —($CH_3$)C=N—OH or —($CH_3$)C=N—$OCH_3$; (4) $R^{31}$—C(O)—; (5) phenyl; (6) pyridyl or the N-oxide thereof; (7) $C_{3-6}$cycloalkyl, optionally substituted with hydroxy; (8) tetrahydropyranyl, optionally substituted with hydroxy; and (9) a five-membered aromatic heterocycle containing 1 to 3 atoms independently selected from O, N or S and optionally substituted with methyl;

each $R^9$, $R^{10}$, $R^{15}$, $R^{24}$ and $R^{32}$ is independently selected from the group consisting of: (1) H; and (2) $C_{1-4}$alkyl;

each $R^{11}$, $R^{12}$, $R^{13}$, $R^{14}$, $R^{16}$, $R^{23}$, $R^{25}$, $R^{30}$ and $R^{31}$ is independently selected from the group consisting of: (1) H; (2) $C_{1-4}$alkyl, (3) $C_{3-6}$cycloalkyl; (4) phenyl, (5) benzyl; and (6) pyridyl; said $C_{1-4}$alkyl, $C_{3-6}$cycloalkyl, phenyl, benzyl and pyridyl may each be optionally substituted with 1 to 3 substituents independently selected from the group consisting of: OH, F, Cl, Br and I;

each $R^{17}$, $R^{18}$, $R^{19}$, $R^{20}$, $R^{21}$, $R^{22}$, $R^{26}$, $R^{27}$, $R^{28}$ and $R^{29}$ is independently selected from the group consisting of: (1) H; (2) $C_{1-6}$alkyl; (3) $C_{1-6}$alkoxy; (4) OH and (5) benzyl or 1-phenylethyl; and $R^{17}$ and $R^{18}$, $R^{19}$ and $R^{20}$, $R^{21}$ and $R^{22}$, $R^{26}$ and $R^{27}$, and $R^{28}$ and $R^{29}$ may be joined together with the nitrogen atom to which they are attached to form a monocyclic ring of 5 or 6 carbon atoms, optionally containing one or two atoms independently selected from —O—, —S(O)$_k$— and —N($R^{32}$)—; and each k is independently 0, 1 or 2.

3. A compound according to claim 2 according to Formula A

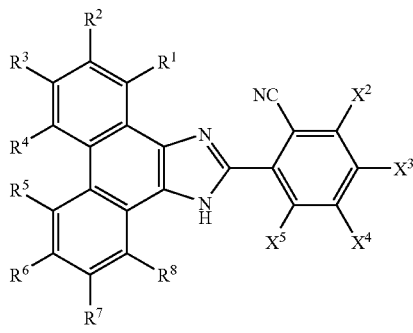

or a prodrug thereof, or a pharmaceutically acceptable salt of said compound or prodrug.

4. The compound according to claim 3 wherein:
$X^2$, $X^3$, $X^4$ and $X^5$ are independently selected from the group consisting of: (1) H; (2) —CN; (3) F; (4) Cl; (5) Br; and (6) I.

5. The compound according to claim 3, wherein $X^2$, $X^3$ and $X^4$ are H, and $X^5$ is other than H.

6. The compound according to claim 5, wherein $X^5$ is —CN.

7. The compound according to claim 3, wherein at least one of $R^1$ or $R^8$ is other than H.

8. The compound according to claim 3 wherein at least one of $R^2$ or $R^7$ is other than H.

9. The compound according to claim 3 wherein at least one of $R^4$ or $R^5$ is other than H.

10. The compound according to claim 3 wherein:
at least one of $R^3$ or $R^6$ is other than H; and
$R^1$, $R^2$, $R^4$, $R^5$, $R^7$ and $R^8$ are H.

11. The compound according to claim 10, wherein $R^3$ and $R^6$ are both other than H.

12. The compound according to claim 11, wherein:
one of $R^3$ or $R^6$ is independently selected from the group consisting of: F, Cl, Br, and I; and
the other of $R^3$ or $R^6$ is Z-C≡C.

13. The compound according to claim 10, wherein: $R^3$ and $R^6$ are independently selected from the group consisting of: hydrogen, fluoro, chloro, bromo, iodo, cyano, methyl, ethyl, vinyl, cyclopropyl, —$CO_2$i-Pr, —$CO_2CH_3$, —$SO_2CF_3$, 3-pyridyl, acetyl,

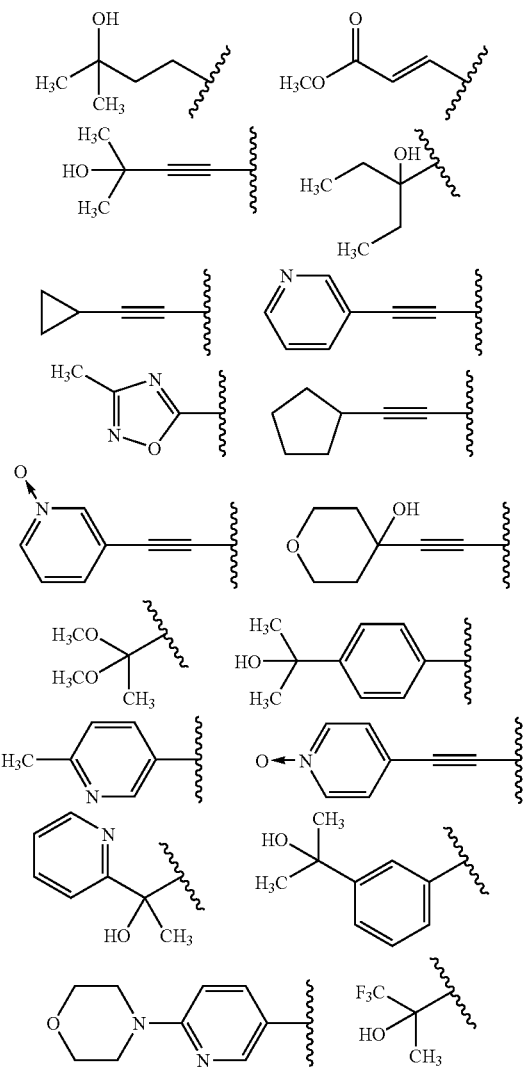

-continued

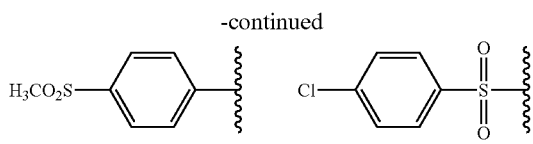

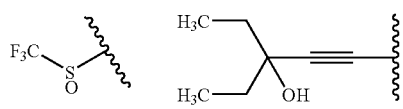

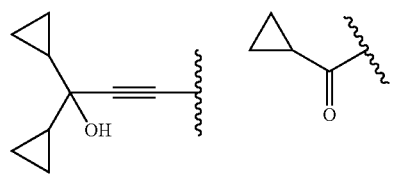

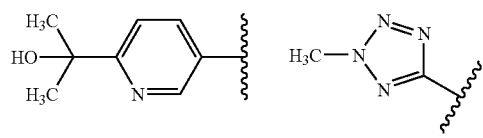

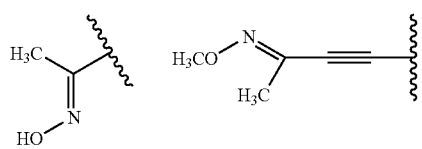

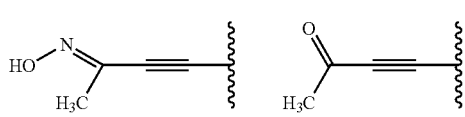

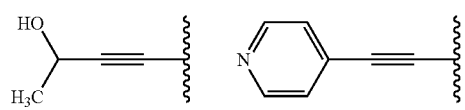

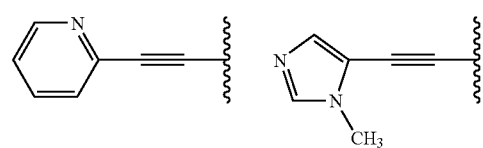

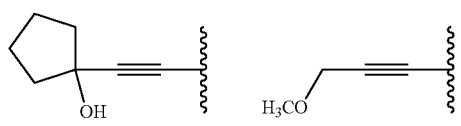

-continued

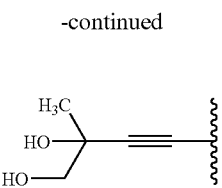

with the proviso that at least one of $R^3$ or $R^6$ is other than hydrogen.

14. The compound according to claim 2 according to Formula B:

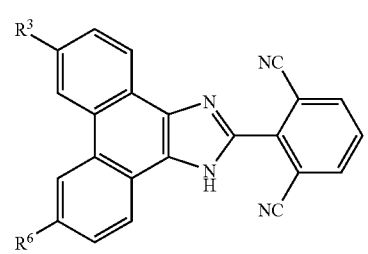

B or a prodrug thereof, or a pharmaceutically acceptable salt of said compound or prodrug.

15. The compound according to claim 14 wherein:
one of $R^3$ or $R^6$ is independently selected from the group consisting of: F, Cl, Br, and I; and
the other of $R^3$ or $R^6$ is Z-C≡C.

16. A prodrug of a compound according to claim 1 of Formula C

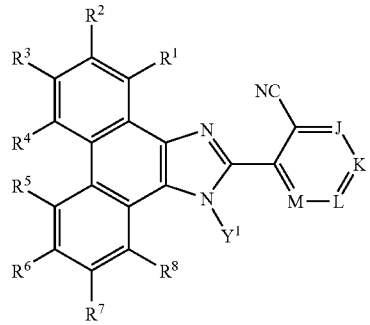

C or a pharmaceutically acceptable salt thereof, wherein:
$Y^1$ is selected from the group consisting of: (1) $C_{1-6}$alkyl; (2) $PO_4$—$C_{1-4}$alkyl-; (3) $C_{1-4}$alkyl-C(O)—O—$CH_2$—, wherein the $C_{1-4}$alkyl portion is optionally substituted with $R^{33}$—O—C(O)—; and (4) $C_{1-4}$alkyl-O—C(O)—; and $R^{33}$ is selected from the group consisting of: (1) H; (2) $C_{1-4}$alkyl, (3) $C_{3-6}$cycloalkyl; (4) phenyl; (5) benzyl; and (6) pyridyl; said $C_{1-4}$alkyl, $C_{3-6}$cycloalkyl, phenyl, benzyl and pyridyl may each be optionally substituted with 1 to 3 substituents independently selected from the group consisting of: OH, F, Cl, Br and I.

17. A compound according to claim 1 selected from one of the following tables:

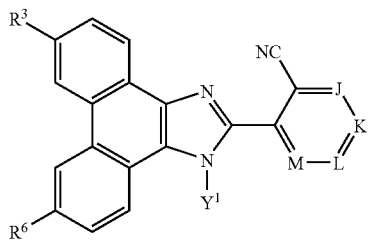

| Ex | R³/R⁶ | R⁶/R³ | J | K | L | M | Y¹ |
|---|---|---|---|---|---|---|---|
| 1 | Cl | Br | CH | CH | CH | CF | H |
| 2 | H | H | CH | CH | CH | CH | H |
| 3 | CN | F₃C−C(OH)−CF₃ | CH | CH | CH | CF | H |
| 4 | Cl | F₃C−C(OH)−CF₃ | CH | CH | CH | CF | H |
| 5 | Cl | H | CH | CH | CH | CF | H |
| 6 | CN | H | CH | CH | CH | CF | H |
| 7 | CN | F₃C−C(OH)−CH₃ | CH | CH | CH | CF | H |
| 8 | Cl | F₃C−C(OH)−CH₃ | CH | CH | CH | CF | H |
| 9 | Br | Br | CH | CH | CH | CF | H |
| 10 | H | H | CH | CH | CH | CCl | H |
| 11 | H | H | CH | CH | CH | CCN | H |
| 12 | H₃C−C(OH)(CH₃)−C≡C− | Br | CH | CH | CH | CF | H |
| 13 | H₃C−C(OH)(CH₃)−C≡C− | H₃C−C(OH)(CH₃)−C≡C− | CH | CH | CH | CF | H |
| 14 | H₃C−C(OH)(CH₃)−C≡C− | Cl | CH | CH | CH | CF | H |
| 15 | H₃C−C(OH)(CH₃)−C≡C− | I | CH | CH | CH | CF | H |
| 16 | H | H | CH | CH | CH | CBr | H |
| 17 | H | H | CH | CH | CH | CF | H |
| 18 | H | H | CH | N | CH | CCl | H |
| 19 | 3-pyridyl | 3-pyridyl | CH | CH | CH | CF | H |

-continued

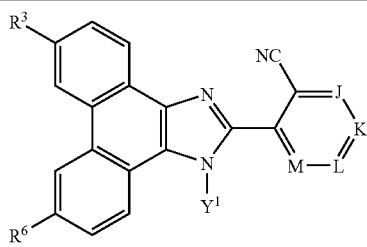

| Ex | R³/R⁶ | R⁶/R³ | J | K | L | M | Y¹ |
|---|---|---|---|---|---|---|---|
| 20 | Cl | H₃C-C(=O)- | CH | CH | CH | CF | H |
| 21 | Cl | (H₃C)(HO)(H₃C)C- | CH | CH | CH | CF | H |
| 22 | 3-pyridyl-C≡C- | Br | CH | CH | CH | CF | H |
| 23 | Cl | H | CH | N | CH | CCN | H |
| 24 | H | H | CH | N | CH | CCN | H |
| 25 | Cl | H | CH | CH | CH | CCN | H |
| 26 | H | H | CH | N | CH | CH | H |
| 27 | HO-CH(CH₃)-C≡C- | Br | CH | CH | CH | CF | H |
| 28 | H₃C-C(=O)-C≡C- | Br | CH | CH | CH | CF | H |
| 29 | H₃C-C(=O)- | H₃C-C(=O)- | CH | CH | CH | CF | H |
| 30 | (H₃C)(HO)(H₃C)C-C≡C- | H₃C-C(=O)- | CH | CH | CH | CF | H |
| 31 | H | H | N | CH | CH | N | H |
| 32 | H | H | N | CH | CH | CH | H |
| 33 | Br | H₃C-C(=O)- | CH | CH | CH | CF | H |
| 34 | I | I | CH | CH | CH | CF | H |
| 35 | Br | (H₃C)(HO)(H₃C)C- | CH | CH | CH | CF | H |
| 36 | Br | Cl | CH | CH | CH | CCN | H |

-continued

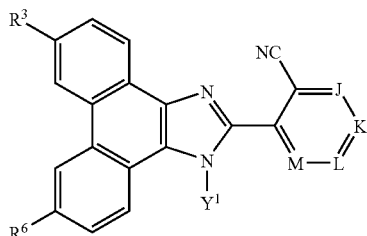

| Ex | R³/R⁶ | R⁶/R³ | J | K | L | M | Y¹ |
|---|---|---|---|---|---|---|---|
| 37 | Cl | H₃C-C(=O)- | CH | CH | CH | CBr | H |
| 38 | Cl | H₃C-C(=O)- | CH | CH | CH | CCN | H |
| 39 | I | I | CH | CH | CH | CCN | H |
| 40 | HOC(CH₃)₂-C≡C- | Cl | CH | CH | CH | CCN | H |
| 41 | Cl | HOC(CH₃)₂- | CH | CH | CH | CCN | H |
| 42 | HOC(CH₃)₂-C≡C- | I | CH | CH | CH | CCN | H |
| 43 | HOC(CH₃)₂-C≡C- | HOC(CH₃)₂-C≡C- | CH | CH | CH | CCN | H |
| 44 | H | H | CH | CH | CH | CCN | CO₂Et |
| 45 | H | H | CH | CH | CH | CCN | H₃C-CH₂-C(=O)-O-Et |
| 46 | H₃CO-CH₂-C≡C- | Cl | CH | CH | CH | CCN | H |
| 47 | 3-pyridyl-C≡C- | Cl | CH | CH | CH | CCN | H |
| 48 | 1-hydroxycyclopentyl-C≡C- | Cl | CH | CH | CH | CCN | H |
| 49 | (1-methylimidazol-5-yl)-C≡C- | Cl | CH | CH | CH | CCN | H |

-continued

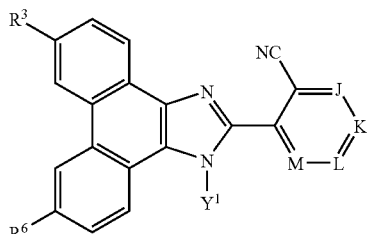

| Ex | R³/R⁶ | R⁶/R³ | J | K | L | M | Y¹ |
|---|---|---|---|---|---|---|---|
| 50 | H₃C-N-tetrazole (2-methyl-tetrazol-5-yl) | Cl | CH | CH | CH | CCN | H |
| 51 | Cl | H₃C-C(OH)(CH₃) (2-hydroxypropan-2-yl) | CH | CH | CH | CCN | H |
| 52 | cyclopropyl-C≡C-CH₃ | Cl | CH | CH | CH | CCN | H |
| 53 | (pyridin-2-yl)-C≡C-CH₃ | Cl | CH | CH | CH | CCN | H |
| 54 | (pyridin-4-yl)-C≡C-CH₃ | Cl | CH | CH | CH | CCN | H |
| 55 | HO-CH(CH₃)-C≡C-CH₃ | Cl | CH | CH | CH | CCN | H |
| 56 | CH₃-C(O)-C≡C-CH₃ | Cl | CH | CH | CH | CCN | H |
| 57 | HO-N=C(CH₃)-C≡C-CH₃ | Cl | CH | CH | CH | CCN | H |
| 58 | H₃CO-N=C(CH₃)-C≡C-CH₃ | Cl | CH | CH | CH | CCN | H |
| 59 | H | H | CH | CH | CH | CCN | HO-C(O)-CH₂-CH₂-C(O)-O-Et |
| 60 | H | H | CH | CH | CH | CCN | H₂PO₄CH₂ |
| 61 | HO-C(CH₃)₂-(5-methylpyridin-2-yl) | Cl | CH | CH | CH | CCN | H |
| 62 | Cl | SO₂CH₃ | CH | CH | CH | CCN | H |

-continued

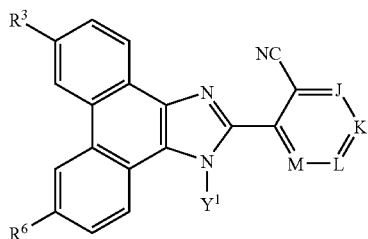

| Ex | R³/R⁶ | R⁶/R³ | J | K | L | M | Y¹ |
|----|-------|-------|----|----|----|-----|----|
| 63 | Cl | H₃C-C(=N-OH)- | CH | CH | CH | CCN | H |
| 64 | Br | H | CH | CH | CH | CCN | H |
| 65 | Cl | H₃C-S(O)₂-C₆H₄- | CH | CH | CH | CCN | H |
| 66 | I | H | CH | CH | CH | CCN | H |
| 67 | CN | H | CH | CH | CH | CCN | H |
| 68 | cyclopropyl | Cl | CH | CH | CH | CCN | H |
| 69 | (CH₃)₂C(OH)-C≡C-CH₃ | cyclopropyl-C≡C- | CH | CH | CH | CCN | H |
| 70 | Cl | F | CH | CH | CH | CCN | H |
| 71 | Cl | cyclopropyl-C(=O)- | CH | CH | CH | CCN | H |
| 72 | Cl | Cl-C₆H₄-S(O)₂-CH₃ | CH | CH | CH | CCN | H |
| 73 | vinyl | H | CH | CH | CH | CCN | H |
| 74 | ethyl | H | CH | CH | CH | CCN | H |
| 75 | cyclopropyl | H | CH | CH | CH | CCN | H |
| 76 | Cl | F₃C-S(O)-CH₃ | CH | CH | CH | CBr | H |
| 77 | Cl | F₃C-S(O)-CH₃ | CH | CH | CH | CCN | H |
| 78 | Cl | SO₂CF₃ | CH | CH | CH | CCN | H |
| 79 | cyclopropyl-C≡C- | H | CH | CH | CH | CCN | H |
| 80 | Cl | (CH₃)₂C(OH)-C₆H₄- | CH | CH | CH | CCN | H |

-continued

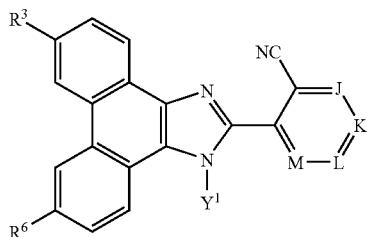

| Ex | R³/R⁶ | R⁶/R³ | J | K | L | M | Y¹ |
|---|---|---|---|---|---|---|---|
| 81 | H₃C—C(OH)(CH₃)—C≡C—CH₃ | Br | CH | CH | CH | CCN | H |
| 82 | Cl | F₃C—C(OH)(CH₃) | CH | CH | CH | CCN | H |
| 83 | cyclopropyl-C≡C-CH₃ | cyclopropyl-C≡C-CH₃ | CH | CH | CH | CCN | H |
| 84 | cyclopropyl-C≡C-CH₃ | H₃C-S(O)₂-C₆H₄-CH₃ | CH | CH | CH | CCN | H |
| 85 | (cyclopropyl)₂C(OH)-C≡C-CH₃ | Cl | CH | CH | CH | CCN | H |
| 86 | (H₃CCH₂)₂C(OH)-C≡C-CH₃ | Cl | CH | CH | CH | CCN | H |
| 87 | Br | H₃C-C(OH)(CH₃)-CH₃ | CH | CH | CH | CCN | H |
| 88 | cyclopropyl-C≡C- | H₃C-C(OH)(CH₃)-CH₃ | CH | CH | CH | CCN | H |
| 89 | cyclopropyl-C≡C- | CN | CH | CH | CH | CCN | H |
| 90 | cyclopropyl-C≡C- | CO₂CH₃ | CH | CH | CH | CCN | H |
| 91 | morpholino-pyridyl-CH₃ | Cl | CH | CH | CH | CCN | H |
| 92 | Cl | CN | CH | CH | CH | CCN | H |

-continued

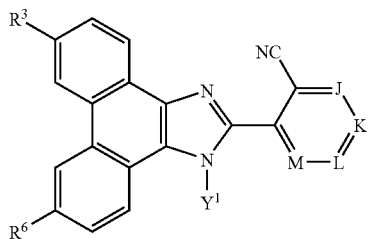

| Ex | R³/R⁶ | R⁶/R³ | J | K | L | M | Y¹ |
|---|---|---|---|---|---|---|---|
| 93 | Cl | 2-(3-methylphenyl)propan-2-ol (HO-C(CH₃)₂-Ar(m-CH₃)) | CH | CH | CH | CCN | H |
| 94 | Br | 2-(pyridin-2-yl)propan-2-ol | CH | CH | CH | CCN | H |
| 95 | 4-(prop-1-ynyl)pyridine N-oxide | Cl | CH | CH | CH | CCN | H |
| 96 | 3-(prop-1-ynyl)pyridine | 2-methylpropan-2-ol | CH | CH | CH | CCN | H |
| 97 | 1-(2-methylbut-3-yn-2-yl)pyrrole | Cl | CH | CH | CH | CCN | H |
| 98 | 2-methylpent-3-yn-2-ol | Br | CH | CH | CH | CCl | H |
| 99 | 4-ethynyltetrahydro-2H-pyran-4-ol | Br | CH | CH | CH | CCl | H |
| 100 | Cl | CO₂i-Pr | CH | CH | CH | CCN | H |
| 101 | Cl | 2,2-dimethoxypropane derivative (H₃CO, H₃CO, CH₃) | CH | CH | CH | CF | H |
| 102 | 4-ethynyltetrahydro-2H-pyran-4-ol | Br | CH | CH | CH | CCN | H |
| 103 | 2-methyl-5-pyridinyl | Cl | CH | CH | CH | CCN | H |

-continued

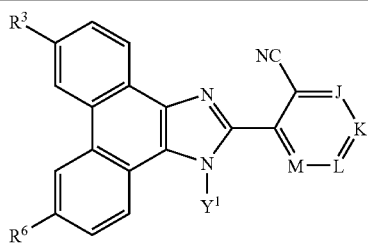

| Ex | R³/R⁶ | R⁶/R³ | J | K | L | M | Y¹ |
|---|---|---|---|---|---|---|---|
| 104 | Br | H₃C-C(=O)- (acetyl) | CH | CH | CH | CCN | H |
| 105 | 4-(2-hydroxypropan-2-yl)phenyl [H₃C, HO, H₃C on C attached to phenyl] | Cl | CH | CH | CH | CCl | H |
| 106 | Br | (H₃CO)₂C(CH₃)- | CH | CH | CH | CCN | H |
| 107 | 4-(prop-1-ynyl)-4-hydroxytetrahydropyran | Cl | CH | CH | CH | CCl | H |
| 108 | 3-(prop-1-ynyl)pyridine N-oxide | Cl | CH | CH | CH | CCN | H |
| 109 | 2-methylpentan-2-ol (H₃C, CH₃, OH, propyl) | Br | CH | CH | CH | CCN | H |
| 110 | 2-methyl-3-pentyn-2-ol (H₃C, HO, H₃C, C≡C-CH₃) | Cl | CH | CH | CH | CCl | H |
| 111 | 2-methyl-3-pentyn-2-ol | cyclopentyl-C≡C- | CH | CH | CH | CCN | H |
| 112 | 3,5-dimethyl-1,2,4-oxadiazole | Br | CH | CH | CH | CCN | H |
| 113 | 3-(ethynyl)pyridine | 3-(ethynyl)pyridine | CH | CH | CH | CCN | H |
| 114 | Et | 2-methyl-3-butyn-2-ol (H₃C, HO, H₃C, C≡C-CH₃) | CH | CH | CH | CCN | H |

-continued

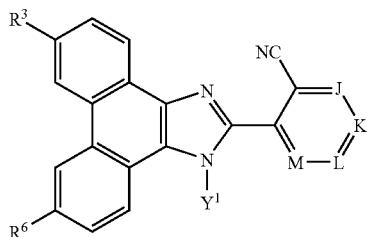

| Ex | R³/R⁶ | R⁶/R³ | J | K | L | M | Y¹ |
|---|---|---|---|---|---|---|---|
| 115 | 2-methyl-2-hydroxypentyl (H₃C, CH₃, OH) | cyclopropyl-C≡C- | CH | CH | CH | CCN | H |
| 116 | Br | 3-hydroxy-3-methylpentyl (H₃C, CH₃, OH, H₃C) | CH | CH | CH | CCN | H |
| 117 | 2-methyl-2-hydroxypentyl (H₃C, CH₃, OH) | Cl | CH | CH | CH | CCN | H |
| 118 | Br | CH₃ | CH | CH | CH | CCN | H |
| 119 | 2-methyl-2-hydroxy-3-butynyl (H₃C, HO, H₃C) | CH₃ | CH | CH | CH | CCN | H |
| 120 | 2-methyl-2-hydroxypentyl (H₃C, CH₃, OH) | CH₃ | CH | CH | CH | CCN | H |
| 121 | methyl (E)-crotonate (H₃CO, O) | Cl | CH | CH | CH | CCN | H |
| 122 | 2-methyl-2-hydroxypentyl (H₃C, CH₃, OH) | H | CH | CH | CH | CCN | H |
| 123 | 2-methyl-2,3-dihydroxy-3-butynyl (H₃C, HO, HO) | Cl | CH | CH | CH | CCN | H |
| 124 | methyl 3,3-dimethylhexanoate (H₃C, O) | Cl | CH | CH | CH | CCN | H |
| 125 | 3,3-dimethylhexanoic acid (HO, O) | Cl | CH | CH | CH | CCN | H |

-continued

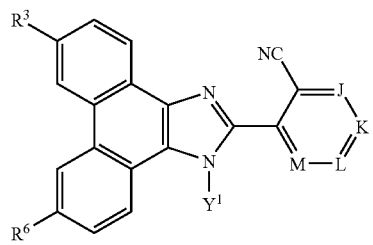

| Ex | R³/R⁶ | R⁶/R³ | J | K | L | M | Y¹ |
|---|---|---|---|---|---|---|---|
| 126 | (cyclopropane-carboxylic acid, methyl) | Cl | CH | CH | CH | CCN | H |
| 127 | (butan-2-one) | Cl | CH | CH | CH | CCN | H |
| 128 | (2-methylbutan-2-yl trifluoroacetate) | Cl | CH | CH | CH | CCN | H |
| 129 | (1-propylcyclobutan-1-ol) | Cl | CH | CH | CH | CCN | H |
| 130 | (2-methylpentane-1,2-diol) | Cl | CH | CH | CH | CCN | H |
| 131 | (2-methylpent-3-yn-2-ol) | Cl | CH | F | CH | CCN | H |
| 132 | (methyl acetate) | (methyl acetate) | CH | CH | CH | CCN | H |
| 133 | (methyl acetate) | (2-methylpropan-2-ol) | CH | CH | CH | CCN | H |
| 134 | (2-methylpropan-2-ol) | (2-methylpropan-2-ol) | CH | CH | CH | CCN | H |
| 135 | (2-methylbutan-2-ol) | Cl | CH | CH | CH | CCN | H |
| 136 | Br | Cl | CH | OH | CH | CCN | H |
| 137 | (2-methylbut-3-yn-2-ol) | Cl | CH | OH | CH | CCN | H |

-continued
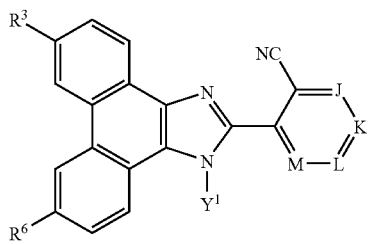
| Ex | R³/R⁶ | R⁶/R³ | J | K | L | M | Y¹ |
|---|---|---|---|---|---|---|---|
| 138 | 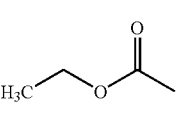 | 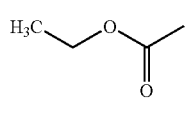 | CH | CH | CH | CCN | H |
| 139 | 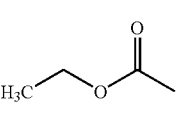 | 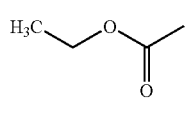 | CH | CH | CH | CCN | H |
| 140 | 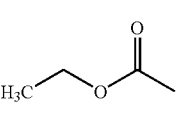 | 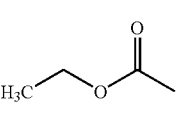 | CH | CH | CH | CCN | H |
| 141 | 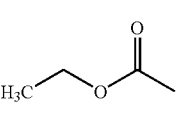 | Br | CH | CH | CH | CCN | H |
| 142 | 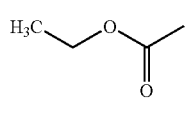 | Cl | CH | Cl | CH | CCN | H |
| 143 | 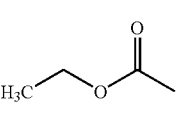 | 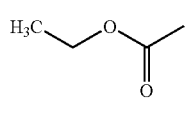 | CH | CH | CH | CCN | H |
| 144 | 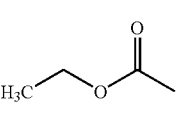 | Cl | CH | CH | CH | CCN | H |
| 145 | Br | 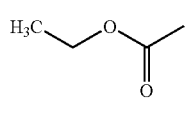 | CH | CH | CH | CCN | H |
| 146 | 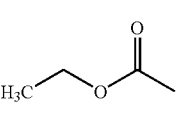 | 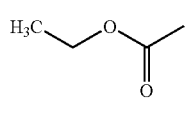 | CH | CH | CH | CCN | H |
| 147 | 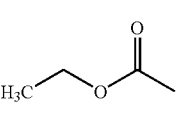 | 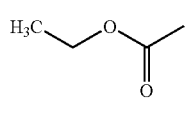 | CH | CH | CH | CCN | H |
| 148 |  |  | CH | CH | CH | CCN | H |

-continued

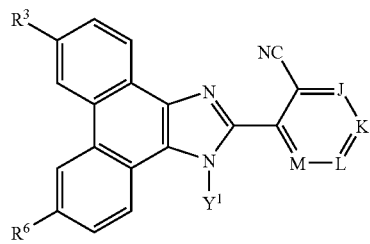

| Ex | R³/R⁶ | R⁶/R³ | J | K | L | M | Y¹ |
|---|---|---|---|---|---|---|---|
| 149 | H₃C-C(=O)-CH₂CH₃ | H₃C-C(=O)-CH₂CH₃ | CH | CH | CH | CCN | H |
| 150 | H₃C-CH(CH₃)-C(=O)-CH₃ | Cl | CH | F | CH | CCN | H |
| 151 | H₃C-C(OH)(CH₃)-C(=O)-CH₃ | Cl | CH | F | CH | CCN | H |
| 152 | HO-C(CH₃)(CH₃)-CH₂CH₃ | Cl | CH | F | CH | CCN | H |
| 153 | cyclopropyl-CH₂CH₂CH₂- | H₃C-C(CH₃)(OH)- | CH | CH | CH | CCN | H |
| 154 | 1-hydroxycyclopentyl-propyl | Cl | CH | CH | CH | CCN | H |
| 155 | 4-pyridyl-propyl | Cl | CH | CH | CH | CCN | H |
| 156 | Br | H₃C-O- | CH | CH | CH | CCN | H |
| 157 | (CH₃)₂C(OH)-C≡C-CH₃ | H₃C-O- | CH | CH | CH | CCN | H |
| 158 | CH₂=C(CH₃)-C≡C-CH₃ | Cl | CH | CH | CH | CCN | H |
| 159 | 3-pyridyl-propyl | 3-pyridyl-propyl | CH | CH | CH | CCN | H |
| 160 | (CH₃)₂C(OH)-C≡C-CH₃ | cyclopropyl-CH₂-O- | CH | CH | CH | CCN | H |

-continued

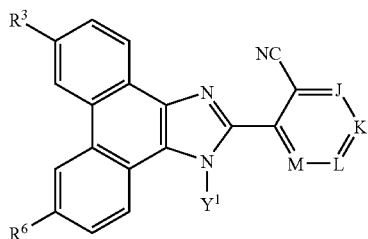

| Ex | R³/R⁶ | R⁶/R³ | J | K | L | M | Y¹ |
|---|---|---|---|---|---|---|---|
| 161 | 3-propylpyridine | H₃C-C(CH₃)(OH)- | CH | CH | CH | CCN | H |
| 162 | 1-(2-methylpentan-2-yl)pyrrole | Cl | CH | CH | CH | CCN | H |
| 163 | HO-C(CH₃)(CH₂CH₃)- | cyclopropyl | CH | CH | CH | CCN | H |
| 164 | 1-methyl-5-propylimidazole | Cl | CH | CH | CH | CCN | H |
| 165 | (CH₃)₂N-CH₂-C≡C- | Cl | CH | CH | CH | CCN | H |
| 166 | (CH₃)₂N-(CH₂)₃- | Cl | CH | CH | CH | CCN | H |
| 167 | CH₃O-(CH₂)₃- | Cl | CH | CH | CH | CCN | H |
| 168 | HO-C(CH₃)(CH₂CH₃)- | cyclopropyl-CH₂-O- | CH | CH | CH | CCN | H |
| 169 | cyclopropyl-CH₂-O- | HO-C(CH₃)(CH₂CH₃)- | CH | F | CH | CCN | H |
| 170 | (CH₃)₂N-C(O)-CH=CH- | Cl | CH | CH | CH | CCN | H |
| 171 | H₃C-C(OH)(CH₃)-(CH₂)₂-CH₃ | Cl | CH | CH | CH | CCN | H |

-continued

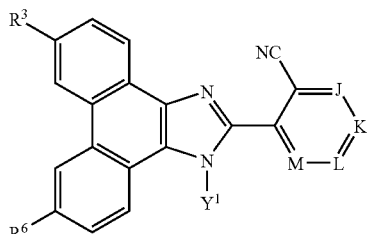

| Ex | R³/R⁶ | R⁶/R³ | J | K | L | M | Y¹ |
|---|---|---|---|---|---|---|---|
| 172 | HO-C(CH₃)₂-CH₂CH₃ | cyclopropyl-CH₂CH₂-O-CH₃ | CH | F | CH | CCN | H |
| 173 | Br | HO-C(CH₃)₂-CH₂CH₃ | CH | CH | CH | CCN | H |
| 174 | HO-C(CH₃)₂-CH₂CH₃ | cyclopropyl-O-CH₃ | CH | CH | CH | CCN | H |
| 175 | HO-C(CH₃)₂-CH₂CH₃ | cyclopropyl-O-CH₃ | CH | F | CH | CCN | H |
| 176 | HO-C(CH₃)₂-CH₂CH₃ | cyclopropyl-CH(O-CH₃)- | CH | CH | CH | CCN | H |
| 177 | HO-C(CH₃)₂-CH₂CH₃ | cyclopropyl-CH(O-CH₃)- | CH | F | CH | CCN | H |
| 178 | OH | Cl | CH | CH | CH | CCN | H |
| 179 | Cl | H₃C-C(=O)-O-CH₂- | CH | CH | CH | CCN | H |
| 180 | HO-C(CH₃)₂-CH₂CH₃ | CF₃-CH₂CH₂-O-CH₃ | CH | CH | CH | CCN | H |
| 181 | Cl | HO-CH(CH₃)-CH₂-C≡C-CH₃ | CH | CH | CH | CCN | H |
| 182 | HO-C(CH₃)₂-CH₂CH₃ | cyclopropyl-CH₂CH₂-O-CH₃ | CH | CH | CH | CCN | H |
| 183 | H₃C-CH₂-CH₂-C(=O)-O-CH₃ | Cl | CH | CH | CH | CCN | H |
| 184 | Cl | H₃C-O-C(=O)-C(CH₃)₂-O-CH₃ | CH | CH | CH | CCN | H |

-continued
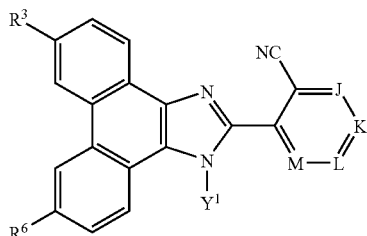
| Ex | R³/R⁶ | R⁶/R³ | J | K | L | M | Y¹ |
|---|---|---|---|---|---|---|---|
| 185 | Cl | methyl 2,2-dimethylpropanoate | CH | CH | CH | CCN | H |
| 186 | methyl cyclopropanecarboxylate | Cl | CH | CH | CH | CCN | H |
| 187 | Br | Cl | CH | OCH₃ | CH | CCN | H |
| 188 | cyclopropylethyl methyl ether | 2-methylbut-3-yn-2-ol | CH | CF | CH | CCN | H |
| 189 | Cl | Br | CH | N | CH | CCN | H |
| 190 | 2-methylbut-3-yn-2-ol | Cl | CH | N | CH | CCN | H |
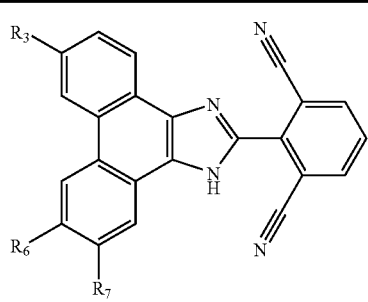
| EX | R3 | R6 | R7 |
|---|---|---|---|
| 191 | 2-methylbut-3-yn-2-ol | Cl | CH₃ |
| 192 | Cl | H | Br |
-continued
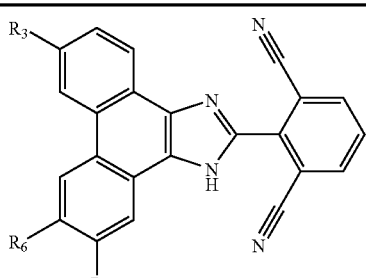
| EX | R3 | R6 | R7 |
|---|---|---|---|
| 193 | Cl | H | 2-methylbut-3-yn-2-ol |
| 194 | Cl | H | 2-methylpentan-2-ol | or a pharmaceutically acceptable salt of any of the above compounds.

18. A pharmaceutical composition comprising a compound according to claim 1 in combination with a pharmaceutically acceptable carrier.

19. The compound according to claim 10, wherein: $R^3$ and $R^6$ are independently selected from the group consisting of: hydrogen, fluoro, chloro, bromo, iodo, cyano, methyl, methoxy, ethyl, vinyl, cyclopropyl, propyl, butyl, —CO$_2$i-Pr, —CO$_2$CH$_3$, —SO$_2$CF$_3$, 3-pyridyl, acetyl,

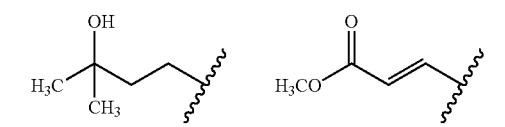
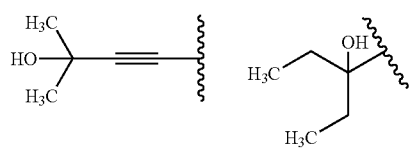
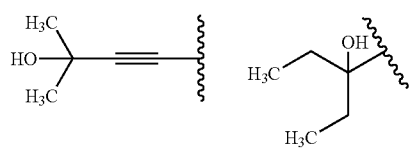
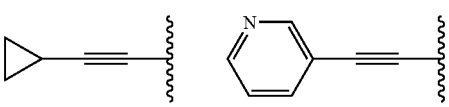
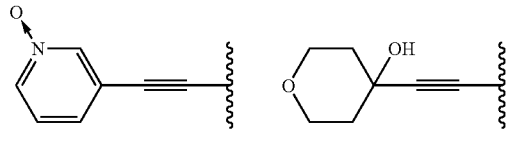
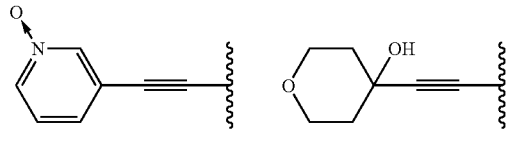
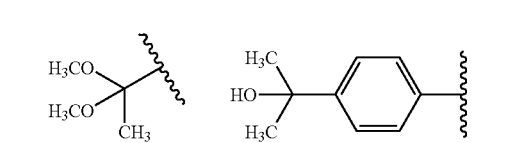
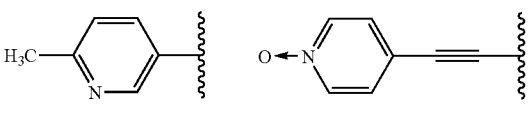
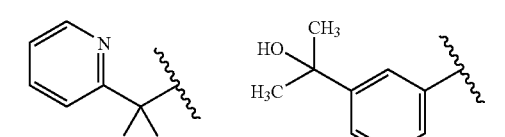
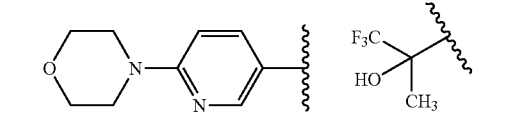

-continued

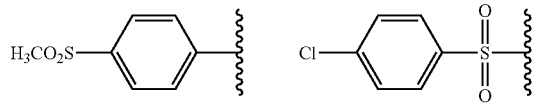
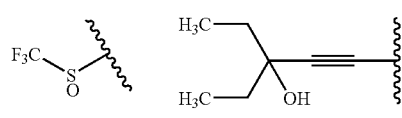
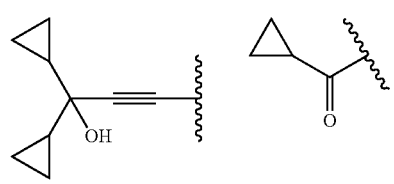
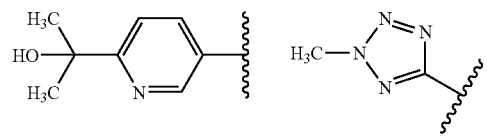
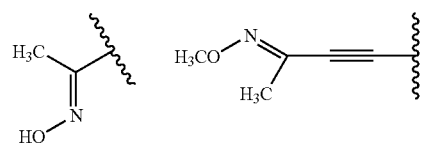
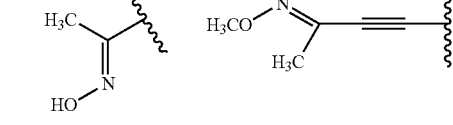
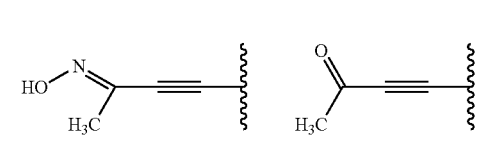
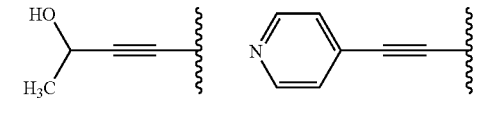
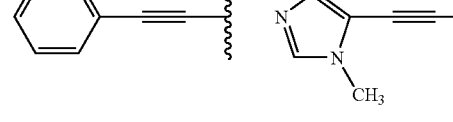
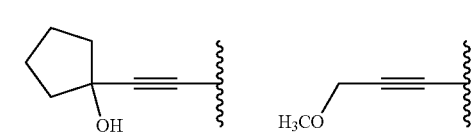
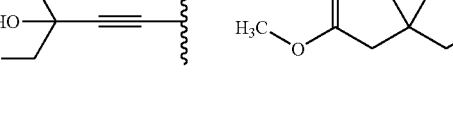

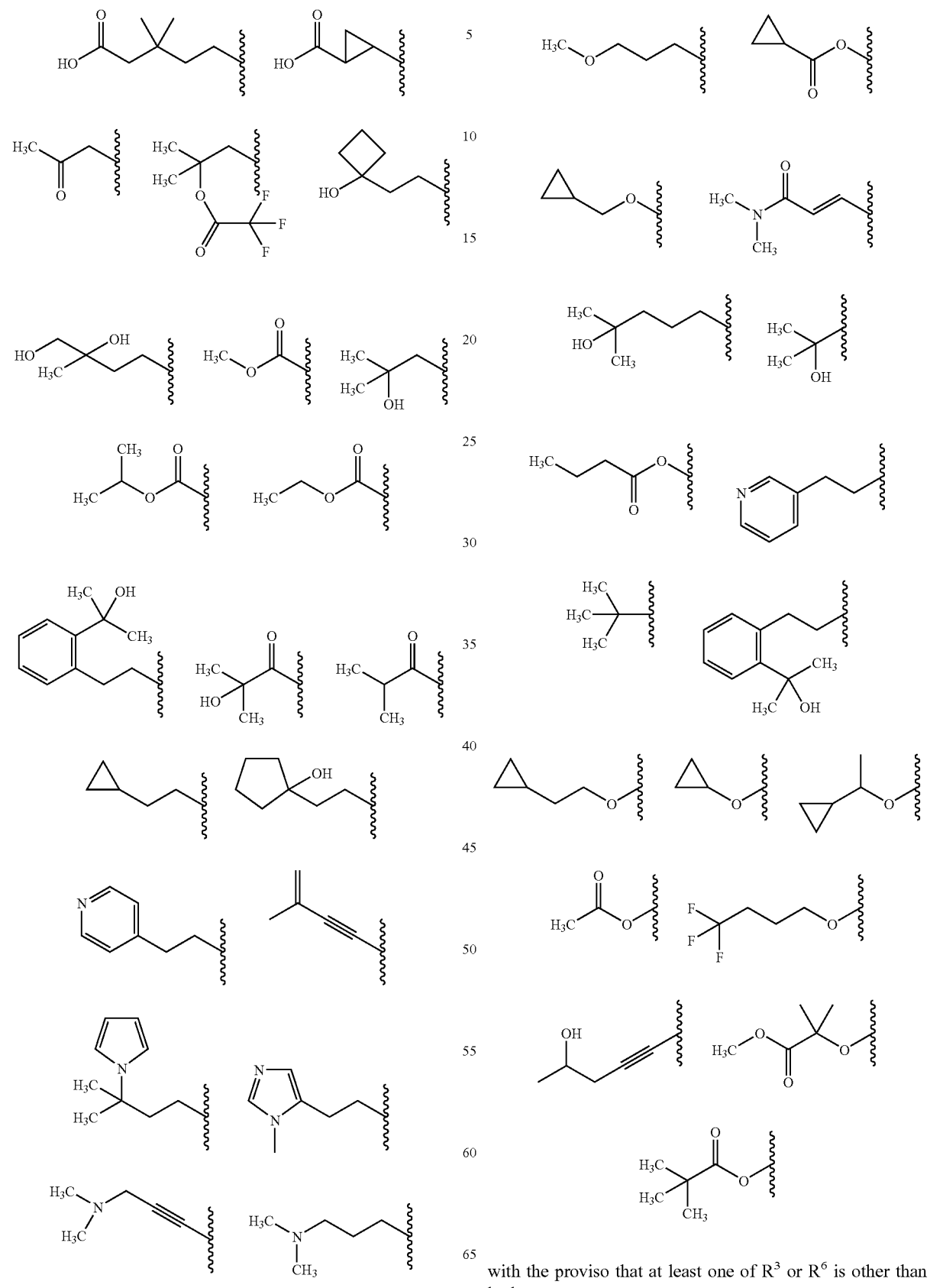
with the proviso that at least one of $R^3$ or $R^6$ is other than hydrogen.

20. The compound according to claim 1 according to Formula B:

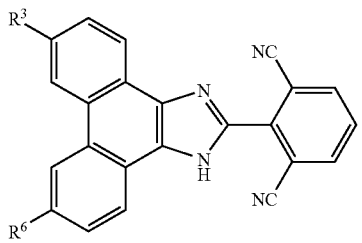

or a prodrug thereof, or a pharmaceutically acceptable salt of said compound or prodrug, wherein:

$R^3$ is 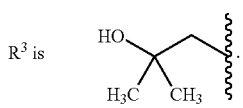

21. The compound according to claim 20 wherein $R^6$ is $R^{12}$—O.

22. The compound according to claim 21 wherein $R^{12}$ is selected from the group consisting of: (1) $C_{1-4}$alkyl and (2) $C_{3-6}$cycloalkyl-$C_{1-4}$alkyl-, wherein said $C_{1-4}$alkyl and $C_{3-6}$cycloalkyl may each be optionally substituted with 1 to 3 substituents independently selected from the group consisting of: OH, F, Cl, Br and I.

23. The compound according to claim 20 wherein $R^6$ is selected from F, Cl, Br and I.

24. The compound according to claim 17 which is

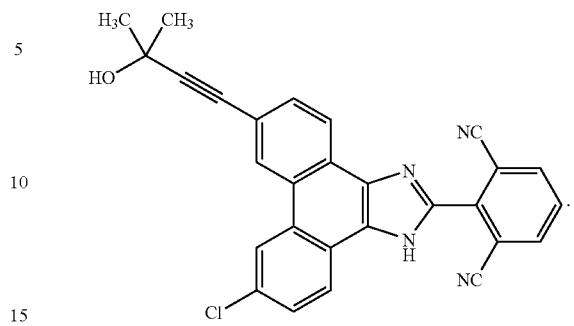

25. A pharmaceutical composition comprising a compound according to claim 24 and a pharmaceutically acceptable carrier.

26. The compound according to claim 17 which is

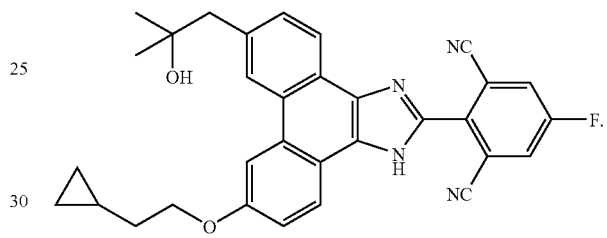

27. A pharmaceutical composition comprising a compound according to claim 26 and a pharmaceutically acceptable carrier.

* * * * *